(12) United States Patent
Best et al.

(10) Patent No.: US 7,718,621 B2
(45) Date of Patent: May 18, 2010

(54) MACROLONES—AMINO SUBSTITUTED QUINOLONES

(75) Inventors: Desmond John Best, Harlow (GB); John Stephen Elder, Harlow (GB); Andrew Keith Forrest, Harlow (GB); Robert John Sheppard, Harlow (GB); Andrea Fajdetic, Zagreb (HR)

(73) Assignees: Glaxo Group Ltd., Brentford, Middlesex (GB); Pliva-Istrazivacki Institut, Zagreb (HR)

( * ) Notice: Subject to any disclaimer, the term of this patent is extended or adjusted under 35 U.S.C. 154(b) by 283 days.

(21) Appl. No.: 11/719,004

(22) PCT Filed: Nov. 9, 2005

(86) PCT No.: PCT/EP2005/012038
§ 371 (c)(1),
(2), (4) Date: May 10, 2007

(87) PCT Pub. No.: WO2006/050942
PCT Pub. Date: May 18, 2006

(65) Prior Publication Data
US 2008/0090773 A1 Apr. 17, 2008

(30) Foreign Application Priority Data
Nov. 11, 2004 (GB) ............... 0424959.5

(51) Int. Cl.
*A61K 31/70* (2006.01)
*C07H 17/08* (2006.01)
(52) U.S. Cl. .......... 514/29; 536/7.4

(58) Field of Classification Search ........ None
See application file for complete search history.

(56) References Cited

U.S. PATENT DOCUMENTS 4,284,629 A 8/1981 Grohe et al. ........ 424/246

FOREIGN PATENT DOCUMENTS

| WO | WO03/042228 A | 5/2003 |
|---|---|---|
| WO | WO2004/039822 A | 5/2004 |

*Primary Examiner*—Elli Peselev
(74) *Attorney, Agent, or Firm*—Reid S. Willis; John Lemanowicz

(57) ABSTRACT

A compound of formula (I)

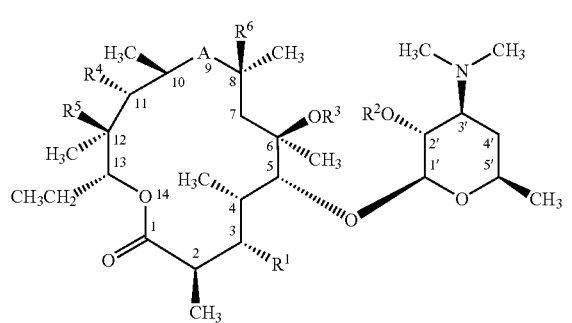

or a pharmaceutically acceptable derivative thereof, having antimicrobial activity, processes for their preparation, compositions containing them and to their use in medicine.

18 Claims, No Drawings

MACROLONES—AMINO SUBSTITUTED QUINOLONES

This application is a 371 of International Application No. PCT/EP2005/012038, filed 9 Nov. 2005.

The present invention relates to novel semi-synthetic macrolides having antimicrobial activity, in particular antibacterial activity. More particularly, the invention relates to 14- and 15-membered macrolides substituted at the 3 position, processes for their preparation, compositions containing them and to their use in medicine.

Macrolide antibacterial agents are known to be useful in the treatment or prevention of bacterial infections. However, the emergence of macrolide-resistant bacterial strains has resulted in the need to develop new macrolide compounds. For example, EP 0 895 999, WO 03/042228 and WO 04/039822 describe derivatives modified at the 4" position of the macrolide ring having antibacterial activity.

According to the present invention, we have now found novel 14- and 15-membered macrolides substituted at the 3 position which also have antimicrobial activity.

Thus, the present invention provides compounds of general formula (I)

(I)

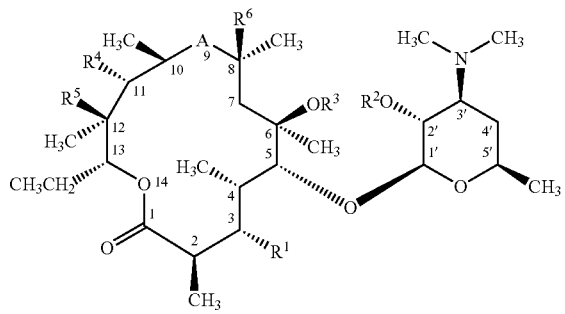

wherein

A is a bivalent radical —C(O)—, —N($R^7$)—$CH_2$—, —CH(N$R^8R^9$)— or —C(=N$R^{10}$)—, or A and $R^4$ taken together with the intervening atoms form a cyclic group having the following formula:

(IA)

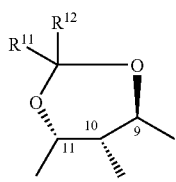

and $R^1$ is a group having the following formula:

(IB)

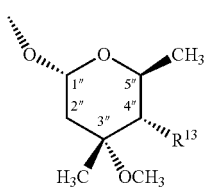

wherein $R^{13}$ is —OC(O)($CH_2$)$_d U^1 R^{14}$, —OC(O)N($R^{15}$)($CH_2$)$_d U^1 R^{14}$, —O($CH_2$)$_d U^1 R^{14}$,

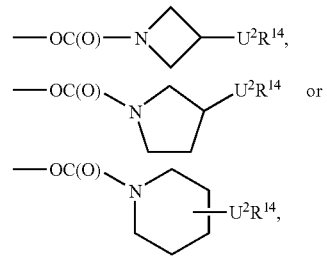

or

A is the bivalent radical —N($R^7$)—$CH_2$— and $R^1$ is a group having the following formula:

(IC)

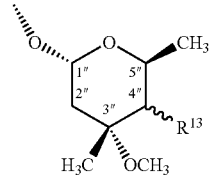

wherein $R^{13}$ is —NHC(O)($CH_2$)$_d U^1 R^{14}$;

$R^2$ is hydrogen or a hydroxyl protecting group;

$R^3$ is hydrogen, $C_{1-4}$alkyl, or $C_{3-6}$alkenyl optionally substituted by 9- or 10-membered fused bicyclic heteroaryl;

$R^4$ is hydroxy, $C_{3-6}$alkenyloxy optionally substituted by 9- or 10-membered fused bicyclic heteroaryl, or $C_{1-6}$alkoxy optionally substituted by $C_{1-6}$alkoxy or —O($CH_2$)$_e$N$R^7 R^{16}$, or $R^4$ and A taken together with the intervening atoms form a cyclic group of formula (IA), $R^5$ is hydroxy, or $R^4$ and $R^5$ taken together with the intervening atoms form a cyclic group having the following formula:

(ID)

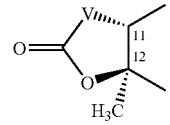

wherein V is a bivalent radical —$CH_2$—, —CH(CN)—, —O—, —N($R^{17}$)— or —CH(S$R^{17}$)—, with the proviso that when $R^1$ is a group of formula (IC), V is —O—;

$R^6$ is hydrogen or fluorine;

$R^7$ is hydrogen or $C_{1-6}$alkyl;

$R^8$ and $R^9$ are each independently hydrogen, $C_{1-6}$alkyl or —C(O)$R^{18}$, or $R^8$ and $R^9$ together form =CH(C$R^{18}R^{19}$)$_f$aryl, =CH(C$R^{18}R^{19}$)$_f$heterocyclyl, =C$R^{18}R^{19}$ or =C($R^{18}$)C(O)O$R^{18}$, wherein the alkyl, aryl and heterocyclyl groups are optionally substituted by up to three groups independently selected from $R^{20}$;

$R^{10}$ is —O$R^{21}$;

$R^{11}$ and $R^{12}$ are each independently hydrogen, $C_{1-6}$alkyl, heteroaryl, or aryl optionally substituted by one or two groups independently selected from hydroxyl and $C_{1-6}$alkoxy;

$R^{14}$ is a heterocyclic group having the following formula:

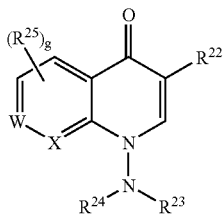

(IE)

$R^{15}$, $R^{16}$, $R^{18}$ and $R^{19}$ are each independently hydrogen or $C_{1-6}$alkyl;

$R^{17}$ is hydrogen or $C_{1-4}$alkyl optionally substituted by a group selected from optionally substituted phenyl, optionally substituted 5- or 6-membered heteroaryl and optionally substituted 9- or 10-membered fused bicyclic heteroaryl;

$R^{20}$ is halogen, cyano, nitro, trifluoromethyl, azido, —C(O)$R^{26}$, —C(O)O$R^{26}$, —OC(O)$R^{26}$, —OC(O)O$R^{26}$, —NR$^{27}$C(O)$R^{28}$, —C(O)NR$^{27}$R$^{28}$, —NR$^{27}$R$^{28}$, hydroxy, $C_{1-6}$alkyl, —S(O)$_n$C$_{1-6}$alkyl, $C_{1-6}$alkoxy, —(CH$_2$)$_i$aryl or —(CH$_2$)$_i$heteroaryl, wherein the alkoxy group is optionally substituted by up to three groups independently selected from —NR$^{18}$R$^{19}$, halogen and —OR$^{18}$, and the aryl and heteroaryl groups are optionally substituted by up to five groups independently selected from halogen, cyano, nitro, trifluoromethyl, azido, —C(O)R$^{29}$, —C(O)OR$^{29}$, —OC(O)OR$^{29}$, —NR$^{30}$C(O)R$^{31}$, —C(O)NR$^{30}$R$^{31}$, —NR$^{30}$R$^{31}$, hydroxy, $C_{1-6}$alkyl and $C_{1-6}$alkoxy;

$R^{21}$ is hydrogen, $C_{1-6}$alkyl, $C_{3-7}$cycloalkyl, $C_{3-6}$alkenyl or a 5- or 6-membered heterocyclic group, wherein the alkyl, cycloalkyl, alkenyl and heterocyclic groups are optionally substituted by up to three groups independently selected from optionally substituted 5- or 6-membered heterocyclic group, optionally substituted 5- or 6-membered heteroaryl, —OR$^{32}$, —S(O)$_j$R$^{32}$, —NR$^{32}$R$^{33}$, —CONR$^{32}$R$^{33}$, halogen and cyano;

$R^{22}$ is hydrogen, —C(O)OR$^{34}$, —C(O)NHR$^{34}$, —C(O)CH$_2$NO$_2$ or —C(O)CH$_2$SO$_2$R$^7$;

$R^{23}$ and $R^{24}$ are each independently hydrogen, $C_{1-4}$alkyl or $C_{3-7}$cycloalkyl, wherein the alkyl and cycloalkyl groups are optionally substituted by up to three groups independently selected from hydroxy, cyano, $C_{1-4}$alkoxy, —CONR$^{35}$R$^{36}$ and —NR$^{35}$R$^{36}$, $R^{23}$ and $R^{24}$, together with the nitrogen atom to which they are bound, form a 5- or 6-membered heterocyclic ring optionally containing one additional heteroatom selected from oxygen, sulfur and N—R$^{37}$, or $R^{23}$ is $C_{1-4}$alkyl, X is —C(R$^{41}$)—, and R$^{24}$ and R$^{41}$ are linked to form a cyclic group having the following formula:

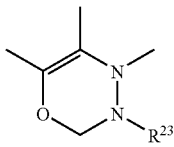

(IF)

$R^{25}$ is halogen, $C_{1-4}$alkyl, $C_{1-4}$thioalkyl, $C_{1-4}$alkoxy, —NH$_2$, —NH(C$_{1-4}$alkyl) or —N(C$_{1-4}$alkyl)$_2$;

$R^{26}$ is hydrogen, $C_{1-10}$alkyl, —(CH$_2$)$_k$aryl or —(CH$_2$)$_k$heteroaryl;

$R^{27}$ and $R^{28}$ are each independently hydrogen, —OR$^{18}$, $C_{1-6}$alkyl, —(CH$_2$)$_m$aryl or —(CH$_2$)$_m$heterocyclyl;

$R^{29}$ is hydrogen, $C_{1-10}$alkyl, —(CH$_2$)$_n$aryl or —(CH$_2$)$_n$heteroaryl;

$R^{30}$ and $R^{31}$ are each independently hydrogen, —OR$^{18}$, $C_{1-6}$alkyl, —(CH$_2$)$_p$aryl or —(CH$_2$)$_p$heterocyclyl;

$R^{32}$ and $R^{33}$ are each independently hydrogen, $C_{1-4}$alkyl or $C_{1-4}$alkoxyC$_{1-4}$alkyl;

$R^{34}$ is hydrogen,
$C_{1-6}$alkyl optionally substituted by up to three groups independently selected from halogen, cyano, $C_{1-4}$alkoxy optionally substituted by phenyl or $C_{1-4}$alkoxy, —C(O)$C_{1-6}$alkyl, —C(O)OC$_{1-6}$alkyl, —OC(O)C$_{1-6}$alkyl, —OC(O)OC$_{1-6}$alkyl, —C(O)NR$^{38}$R$^{39}$, —NR$^{38}$R$^{39}$ and phenyl optionally substituted by nitro or —C(O)OC$_{1-6}$alkyl,
—(CH$_2$)$_q$C$_{3-7}$cycloalkyl,
—(CH$_2$)$_q$heterocyclyl,
—(CH$_2$)$_q$heteroaryl,
—(CH$_2$)$_q$aryl,
$C_{3-6}$alkenyl, or
$C_{3-6}$alkynyl;

$R^{35}$ and $R^{36}$ are each independently hydrogen or $C_{1-4}$alkyl;

$R^{37}$ is hydrogen or methyl;

$R^{38}$ and $R^{39}$ are each independently hydrogen or $C_{1-6}$alkyl optionally substituted by phenyl or —C(O)OC$_{1-6}$alkyl, or $R^{38}$ and $R^{39}$, together with the nitrogen atom to which they are bound, form a 5- or 6-membered heterocyclic group optionally containing one additional heteroatom selected from oxygen, sulfur and N—R$^{37}$;

$R^{40}$ is hydrogen, $C_{1-4}$alkyl, $C_{3-7}$cycloalkyl, optionally substituted phenyl or benzyl, acetyl or benzoyl;

$R^{41}$ is hydrogen or $R^{25}$, or, when X is —C(R$^{41}$)—, $R^{41}$ and $R^{24}$ may be linked to form a cyclic group of formula (IF);

$U^1$ is a bivalent radical —Y(CH$_2$)$_r$Z— or —Y(CH$_2$)$_r$—;

$U^2$ is $U^1$ or a bivalent radical —O—, —N(R$^{40}$)—, —S(O)$_s$— or —CH$_2$—;

Y and Z are each independently a bivalent radical —N(R$^{40}$)—, —O—, —S(O)$_s$—, —N(R$^{40}$)C(O)—, —C(O)N(R$^{40}$)— or —N[C(O)R$^{40}$]—;

W and X are each independently —C(R$^{41}$)— or a nitrogen, with the proviso that W and X are not both nitrogen;

d is an integer from 2 to 5;

e is an integer from 2 to 4;

f, i, k, m, n, p and q are each independently integers from 0 to 4;

g, h, j and s are each independently integers from 0 to 2;

r is an integer from 2 to 5;

and pharmaceutically acceptable derivatives thereof.

In an alternative aspect the invention also provides compounds wherein $R^{23}$ is $C_{1-4}$alkyl, X is —C(R$^{41}$)—, and $R^{24}$ and $R^{41}$ are linked to form a cyclic group having the following formula:

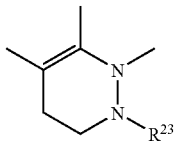

(IF-a)

The term "pharmaceutically acceptable" as used herein means a compound which is suitable for pharmaceutical use. Salts and solvates of compounds of the invention which are suitable for use in medicine are those wherein the counterion or associated solvent is pharmaceutically acceptable. However, salts and solvates having non-pharmaceutically acceptable counterions or associated solvents are within the scope of the present invention, for example, for use as intermediates in the preparation of other compounds of the invention and their pharmaceutically acceptable salts and solvates.

The term "pharmaceutically acceptable derivative" as used herein means any pharmaceutically acceptable salt, solvate or prodrug, e.g. ester, of a compound of the invention, which upon administration to the recipient is capable of providing (directly or indirectly) a compound of the invention, or an active metabolite or residue thereof. Such derivatives are recognizable to those skilled in the art, without undue experimentation. Nevertheless, reference is made to the teaching of Burger's Medicinal Chemistry and Drug Discovery, 5$^{th}$ Edition, Vol 1: Principles and Practice, which is incorporated herein by reference to the extent of teaching such derivatives. Examples of pharmaceutically acceptable derivatives are salts, solvates, esters, carbamates and phosphate esters. Additional examples of pharmaceutically acceptable derivatives are salts, solvates and esters. Further examples of pharmaceutically acceptable derivatives are salts and esters, such as salts.

The compounds of the present invention may be in the form of and/or may be administered as a pharmaceutically acceptable salt. For a review on suitable salts see Berge et al., J. Pharm. Sci., 1977, 66, 1-19.

Typically, a pharmaceutical acceptable salt may be readily prepared by using a desired acid or base as appropriate. The salt may precipitate from solution and be collected by filtration or may be recovered by evaporation of the solvent. For example, an aqueous solution of an acid such as lactobionic acid may be added to a solution of a compound of formula (I) in a solvent such as acetonitrile, acetone or THF, and the resulting mixture evaporated to dryness, redissolved in water and lyophilised to obtain the acid addition salt as a solid. Alternatively, a compound of formula (I) may be dissolved in a suitable solvent, for example an alcohol such as isopropanol, and the acid may be added in the same solvent or another suitable solvent. The resulting acid addition salt may then be precipitated directly, or by addition of a less polar solvent such as diisopropyl ether or hexane, and isolated by filtration.

The skilled person will appreciate that where the compound of formula (I) contains more than one basic group bis salts (2:1 acid:compound of formula (I)) or tris salts (3:1 acid:compound of formula (I)) may also be formed and are salts according to the present invention.

Suitable addition salts are formed from inorganic or organic acids which form non-toxic salts and examples are lactobionate, mandelate (including (S)-(+)-mandelate, (R)-(−)-mandelate and (R,S)-mandelate), hydrochloride, hydrobromide, hydroiodide, sulfate, bisulfate, nitrate, phosphate, hydrogen phosphate, acetate, trifluoroacetate, maleate, malate, fumarate, lactate, tartrate, citrate, formate, gluconate, succinate, ethyl succinate (4-ethoxy-4-oxo-butanoate), pyruvate, oxalate, oxaloacetate, saccharate, benzoate, alkyl or aryl sulphonates (eg methanesulphonate, ethanesulphonate, benzenesulphonate or p-toluenesulphonate) and isethionate. In one embodiment, suitable salts include lactobionate, citrate, succinate, (L)-(+)-tartrate, (S)-(+)-mandelate and bis-(S)-(+)-mandelate, for example lactobionate, citrate, succinate and (L)-(+)-tartrate, such as lactobionate and citrate.

Pharmaceutically acceptable base salts include ammonium salts, alkali metal salts such as those of sodium and potassium, alkaline earth metal salts such as those of calcium and magnesium and salts with organic bases, including salts of primary, secondary and tertiary amines, such as isopropylamine, diethylamine, ethanolamine, trimethylamine, dicyclohexyl amine and N-methyl-D-glucamine.

Compounds of the invention may have both a basic and an acidic centre may therefore be in the form of zwitterions.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compounds of the invention are within the scope of the invention. The salts of the compound of formula (I) may form solvates (e.g. hydrates) and the invention also includes all such solvates.

The term "prodrug" as used herein means a compound which is converted within the body, e.g. by hydrolysis in the blood, into its active form that has medical effects. Pharmaceutically acceptable prodrugs are described in T. Higuchi and V. Stella, "Prodrugs as Novel Delivery Systems", Vol. 14 of the A.C.S. Symposium Series; Edward B. Roche, ed., "Bioreversible Carriers in Drug Design", American Pharmaceutical Association and Pergamon Press, 1987; and in D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

Prodrugs are any covalently bonded carriers that release a compound of formula (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol, sulfhydryl and amine functional groups of the compounds of formula (I). Further, in the case of a carboxylic acid (—COOH), esters may be employed, such as methyl esters, ethyl esters, and the like. Esters may be active in their own right and/or be hydrolysable under in vivo conditions in the human body. Suitable pharmaceutically acceptable in vivo hydrolysable ester groups include those which break down readily in the human body to leave the parent acid or its salt.

References hereinafter to a compound according to the invention include both compounds of formula (I) and their pharmaceutically acceptable derivatives.

With regard to stereoisomers, the compounds of formula (I) have more than one asymmetric carbon atom. In the general formula (I) as drawn, the solid wedge shaped bond indicates that the bond is above the plane of the paper. The broken bond indicates that the bond is below the plane of the paper. The wavy bond ( ～ ) indicates that the bond can be either above or below the plane of the paper. Thus, when R$^1$ is a group of formula (IC), the present invention includes both epimers at the 4" carbon, and mixtures thereof.

However, where a wavy bond ( ～ ) bisects another bond at approximately 90° then this is intended to identify the bond through which the moiety is linked to the rest of the molecule.

It will be appreciated that the substituents on the macrolide may also have one or more asymmetric carbon atoms. Thus, the compounds of structure (I) may occur as individual enantiomers or diastereomers. All such isomeric forms are included within the present invention, including mixtures thereof.

Where a compound of the invention contains an alkenyl group, cis (Z) and trans (E) isomerism may also occur. The present invention includes the individual stereoisomers of the compound of the invention and, where appropriate, the individual tautomeric forms thereof, together with mixtures thereof.

Separation of diastereoisomers or cis and trans isomers may be achieved by conventional techniques, e.g. by fractional crystallisation, chromatography or HPLC. A stereoisomeric mixture of the agent may also be prepared from a corresponding optically pure intermediate or by resolution, such as by HPLC, of the corresponding mixture using a suitable chiral support or by fractional crystallisation of the diastereoisomeric salts formed by reaction of the corresponding mixture with a suitable optically active acid or base, as appropriate.

The compounds of formula (I) may be in crystalline or amorphous form. Furthermore, some of the crystalline forms of the compounds of structure (I) may exist as polymorphs, which are included in the present invention.

Compounds wherein $R^2$ represents a hydroxyl protecting group are in general intermediates for the preparation of other compounds of formula (I).

When the group $OR^2$ is a protected hydroxyl group this is conveniently an ether or an acyloxy group. Examples of particularly suitable ether groups include those in which $R^2$ is a trialkylsilyl (i.e. trimethylsilyl). When the group $OR^2$ represents an acyloxy group, then examples of suitable groups $R^2$ include acetyl or benzoyl.

When $R^{13}$ is

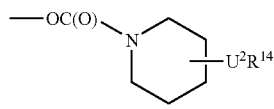

the $-U^2R^{14}$ group is typically attached at the 3- or 4-position on the piperidine ring.

When $R^{14}$ is a heterocyclic group having the following structure:

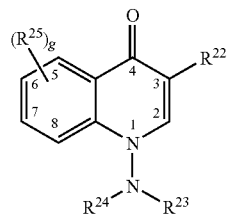

said heterocyclic is linked in the 5, 6, 7 or 8 position to the $U^1$ or $U^2$ group as above defined. In one embodiment, the heterocyclic is linked in the 6 or 7 position. When present, the $R^{25}$ group or groups may be attached at any otherwise vacant or unoccupied position on the ring.

When $R^{14}$ is a heterocyclic group having the following structure:

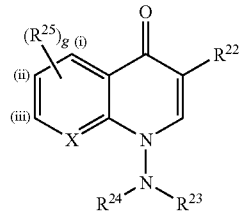

wherein X is —C($R^{41}$)— where $R^{41}$ is $R^{25}$, or $R^{41}$ and $R^{24}$ are linked to form a cyclic group of formula (IF), said heterocyclic is linked in the (i), (ii) or (iii) position to the $U^1$ or $U^2$ group as above defined. In one embodiment, the heterocyclic is linked in the (ii) or (iii) position. When present, the $R^{25}$ group or groups may be attached at any otherwise vacant or unoccupied position on the ring.

When $R^{14}$ is a heterocyclic group having the following structure:

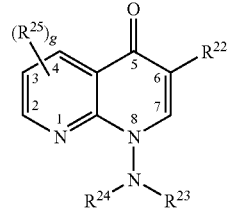

said heterocyclic is linked in the 2, 3 or 4 position to the $U^1$ or $U^2$ group as above defined. In one embodiment, the heterocyclic is linked in the 2 or 3 position. When present, the $R^{25}$ group or groups may be attached at any otherwise vacant or unoccupied position on the ring.

When $R^{14}$ is a heterocyclic group having the following structure:

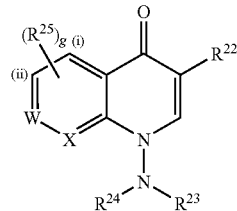

wherein W is N and X is —C($R^{41}$)— where $R^{41}$ is $R^{25}$ or $R^{41}$ and $R^{24}$ are linked to form a cyclic group of formula (IF), or W is —C($R^{25}$)— and X is N or —C($R^{41}$)— where $R^{41}$ is $R^{25}$ or $R^{41}$ and $R^{24}$ are linked to form a cyclic group of formula (IF), said heterocyclic is linked in the (i) or (ii) position to the $U^1$ or $U^2$ group as above defined. In one embodiment, the heterocyclic is linked in the (ii) position. When present, the $R^{25}$ group or groups may be attached at any otherwise vacant or unoccupied position on the ring.

When $R^{14}$ is a heterocyclic group having the following structure:

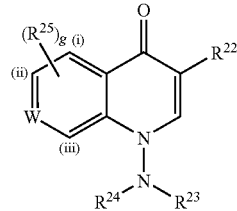

wherein W is N or —C($R^{25}$)—, said heterocyclic is linked in the (i), (ii) or (iii) position to the $U^1$ or $U^2$ group as above defined. In one embodiment, the heterocyclic is linked in the (ii) position. When present, the $R^{25}$ group or groups may be attached at any otherwise vacant or unoccupied position on the ring.

The term "alkyl" as used herein as a group or a part of a group refers to a straight or branched hydrocarbon chain containing the specified number of carbon atoms. For example, $C_{1-10}$alkyl means a straight or branched alkyl containing at least 1, and at most 10, carbon atoms. Examples of "alkyl" as used herein include, but are not limited to, methyl, ethyl, n-propyl, n-butyl, n-pentyl, isobutyl, isopropyl, t-butyl, hexyl, heptyl, octyl, nonyl and decyl. A $C_{1-4}$alkyl group is preferred, for example methyl, ethyl, n-propyl, isopropyl, n-butyl, isobutyl or t-butyl.

The term "$C_{3-7}$cycloalkyl" group as used herein refers to a non-aromatic monocyclic hydrocarbon ring of 3 to 7 carbon atoms such as, for example, cyclopropyl, cyclobutyl, cyclopentyl, cyclohexyl or cycloheptyl.

The term "alkoxy" as used herein refers to a straight or branched chain alkoxy group containing the specified number of carbon atoms. For example, $C_{1-6}$alkoxy means a straight or branched alkoxy containing at least 1, and at most 6, carbon atoms. Examples of "alkoxy" as used herein include, but are not limited to, methoxy, ethoxy, propoxy, prop-2-oxy, butoxy, but-2-oxy, 2-methylprop-1-oxy, 2-methylprop-2-oxy, pentoxy and hexyloxy. A $C_{1-4}$alkoxy group is preferred, for example methoxy, ethoxy, propoxy, prop-2-oxy, butoxy, but-2-oxy or 2-methylprop-2-oxy.

The term "alkenyl" as used herein as a group or a part of a group refers to a straight or branched hydrocarbon chain containing the specified number of carbon atoms and containing at least one double bond. For example, the term "$C_{2-6}$alkenyl" means a straight or branched alkenyl containing at least 2, and at most 6, carbon atoms and containing at least one double bond. Similarly, the term "$C_{3-6}$alkenyl" means a straight or branched alkenyl containing at least 3, and at most 6, carbon atoms and containing at least one double bond. Examples of "alkenyl" as used herein include, but are not limited to, ethenyl, 2-propenyl, 3-butenyl, 2-butenyl, 2-pentenyl, 3-pentenyl, 3-methyl-2-butenyl, 3-methylbut-2-enyl, 3-hexenyl and 1,1-dimethylbut-2-enyl. It will be appreciated that in groups of the form —O—$C_{2-6}$alkenyl, the double bond is preferably not adjacent to the oxygen.

The term "alkynyl" as used herein as a group or a part of a group refers to a straight or branched hydrocarbon chain containing the specified number of carbon atoms and containing at least one triple bond. For example, the term "$C_{3-6}$alkynyl" means a straight or branched alkynyl containing at least 3, and at most 6, carbon atoms and containing at least one triple bond. Examples of "alkynyl" as used herein include, but are not limited to, propynyl, 1-butynyl, 2-butynyl, 1-pentynyl and 3-methyl-1-butynyl.

The term "aryl" as used herein refers to an aromatic carbocyclic moiety such as phenyl, biphenyl or naphthyl, for example phenyl.

The term "heteroaryl" as used herein, unless otherwise defined, refers to an aromatic heterocycle of 5 to 10 members, having at least one heteroatom selected from nitrogen, oxygen and sulfur, and containing at least 1 carbon atom, including both mono and bicyclic ring systems. Examples of heteroaryl rings include, but are not limited to, furanyl, thiophenyl, pyrrolyl, pyrazolyl, imidazolyl, oxazolyl, isoxazolyl, thiazolyl, isothiazolyl, triazolyl, oxadiazolyl, tetrazolyl, thiadiazolyl, pyridyl, pyridazinyl, pyrazinyl, pyrimidinyl, triazinyl, quinolinyl, isoquinolinyl, 1,2,3,4-tetrahydroisoquinolinyl, benzofuranyl, benzimidazolyl, benzothienyl, benzoxazolyl, 1,3-benzodioxazolyl, indolyl, benzothiazolyl, furylpyridine, oxazolopyridyl and benzothiophenyl.

The term "5- or 6-membered heteroaryl" as used herein as a group or a part of a group refers to a monocyclic 5- or 6-membered aromatic heterocycle containing at least one heteroatom independently selected from oxygen, nitrogen and sulfur. Examples include, but are not limited to, furanyl, thiophenyl, pyrrolyl, pyrazolyl, imidazolyl, oxazolyl, isoxazolyl, thiazolyl, isothiazolyl, triazolyl, oxadiazolyl, tetrazolyl, pyridyl, pyridazinyl, pyrazinyl, pyrimidinyl and triazinyl.

The term "9- or 10-membered fused bicyclic heteroaryl" as used herein as a group or a part of a group refers to a 9- or 10-membered fused bicyclic heteroaryl containing at least one heteroatom selected from oxygen, nitrogen and sulphur. Examples include, but are not limited to, quinolinyl, isoquinolinyl, 1,2,3,4-tetrahydroisoquinolinyl, benzofuranyl, benzimidazolyl, benzothienyl, benzoxazolyl, 1,3-benzodioxazolyl, indolyl, benzothiazolyl, furylpyridine, oxazolopyridyl and benzothiophenyl.

The term "heterocyclyl" as used herein, unless otherwise defined, refers to a monocyclic or bicyclic 3- to 10-membered saturated or non-aromatic, unsaturated hydrocarbon ring containing at least one heteroatom selected from oxygen, nitrogen and sulfur. Preferably, the heterocyclyl ring has five or six ring atoms. Examples of heterocyclyl groups include, but are not limited to, pyrrolidinyl, tetrahydrofuranyl, tetrahydrothiophenyl, imidazolidinyl, pyrazolidinyl, piperidyl, piperazinyl, morpholino, tetrahydropyranyl and thiomorpholino.

The term "5- or 6-membered heterocyclic group" as used herein as a group or part of a group refers to a monocyclic 5- or 6-membered saturated hydrocarbon ring containing at least one heteroatom independently selected from oxygen, nitrogen and sulfur. Examples of such heterocyclyl groups include, but are not limited to, pyrrolidinyl, tetrahydrofuranyl, tetrahydrothiophenyl, imidazolidinyl, pyrazolidinyl, piperidyl, piperazinyl, morpholino, tetrahydropyranyl and thiomorpholino.

The term "halogen" refers to a fluorine, chlorine, bromine or iodine atom.

The terms "optionally substituted phenyl", "optionally substituted phenyl or benzyl", "optionally substituted 5- or 6-membered heteroaryl", "optionally substituted 9- or 10-membered fused bicyclic heteroaryl" or "optionally substituted 5- or 6-membered heterocyclic group" as used herein refer to a group which is substituted by 1 to 3 groups independently selected from halogen, $C_{1-4}$alkyl, $C_{1-4}$alkoxy, hydroxy, nitro, cyano, amino, $C_{1-4}$alkylamino or di$C_{1-4}$alkylamino, phenyl and 5- or 6-membered heteroaryl.

As the skilled person will appreciate, the compounds of formula (I) are derivatives of known 14- and 15-membered macrolides derived from erythromycin A that have antibacterial activity and contain a cladinose moiety with a hydroxy group or amino group at the 4" position. The 14- and 15-membered macrolides which may be derivatised according to the invention include, for example, the following:

azithromycin,
11-O-methyl-azithromycin,
azithromycin 11,12-carbonate,
6-O-methyl erythromycin A,
6-O-methyl erythromycin A 9-oxime,
6-O-methyl erythromycin A 9-O-alkyl-oximes,
erythromycin 9-oxime,
erythromycin 9-O-alkyl-oximes,
erythromycin 11,12-carbonate,
erythromycin 9-oxime 11,12-carbonate,
6-O-methyl-11-deoxy-11-amino-erythromycin A 11,12-carbamate,
(9S)-9-dihydro-erythromycin, and
(9S)-9-dihydro-erythromycin 9,11-ethylidene acetal, and the above macrolides in which the 4" hydroxyl group is replaced by an amino group to give a macrolide having (R), (S) or (R,S) stereochemistry at the 4" position.

In the compounds of formula (I), the heterocyclic group of formula (IE) ($R^{14}$) is attached to the 4" position of the 14- or 15-membered macrolide via a linker chain. Linker chains suitable for use according to the present invention include, for example, the following:

—OC(O)(CH$_2$)$_2$NH(CH$_2$)$_3$—;
—OC(O)(CH$_2$)$_2$NH(CH$_2$)$_2$S—;
—OC(O)(CH$_2$)$_2$NH(CH$_2$)$_2$O—;
—O(CH$_2$)$_3$N(CH$_3$)(CH$_2$)$_3$—;
—O(CH$_2$)$_2$NH(CH$_2$)$_2$S—;
—O(CH$_2$)$_3$O(CH$_2$)$_3$—; and
—O(CH$_2$)$_2$NH(CH$_2$)$_2$O—.

In one embodiment, A is —N($R^7$)—CH$_2$—, —CH(N$R^8R^9$)— or —C(=N$R^{10}$)—, or A and $R^4$ taken together with the intervening atoms form a cyclic group having the following formula:

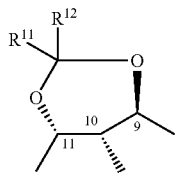

(IA)

In another embodiment, A is —C(O)—, —N($R^7$)—CH$_2$— or —CH(N$R^8R^9$)—, or A and $R^4$ taken together with the intervening atoms form a cyclic group having the following formula:

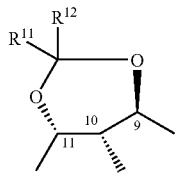

(IA)

In another embodiment, A is —C(O)—, —N($R^7$)—CH$_2$— or —CH(N$R^8R^9$)—. In another embodiment, A is —C(O)—, —CH(N$R^8R^9$)— or —C(=N$R^{10}$)—. In a further embodiment, A is —C(O)— or —CH(N$R^8R^9$)—. Representative examples of A include —C(O)—, —N($R^7$)—CH$_2$— and —C(=N$R^{10}$)—.

A representative example of $R^1$ is

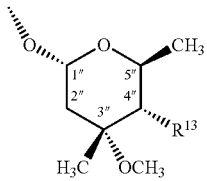

A representative example of $R^2$ is hydrogen.

Representative examples of $R^3$ include hydrogen and $C_{1-4}$alkyl, such as hydrogen and methyl, for example hydrogen.

In one embodiment, $R^4$ and $R^5$ are hydroxy, or $R^4$ and $R^5$ taken together with the intervening atoms form a cyclic group having the following structure:

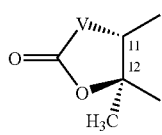

wherein V is a bivalent radical selected from —CH$_2$—, —CH(CN)—, —O—, —N($R^{17}$)— or —CH(S$R^{17}$)—. In a further embodiment, $R^4$ and $R^5$ are hydroxy.

A representative example of $R^6$ is hydrogen.

A representative example of $R^7$ is $C_{1-4}$alkyl, for example methyl.

In one embodiment, $R^{11}$ and $R^{12}$ are each independently hydrogen or $C_{1-6}$alkyl. In a further embodiment, one of $R^{11}$ and $R^{12}$ is hydrogen and the other is methyl.

In one embodiment, $R^{13}$ is —OC(O)(CH$_2$)$_d$U$^1R^{14}$, —O(CH$_2$)$_d$U$^1R^{14}$.

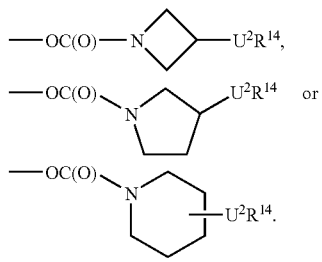

Representative examples of $R^{13}$ include —OC(O)(CH$_2$)$_d$U$^1R^{14}$ and —O(CH$_2$)$_d$U$^1R^4$, for example —OC(O)(CH$_2$)$_d$U$^1R^{14}$.

Representative examples of $R^{14}$ include a heterocyclic group having the following structure:

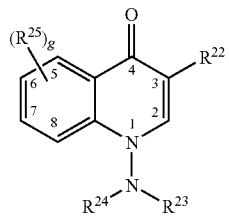

wherein the heterocyclic is linked in the 6 or 7 position, for example the 6 position, to the U$^1$ or U$^2$ group as above defined;

a heterocyclic group having the following structure:

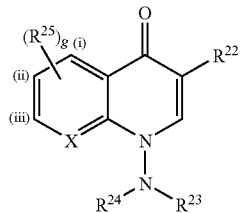

wherein X is —C($R^{41}$)— where $R^{41}$ and $R^{24}$ are linked to form a cyclic group of formula (IF), and said heterocyclic is linked in the (ii) or (iii) position, for example the (ii) position, to the U$^1$ or U$^2$ group as above defined;

a heterocyclic group having the following structure:

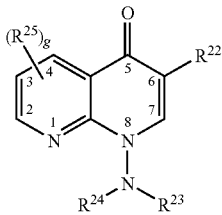

said heterocyclic is linked in the 2 or 3 position, for example the 6 position, to the $U^1$ or $U^2$ group as above defined; and a heterocyclic group having the following structure:

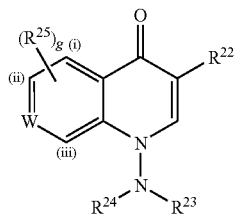

wherein said heterocyclic is linked in the (ii) position to the $U^1$ or $U^2$ group as above defined.

For example, $R^{14}$ is a heterocyclic group having the following structure:

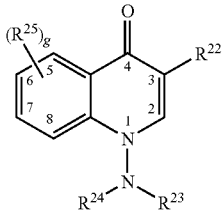

wherein the heterocyclic is linked in the 6 or 7 position, for example the 6 position, to the $U^1$ or $U^2$ group as above defined.

An alternative example of $R^{14}$ is a heterocyclic group having the following structure:

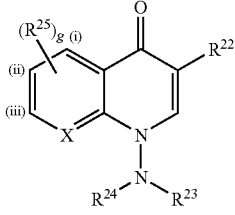

wherein $R^{23}$ is $C_{1-4}$ alkyl, X is $—C(R^{41})—$ where $R^{41}$ and $R^{24}$ are linked to form a cyclic group of formula (IF-a), and said heterocyclic is linked in the (ii) or (iii) position, for example the (ii) position, to the $U^1$ or $U^2$ group as above defined.

In one embodiment, $R^{15}$ is hydrogen.

A representative example of $R^{17}$ is hydrogen.

Representative examples of $R^{21}$ include hydrogen and $C_{1-4}$alkyl optionally substituted by $—OR^{32}$, for example hydrogen and methyl optionally substituted by $—OR^{32}$.

In one embodiment, $R^{22}$ is hydrogen, $—C(O)OR^{34}$, $—C(O)NHR^{34}$ or $—C(O)CH_2NO_2$. In a further embodiment, $R^{22}$ is $—C(O)OR^{34}$, $—C(O)NHR^{34}$ or $—C(O)CH_2NO_2$. A representative example of $R^{22}$ is $—C(O)OR^{34}$.

In one embodiment, $R^{23}$ and $R^{24}$ are each independently hydrogen or $C_{1-4}$alkyl, for example $R^{23}$ is hydrogen and $R^{24}$ is methyl or $R^{23}$ and $R^{24}$ are each methyl. In another embodiment, $R^{23}$ and $R^{24}$, together with the nitrogen atom to which they are bound, form a five- to six-membered heterocyclic ring optionally containing one additional heteroatom selected from oxygen, sulfur and N—$R^{37}$, for example a six membered ring containing one additional heteroatom selected from oxygen, sulfur and N—$R^{37}$ such as morpholino. In a further embodiment, $R^{23}$ is $C_{1-4}$alkyl, X is $—C(R^{41})—$, and $R^{24}$ and $R^{41}$ are linked to form a cyclic group of formula (IF).

In one embodiment, $R^{25}$ is halogen.

A representative example of $R^{32}$ is $C_{1-4}$alkyl, for example methyl.

A representative example of $R^{34}$ is hydrogen.

Representative examples of $R^{40}$ include hydrogen and $C_{1-4}$alkyl, such as hydrogen and methyl, for example hydrogen.

Representative examples of $R^{41}$ include hydrogen, and, when X is $—C(R^{41})—$, $R^{41}$ and $R^{24}$ being linked to form a cyclic group of formula (IF).

Representative examples of $U^1$ include $—Y(CH_2)_rZ—$ and $—Y(CH_2)_r—$, for example $—Y(CH_2)_r—$.

Representative examples of V include $—O—$ and $—N(R^{17})—$.

In one embodiment, W and X are each $—C(R^{41})—$, W is $—C(R^{41})—$ and X is nitrogen or W is nitrogen and X is $—C(R^{41})—$.

Representative examples of W include $—CH—$ and nitrogen.

Representative examples of X include $—CH—$, nitrogen and $—C(R^{41})—$ where $R^{41}$ and $R^{24}$ are linked to form a cyclic group of formula (IF).

Representative examples of Y include $—N(R^{40})—$ and $—O—$.

Representative examples of Z include $—O—$ and $—S—$.

Representative examples of d include 2 and 3, for example 2.

A representative example of g is 0.

Representative examples of r include 2 and 3, for example 3.

A representative example of s is 0.

In one aspect the invention provides a compound of formula (I) wherein $R^1$ represents:

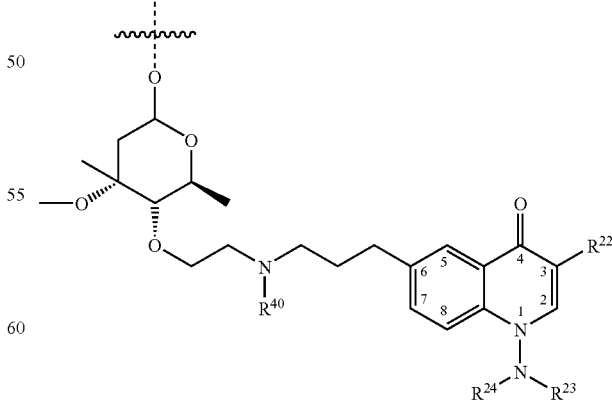

In this aspect $R^2$ may, for example, represent H.

In this aspect $R^3$ may, for example, represent $C_{1-4}$alkyl such as methyl.

In this aspect $R^4$ may, for example, represent hydroxy.
In this aspect $R^5$ may, for example, represent hydroxy.
In this aspect $R^6$ may, for example, represent H.

It is to be understood that the present invention covers all combinations of the embodiments and representative examples described hereinabove. It is also to be understood that the present invention encompasses compounds of formula (I) in which a particular group or parameter, for example $R^7$, $R^{18}$, $R^{19}$, $R^{20}$, $R^{25}$, $R^{26}$, $R^{27}$, $R^{28}$, $R^{29}$, $R^{30}$, $R^{31}$, $R^{32}$, $R^{33}$, $R^{35}$, $R^{36}$, $R^{37}$, $R^{38}$, $R^{39}$, $R^{40}$, $R^{41}$, h, i, j, k, m, n, p and s may occur more than once. In such compounds it will be appreciated that each group or parameter is independently selected from the values listed.

Compounds of the invention include:

4"-O-{3-[3-(3-Carboxy-1,4-dihydro-1-dimethylamino-4-oxo-6-quinolinyl)propylamino]propionyl}-6-O-methyl-erythromycin A, 4"-O-{3-[3-(3-Carboxy-1,4-dihydro-1-dimethylamino-4-oxo-7-quinolinyl)propylamino]propionyl}-azithromycin-11,12-carbonate, 4"-O-{3-[3-(3-Carboxy-1,4-dihydro-1-(morpholin-4-yl)-4-oxo-6-quinolinyl)propylamino]propionyl}-6-O-methyl-erythromycin A, 4"-O-{3-[3-(3-Carboxy-1,4-dihydro-1-methylamino-4-oxo-6-quinolinyl)propylamino]propionyl}-6-O-methylerythromycin A, 4"-O-{3-[3-(3-Carboxy-1,4-dihydro-1-dimethylamino-4-oxo-6-quinolinyl)propylamino]propionyl}-erythromycin A (9E)-oxime, 4"-O-{3-[3-(3-Carboxy-1,4-dihydro-1-dimethylamino-4-oxo-6-quinolinyl)propylamino]propionyl}-erythromycin A (9E)-methoxime, 4"-O-[3-[3-(3-Carboxy-1-(N,N-dimethylamino)-1,4-dihydro-4-oxo-6-quinolinyl) propylaminopropionyl]-6-O-methyl erythromycin A (9E)-oxime, 4"-O-{3-[3-(3-Carboxy-1,4-dihydro-1-dimethylamino-4-oxo-6-quinolinyl)propylamino]propionyl}-6-O-methyl-erythromycin A lactobionate salt, 4"-O-{3-[3-(3-Carboxy-1,4-dihydro-1-dimethylamino-4-oxo-6-quinolinyl)propylamino]propionyl}-6-O-methyl-erythromycin A citrate salt, 4"-O-{3-[2-(3-Carboxy-1,4-dihydro-1-dimethylamino-4-oxo-[1,7]naphthyridin-6-ylsulfanyl)-ethylamino]propionyl}-6-O-methyl-erythromycin A, 4"-O-{3-[2-(3-Carboxy-1,4-dihydro-1-dimethylamino-4-oxo-7-quinolinyl)oxyethylamino]propionyl}-6-O-methylerythromycin A, 4"-O-{3-[2-(3-Carboxy-1,4-dihydro-1-dimethylamino-4-oxo-7-quinolinyl)oxyethylamino]propionyl}-azithromycin, 4"-O-{3-[2-(3-Carboxy-1,4-dihydro-1-dimethylamino-4-oxo-7-quinolinyl)oxyethylamino]propionyl}-erythromycin A (9E)-oxime, 4"-O-{3-[3-(3-Carboxy-1,4-dihydro-1-dimethylamino-4-oxo-6-quinolinyl)propylamino]propionyl}-azithromycin, 4"-O-{3-[3-(6-Carboxy-2,3-dihydro-3-methyl-7-oxo-7H-[1,3,4]oxadiazino[6,5,4-ij]quinolin-9-yl)propylamino]propionyl}-6-O-methyl erythromycin A 4"-O-{3-[3-(6-Carboxy-2,3-dihydro-3-methyl-7-oxo-7H-[1,3,4]oxadiazino[6,5,4-ij]quinolin-9-yl)propylamino]propionyl}-erythromycin A-(9E)-O-methoxymethyloxime, 4"-O-{3-[[3-(3-Carboxy-1-dimethylamino-4-oxo-1,4-dihydro-quinolin-6-yl)-propyl]-methylamino]-propyl}-6-O-methyl-11-desoxy-11-(R)-amino-erythromycin A 11,12-carbamate, 4"-O-(2-{2-(3-Carboxy-1-dimethylamino-4-oxo-1,4-dihydro-[1,7]-naphthyridine-6-ylsulfanyl)-ethylamino}-ethyl)-6-O-methyl-erythromycin A 11,12-carbonate, 4"-O-{3-[2-(3-Carboxy-1,4-dihydro-1-(N,N-dimethylamino)-4-oxo-6-quinolinyl)sulfanylethylamino]propionyl}-6-O-methylerythromycin A, 4"-O-{3-[3-(3-Carboxy-1,4-dihydro-1-(N,N-dimethylamino)-4-oxo-6-quinolinyl)propylamino]propionyl}-erythromycin A-(9E)-oxime-11,12-carbonate, 4"-O-{3-[3-(3-Carboxy-1-dimethylamino-4-oxo-1,4-dihydro-quinolin-6-yl)-propoxy]-propyl}-6-O-methyl-erythromycin A, 4"-O-{2-[(2-{[3-Carboxy-1-(dimethylamino)-4-oxo-1,4-dihydro-1,7-naphthyridin-6-yl]thio}ethyl)amino]ethyl}-6-O-methyl-erythromycin A, 4"-O-{2-[(2-{[3-Carboxy-1-(dimethylamino)-4-oxo-1,4-dihydro-7-quinolinyl]oxy}ethyl)amino]ethyl}-6-O-methyl-erythromycin A, 4"-O-{3-[2-{[6-Carboxy-8-(dimethylamino)-5-oxo-5,8-dihydro-1,8-naphthyridin-3-yl]thio}ethylamino]propionyl}-6-O-methylerythromycin A, 4"-O-{3-[3-[6-Carboxy-8-(dimethylamino)-5-oxo-5,8-dihydro-1,8-naphthyridin-3-yl])propylamino]propionyl}-6-O-methylerythromycin A, 4"-O-[3-[3-(3-Carboxy-1-dimethylamino-1,4-dihydro-4-oxo-6-quinolinyl) propylamino]propionylerythromycin A-(9E)-O-methoxymethyloxime, 4"-O-{2-[3-(3-Carboxy-1,4-dihydro-1-dimethylamino-4-oxo-6-quinolinyl)propylamino]ethyl}-6-O-methylerythromycin A, 4"-O-{3-[3-(3-Carboxy-1,4-dihydro-1-dimethylamino-4-oxo-7-quinolinyloxy)propylamino]propionyl}-6-O-methylerythromycin A, 4"-O-{2-[(2-{[3-Carboxy-1-(dimethylamino)-4-oxo-1,4-dihydro-7-quinolinyl]oxy}ethyl)methylamino]ethyl}-6-O-methyl-erythromycin A, 4"-O-{2-[(3-[3-Carboxy-1-(dimethylamino)-4-oxo-1,4-dihydro-6-quinolinyl]propyl)methylamino]ethyl}-6-O-methyl-erythromycin A, 4"-O-{2-[(3-[3-Carboxy-1-(dimethylamino)-4-oxo-1,4-dihydro-6-quinolinyl]propyl)methylamino]ethyl}-6-O-methyl-erythromycin A D-tartrate salt, 4"-O-{2-[(3-[3-Carboxy-1-(dimethylamino)-4-oxo-1,4-dihydro-6-quinolinyl]propyl)methylamino]ethyl}-6-O-methyl-erythromycin A phosphate salt, 4"-O-{2-[(3-[3-Carboxy-1-(dimethylamino)-4-oxo-1,4-dihydro-6-quinolinyl]propyl)methylamino]ethyl}-6-O-methyl-erythromycin A fumarate salt, 4"-O-{2-[(3-[3-Carboxy-1-(morpholin-4-yl)-4-oxo-1,4-dihydro-6-quinolinyl]propyl)amino]ethyl}-6-O-methyl-erythromycin A, 4"-O-{2-[(3-[3-Carboxy-1-(methylamino)-4-oxo-1,4-dihydro-6-quinolinyl]propyl)amino]ethyl}-6-O-methyl-erythromycin A, 4"-O-{2-[(3-[3-Carboxy-1-(dimethylamino)-4-oxo-1,4-dihydro-6-quinolinyl]propyl)methylamino]ethyl}-erythromycin A-(9E)-(cyanomethyl)oxime, 4"-O-{3-[(3-[3-Carboxy-1-(dimethylamino)-4-oxo-1,4-dihydro-6-quinolinyl]propyl)methylamino]propyl}-6-O-methyl-erythromycin A, 4"-O-{2-[3-(3-carboxy-1-dimethylamino-4-oxo-1,4-dihydro-quinolin-6-yl)-propyloxy]-ethylcarbamoyl}-(9E)-O-methyloxime-erythromycin A, 4"-O-{2-[3-(3-carboxy-1-dimethylamino-4-oxo-1,4-dihydro-quinolin-6-yl)-propyloxy]-ethylcarbamoyl}-(9E)-O-methoxymethyloxime-erythromycin A, 4"-O-{2-[3-(3-carboxy-1-dimethylamino-4-oxo-1,4-dihydro-quinolin-6-yl)-propyloxy]-ethylcarbamoyl}-6-O-methyl-erythromycin A, 4"-O-{2-[3-(3-carboxy-1-dimethylamino-4-oxo-1,4-dihydro-quinolin-6-yl)-propyloxy]-ethylcarbamoyl}-9-dihydro-erythromycin-9,11-ethylidene acetal 4"-O-{2-[2-(3-carboxy-1-dimethylamino-4-oxo-1,4-dihydro-quinolyn-6-sulfanyl)-ethoxy]-ethylcarbamoyl}-(9E)-oxime-erythromycin A, 4"-O-{2-[2-(3-carboxy-1-dimethylamino-4-oxo-1,4-dihydro-quinolyn-6-sulfanyl)-ethoxy]-ethylcarbamoyl}-(9E)-oxime-erythromycin A trifluoroacetate salt, 4"-O-{2-[3-(3-carboxy-1-dimethylamino-4-oxo-1,4-dihydro-quinolin-6-yl)-propyloxy]-ethylcarbamoyl}-(9E)-oxime-erythromycin A, 4"-O-{2-[2-(3-carboxy-1-dimethylamino-4-oxo-1,4-dihydro-quinolin-6-ylsulfanyl)-ethoxy]-ethylcarbamoyl}-(9E)-O-methyloxime-erythromycin A, 4"-O-{2-[2-(3-carboxy-1-dimethylamino-4-oxo-1,4-dihydro-quinolin-6-ylsulfanyl)-ethoxy]-ethylcarbamoyl}-(9E)-O-methoxymethyloxime-erythromycin A, 4"-O-{2-[2-(3-carboxy-1-dimethylamino-4-oxo-1,4-dihydro-quinolin-6-ylsulfanyl)-ethoxy]-ethylcarbamoyl}-(9E)-O-methoxymethyloxime-erythromycin A trifluoroacetate salt, 4"-O-{2-[2-(3-carboxy-1-dimethylamino-4-oxo-1,4-dihydro-quinolin-6-sulfanyl)-ethoxy]-ethylcarbamoyl}-(9E)-O-(2-diethylaminoethyl)-oxime-erythromycin A, 4"-O-{2-[3-(3-carboxy-1-dimethylamino-4-oxo-1,4-dihydro-quinolin-6-yl)-propyloxy]-ethylcarbamoyl}-(9E)-O-(cyanomethyl)oxime-erythromycin A, 4"-O-{2-[3-(3-carboxy-1-dimethylamino-4-oxo-1,4-dihydro-quinolin-6-yl)-propyloxy]-ethylcarbamoyl}-(9E)-O-(methoxycarbonylmethyl)oxime-erythromycin A, 4"-O-{2-[3-(3-carboxy-1-dimethylamino-4-oxo-1,4-dihydro-quinolin-6-yl)-propyloxy]-ethylcarbamoyl}-9-O-(2-diethylaminoethyl)-oxime-erythromycin A, 4"-O-{3-[[3-(3-Carboxy-1,4-dihydro-1-dimethylamino-4-oxo-6-quinolinyl)propyl]-methylamino]propionyl}-6-O-methylerythromycin A, 4"-O-{2-[[3-(3-Carboxy-1,4-dihydro-1-dimethylamino-4-oxo-6-quinolinyl)propyl]-cyclopropylamino]ethyl}-azithromycin, 4"-O-{2-[3-(3-Carboxy-1,4-dihydro-1-dimethylamino-4-oxo-6-quinolinyl)propyl]-oxyethyl}-azithromycin, 4"-O-{3-[3-(3-Carboxy-1-(N,N-dimethylamino)-1,4-dihydro-4-oxo-6-quinolinyl) propylamino]propionyl}-erythromycin A (9E)-2-(diethylamino)ethyloxime, 4"-O-{3-[2-(3-Carboxy-1-(N,N-dimethylamino)-1,4-dihydro-4-oxo-7-quinolinyl)oxyethylamino]propionyl}-erythromycin A (9E)-2-(diethylamino)ethyloxime, 4"-O-{3-[2-{[6-Carboxy-8-(dimethylamino)-5-oxo-5,8-dihydro-1,8-naphthyridin-3-yl]thio}ethylamino]propionyl}-erythromycin A (9E)-2-(diethylamino)ethyloxime, 4"-O-{3-[3-[6-Carboxy-8-(dimethylamino)-5-oxo-5,8-dihydro-1,8-naphthyridin-3-yl])propylamino]propionyl}-erythromycin A (9E)-2-(diethylamino)ethyloxime, 4"-O-{3-[3-(3-Carboxy-1-(N,N-dimethylamino)-1,4-dihydro-4-oxo-6-quinolinyl) propylamino]propionyl}-erythromycin A (9E)-2-(N-morpholinyl)ethyloxime, and 4"-O-{2-[[3-(3-Carboxy-1-(N,N-dimethylamino)-1,4-dihydro-4-oxo-6-quinolinyl) propyl]methylamino]ethyl}-azithromycin;

or a pharmaceutically acceptable derivative thereof.

Particular compounds of the invention include:

4"-O-{3-[3-(3-carboxy-1,4-dihydro-1-dimethylamino-4-oxo-6-quinolinyl)propylamino]propionyl}-6-O-methyl-erythromycin A; and 4"-O-{3-[2-(3-carboxy-1,4-dihydro-1-(N,N-dimethylamino)-4-oxo-6-quinolinyl)sulfanylethylamino]propionyl}-6-O-methylerythromycin A;

or a pharmaceutically acceptable derivative thereof.

Compounds according to the invention may exhibit a broad spectrum of antimicrobial activity, in particular antibacterial activity, against a wide range of clinical pathogenic microorganisms. Using a standard microtiter broth serial dilution test, compounds of the invention have been found to exhibit useful levels of activity against a range of pathogenic microorganisms, for example gram positive bacteria. The compounds of the invention may be active against strains which include *Staphylococcus aureus, Streptopococcus pneumoniae, Moraxella catarrhalis, Streptococcus pyogenes, Haemophilus influenzae, Enterococcus faecalis, Chlamydia pneumoniae, Mycoplasma pneumoniae* and *Legionella pneumophila*. The compounds of the invention may also be active against resistant strains, for example erythromycin resistant strains. Thus, for example, the compounds of the invention may be active against erythromycin resistant strains of *Streptococcus pneumoniae, Streptococcus pyogenes* and *Staphylococcus aureus*.

The compounds of the invention may therefore be useful for treating a variety of diseases caused by pathogenic microorganisms, in particular bacteria, in human beings and animals. It will be appreciated that reference to treatment includes acute treatment or prophylaxis as well as the alleviation of established symptoms.

Furthermore, one or more of the compounds of formula (I) are believed to have improved bioavailability and/or pKa in comparison to typical pleuromutilin derived compounds. Thus these one or more compounds may be particularly suited to oral administration. Furthermore, the compounds of the present invention may have better physical properties such as crystallinity than other known pleuromutilin derivatives.

The compounds of the invention may also be more efficacious, show greater selectivity, have fewer side effects, have a longer duration of action, be more bioavailable by the preferred route, have more suitable pharmacodynamic or pharmacokinetic properties, or have other more desirable properties than similar known compounds.

Thus, according to another aspect of the present invention we provide a compound of formula (I) or a pharmaceutically acceptable derivative thereof for use in therapy.

According to a further aspect of the invention we provide a compound of formula (I) or a pharmaceutically acceptable derivative thereof for use in the treatment or prophylaxis of systemic or topical microbial infections in a human or animal body.

According to a further aspect of the invention we provide the use of a compound of formula (I) or a pharmaceutically acceptable derivative thereof in the manufacture of a medicament for use in the treatment or prophylaxis of systemic or topical microbial infections in a human or animal body.

According to a yet further aspect of the invention we provide a method of treatment of the human or non-human animal body to combat microbial infections comprising administration to a body in need of such treatment of an effective amount of a compound of formula (I) or a pharmaceutically acceptable derivative thereof.

While it is possible that, for use in therapy, a compound of the invention may be administered as the raw chemical it is preferable to present the active ingredient as a pharmaceutical formulation eg when the agent is in admixture with a suitable pharmaceutical excipient, diluent or carrier selected with regard to the intended route of administration and standard pharmaceutical practice.

Accordingly, in one aspect, the present invention provides a pharmaceutical composition or formulation comprising a compound of the invention or a pharmaceutically acceptable derivative thereof in association with a pharmaceutically acceptable excipient, diluent and/or carrier. The excipient, diluent and/or carrier must be "acceptable" in the sense of being compatible with the other ingredients of the formulation and not deleterious to the recipient thereof.

In another aspect, the invention provides a pharmaceutical composition comprising, as active ingredient, a compound of the invention or a pharmaceutically acceptable derivative thereof in association with a pharmaceutically acceptable excipient, diluent and/or carrier for use in therapy, and in particular, in the treatment of human or animal subjects suffering from a condition susceptible to amelioration by an antimicrobial compound.

In another aspect, the invention provides a pharmaceutical composition comprising a therapeutically effective amount of the compounds of the present invention and a pharmaceutically acceptable excipient, diluent and/or carrier (including combinations thereof).

There is further provided by the present invention a process of preparing a pharmaceutical composition, which process comprises mixing a compound of the invention or a pharmaceutically acceptable derivative thereof, together with a pharmaceutically acceptable excipient, diluent and/or carrier.

The compounds of the invention may be formulated for administration in any convenient way for use in human or veterinary medicine and the invention therefore includes within its scope pharmaceutical compositions comprising a compound of the invention adapted for use in human or veterinary medicine. Such compositions may be presented for use in a conventional manner with the aid of one or more suitable excipients, diluents and/or carriers. Acceptable excipients, diluents and carriers for therapeutic use are well known in the pharmaceutical art, and are described, for example, in Remington's Pharmaceutical Sciences, Mack Publishing Co. (A. R. Gennaro edit. 1985). The choice of pharmaceutical excipient, diluent and/or carrier can be selected with regard to the intended route of administration and standard pharmaceutical practice. The pharmaceutical compositions may comprise as—or in addition to—the excipient, diluent and/or carrier any suitable binder(s), lubricant(s), suspending agent(s), coating agent(s), solubilising agent(s).

Preservatives, stabilisers, dyes and even flavouring agents may be provided in the pharmaceutical composition. Examples of preservatives include sodium benzoate, sorbic acid and esters of p-hydroxybenzoic acid. Antioxidants and suspending agents may be also used.

For some embodiments, the agents of the present invention may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO 91/11172, WO 94/02518 and WO 98/55148.

The compounds of the invention may be milled using known milling procedures such as wet milling to obtain a particle size appropriate for tablet formation and for other formulation types. Finely divided (nanoparticulate) preparations of the compounds of the invention may be prepared by processes known in the art, for example see International Patent Application No. WO 02/00196 (SmithKline Beecham).

The routes for administration (delivery) include, but are not limited to, one or more of: oral (e.g. as a tablet, capsule, or as an ingestable solution), topical, mucosal (e.g. as a nasal spray or aerosol for inhalation), nasal, parenteral (e.g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, epidural and sublingual.

There may be different composition/formulation requirements depending on the different delivery systems. By way of example, the pharmaceutical composition of the present invention may be formulated to be delivered using a mini-pump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be delivered by both routes.

Where the agent is to be delivered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

It is to be understood that not all of the compounds need be administered by the same route. Likewise, if the composition comprises more than one active component, then those components may be administered by different routes.

The compositions of the invention include those in a form especially formulated for parenteral, oral, buccal, rectal, topical, implant, ophthalmic, nasal or genito-urinary use. For some applications, the agents of the present invention are delivered systemically (such as orally, buccally, sublingually), more preferably orally. Hence, preferably the agent is in a form that is suitable for oral delivery.

If the compound of the present invention is administered parenterally, then examples of such administration include one or more of: intravenously, intraarterially, intraperitoneally, intrathecally, intraventricularly, intraurethrally, intrasternally, intracranially, intramuscularly or subcutaneously administering the agent, and/or by using infusion techniques.

For parenteral administration, the compound is best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

The compounds according to the invention may be formulated for use in human or veterinary medicine by injection (e.g. by intravenous bolus injection or infusion or via intramuscular, subcutaneous or intrathecal routes) and may be presented in unit dose form, in ampoules, or other unit-dose containers, or in multi-dose containers, if necessary with an added preservative. The compositions for injection may be in the form of suspensions, solutions, or emulsions, in oily or aqueous vehicles, and may contain formulatory agents such as suspending, stabilising, solubilising and/or dispersing agents. Alternatively the active ingredient may be in sterile powder form for reconstitution with a suitable vehicle, e.g. sterile, pyrogen-free water, before use.

The compounds of the invention can be administered (e.g. orally or topically) in the form of tablets, capsules, ovules, elixirs, solutions or suspensions, which may contain flavouring or colouring agents, for immediate-, delayed-, modified-, sustained-, pulsed- or controlled-release applications.

The compounds of the invention may also be presented for human or veterinary use in a form suitable for oral or buccal administration, for example in the form of solutions, gels, syrups, mouth washes or suspensions, or a dry powder for constitution with water or other suitable vehicle before use, optionally with flavouring and colouring agents. Solid compositions such as tablets, capsules, lozenges, pastilles, pills, boluses, powder, pastes, granules, bullets or premix preparations may also be used. Solid and liquid compositions for oral use may be prepared according to methods well known in the art. Such compositions may also contain one or more pharmaceutically acceptable carriers and excipients which may be in solid or liquid form.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia.

Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavouring agents, colouring matter or dyes, with emulsifying and/or suspending agents and with diluents such as water, ethanol, propylene glycol and glycerin, and combinations thereof.

The compounds of the invention may also be administered orally in veterinary medicine in the form of a liquid drench such as a solution, suspension or dispersion of the active ingredient together with a pharmaceutically acceptable carrier or excipient.

The compounds of the invention may also, for example, be formulated as suppositories e.g. containing conventional suppository bases for use in human or veterinary medicine or as pessaries e.g. containing conventional pessary bases.

The compounds according to the invention may be formulated for topical administration, for use in human and veterinary medicine, in the form of ointments, creams, gels, hydrogels, lotions, solutions, shampoos, powders (including spray or dusting powders), pessaries, tampons, sprays, dips, aerosols, drops (e.g. eye ear or nose drops) or pour-ons.

For application topically to the skin, the agent of the present invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water.

Alternatively, it can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The compounds may also be dermally or transdermally administered, for example, by use of a skin patch.

For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

As indicated, the compound of the present invention can be administered intranasally or by inhalation and is conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134AT™) or 1,1,1,2,3,3,3-heptafluoropropane (HFA 227EA), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate.

Capsules and cartridges (made, for example, from gelatin) for use in an inhaler or insufflator may be formulated to contain a powder mix of the compound and a suitable powder base such as lactose or starch.

For topical administration by inhalation the compounds according to the invention may be delivered for use in human or veterinary medicine via a nebuliser.

The compounds of the invention may also be used in combination with other therapeutic agents. The invention thus provides, in a further aspect, a combination comprising a compound of the invention or a pharmaceutically acceptable derivative thereof together with a further therapeutic agent.

When a compound of the invention or a pharmaceutically acceptable derivative thereof is used in combination with a second therapeutic agent active against the same disease state the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician or veterinarian. The compounds of the present invention may for example be used for topical administration with other active ingredients such as corticosteroids or antifungals as appropriate.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations by any convenient route.

When administration is sequential, either the compound of the invention or the second therapeutic agent may be administered first. When administration is simultaneous, the combination may be administered either in the same or different pharmaceutical composition.

When combined in the same formulation it will be appreciated that the two compounds must be stable and compatible with each other and the other components of the formulation. When formulated separately they may be provided in any convenient formulation, conveniently in such manner as are known for such compounds in the art.

The compositions may contain from 0.01-99% of the active material. For topical administration, for example, the composition will generally contain from 0.01-10%, more preferably 0.01-1% of the active material.

Typically, a physician will determine the actual dosage which will be most suitable for an individual subject. The specific dose level and frequency of dosage for any particular individual may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

For oral and parenteral administration to humans, the daily dosage level of the agent may be in single or divided doses.

For systemic administration the daily dose as employed for adult human treatment it will range from 2-100 mg/kg body weight, preferably 5-60 mg/kg body weight, which may be administered in 1 to 4 daily doses, for example, depending on the route of administration and the condition of the patient. When the composition comprises dosage units, each unit will preferably contain 200 mg to 1 g of active ingredient. The duration of treatment will be dictated by the rate of response rather than by arbitrary numbers of days.

Compounds of general formula (I) and pharmaceutically acceptable derivatives thereof may be prepared by the general methods outlined hereinafter, said methods constituting a further aspect of the invention. In the following description, the groups $R^1$ to $R^{41}$, U, V, W, X, Y, Z, d, e, f, g, h, i, j, k, m, n, p, q, r and s have the meaning defined for the compounds of formula (I) unless otherwise stated.

The groups $U^{1z}R^{14z}$, $U^{2z}R^{14z}$, $Z^zR^{14z}$ and $R^{14z}$ are $U^1R^{14}$, $U^2R^{14}$, $ZR^{14}$ and $R^{14}$ as defined for formula (I) or groups convertible to $U^1R^{14}$, $U^2R^{14}$, $ZR^{14}$ and $R^{14}$. Conversion of a group $U^{1z}R^{14z}$, $U^{2z}R^{14z}$, $Z^zR^{14z}$ or $R^{14z}$ to a $U^1R^{14}$, $U^2R^{14}$, $ZR^{14}$ or R group typically arises if a protecting group is needed during the reactions described below. A comprehensive discussion of the ways in which such groups may be protected and methods for cleaving the resulting protected derivatives is given by for example T. W. Greene and P. G. M Wuts in Protective Groups in Organic Synthesis $2^{nd}$ ed., John Wiley & Son, Inc 1991 and by P. J. Kocienski in Protecting Groups, Georg Thieme Verlag 1994 which are incorporated herein by reference. Examples of suitable amino protecting groups include acyl type protecting groups (e.g. formyl, trifluoroacetyl and acetyl), aromatic urethane type protecting groups (e.g. benzyloxycarbonyl (Cbz) and substituted Cbz, and 9-fluorenylmethoxycarbonyl (Fmoc)), aliphatic urethane protecting groups (e.g. t-butyloxycarbonyl (Boc), isopropyloxycarbonyl and cyclohexyloxycarbonyl) and alkyl type protecting groups (e.g. benzyl, trityl and chlorotrityl). Examples of suitable oxygen protecting groups may include for example alkyl silyl groups, such as trimethylsilyl or tert-butyldimethylsilyl; alkyl ethers such as tetrahydropyranyl or tert-butyl; or esters such as acetate. Hydroxy groups may be protected by reaction of for example acetic anhydride, benzoic anhydride or a trialkylsilyl chloride in an aprotic solvent. Examples of aprotic solvents are dichloromethane, N,N-dimethylformamide, dimethylsulfoxide, tetrahydrofuran and the like.

The compounds of general formula (I) and derivatives thereof may be purified by conventional methods known in the art. For example, the compounds may be purified by HPLC using an aqueous solution of an acid such as formic acid or trifluoroacetic acid with an organic co-solvent such as acetonitrile or methanol.

In one embodiment of the invention, compounds of formula (I) wherein $R^{13}$ is —OC(O)(CH$_2$)$_d$U$^1$R$^{14}$ and d is an integer from 2 to 5 may be prepared by reaction of a 4″ hydroxy compound of formula (II) wherein $R^2$ may be a hydroxy protecting group with a suitable activated and protected derivative of the carboxylic acid (III), followed where necessary by subsequent removal of the hydroxyl protecting group $R^2$ and conversion of the $U^{1z}R^{14z}$ group to $U^1R^{14}$

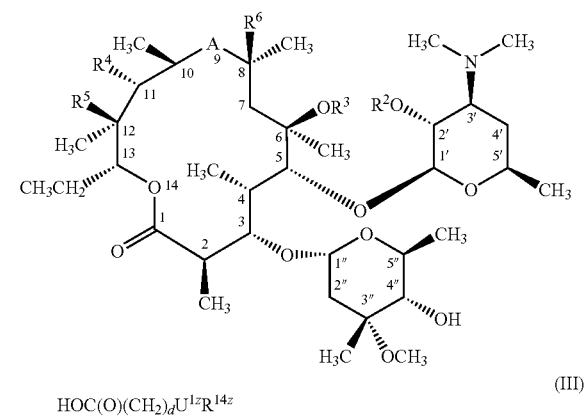

Compounds of formula (I) wherein $R^{13}$ is —NHC(O)(CH$_2$)$_d$U$^1$R$^{14}$ and d is an integer from 2 to 5 may be prepared by reaction of a 4″ amine compound of formula (IIA) with a carboxylic acid compound of formula (IIIA), or a suitable activated and protected derivative thereof, followed where necessary by subsequent conversion of the $U^{1z}R^{14z}$ group to $U^1R^{14}$.

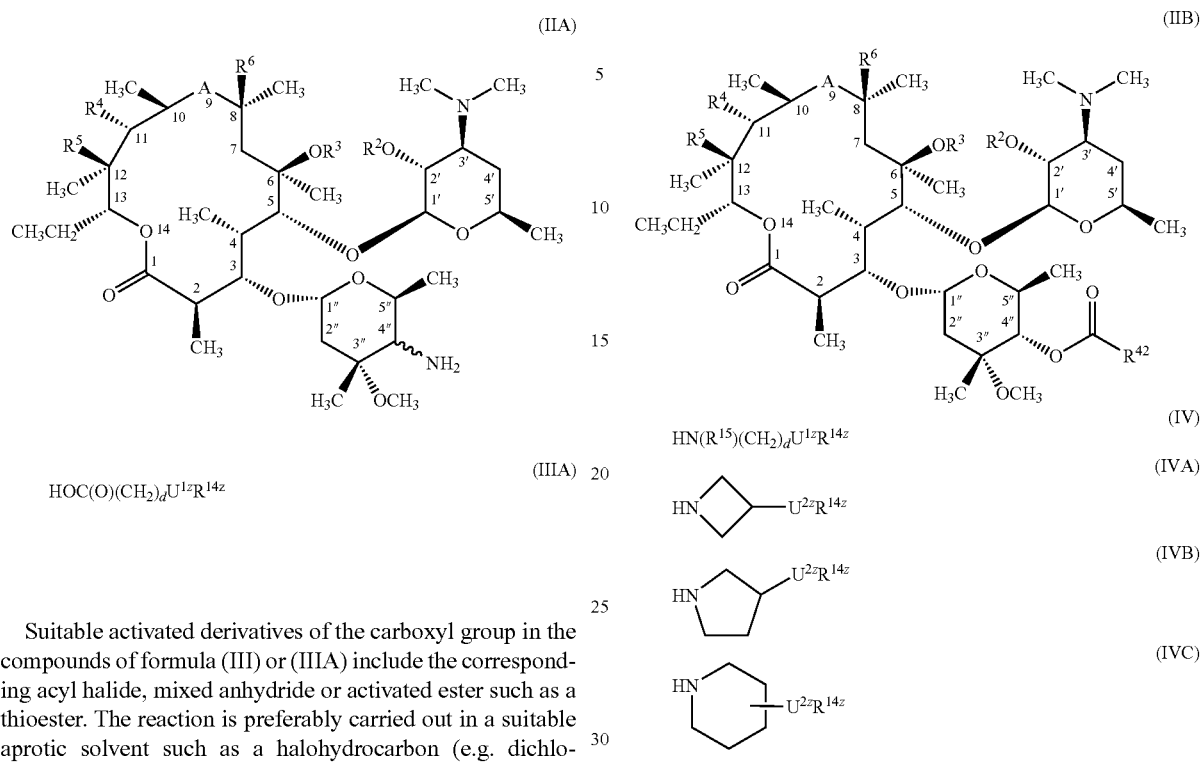

Suitable activated derivatives of the carboxyl group in the compounds of formula (III) or (IIIA) include the corresponding acyl halide, mixed anhydride or activated ester such as a thioester. The reaction is preferably carried out in a suitable aprotic solvent such as a halohydrocarbon (e.g. dichloromethane) or N,N-dimethylformamide optionally in the presence of a tertiary organic base such as dimethylaminopyridine or triethylamine or in the presence of inorganic base (eg sodium hydroxide) and at a temperature within the range of 0° to 120° C. The compounds of formula (II) or (IIA) and (III) or (IIIA) may also be reacted in the presence of a carbodiimide such as dicyclohexylcarbodiimide (DCC).

In another embodiment of the invention, compounds of formula (I) wherein $R^{13}$ is —OC(O)N($R^{15}$)(CH$_2$)$_d$U$^1$R$^{14}$,

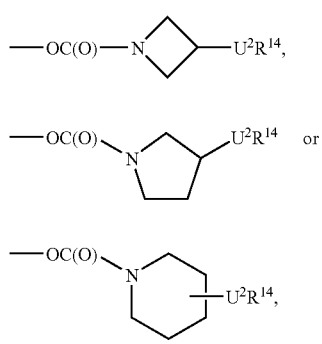

may be prepared by reaction of a suitable activated compound of formula (IIB) wherein $R^2$ is optionally a hydroxy protecting group and $R^{42}$ is an activating group such as imidazolyl or halogen, with a suitable protected derivative of an amine (IV), (IVA), (IVB) or (IVC), followed where necessary by subsequent removal of the hydroxyl protecting group $R^2$ and conversion of the $U^{1z}R^{14z}$ or $U^{2z}R^{14z}$ group to $U^1R^{14}$ or $U^2R^{14}$.

The reaction is preferably carried out in a suitable aprotic solvent such as N,N-dimethylformamide in the presence of an organic base such as 1,8-diazabiyclo[5.4.0]undec-7-ene (DBU).

In another embodiment of the invention, compounds of formula (I) wherein $R^{13}$ is —O(CH$_2$)$_d$U$^1$R$^{14}$, $U^1$ is —Y(CH$_2$)$_r$Z— or —Y(CH$_2$)$_r$—, and Y is —N($R^{40}$)— may be prepared by reaction of a 4" aldehyde compound of formula (IIC) wherein A, $R^4$ and $R^5$ may be suitably protected and d' is an integer from 1 to 4, with a suitable protected derivative of the amine (V) or (VA), followed where necessary by subsequent removal of the hydroxyl protecting group $R^2$ and conversion of the $Z^zR^{14z}$ or $R^{14z}$ group to $ZR^{14}$ or $R^{14}$.

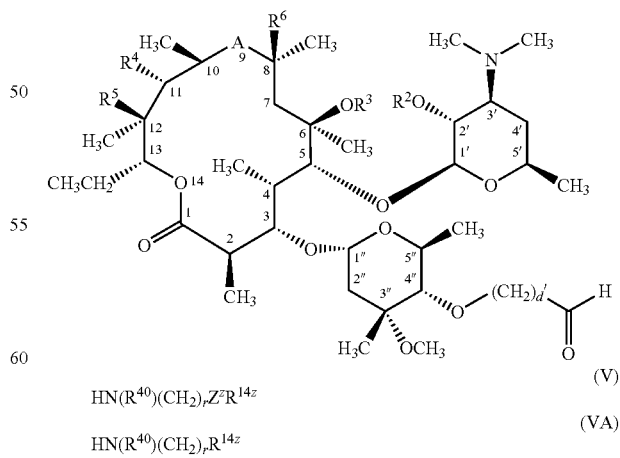

The reductive amination reaction is preferably carried out in a solvent such as methanol and DMF under neutral to mildly acidic conditions. A suitable reducing agent is, for example, sodium cyanoborohydride, and suitable reagents for adjusting acidity are acetic acid and sodium acetate.

Compounds of formula (IIC) where d' is 1 may be prepared from suitably protected compounds of formula (VI) by oxidative cleavage for example using osmium tetroxide and sodium periodate. Where d' is 2, hydroboration of suitably protected compounds of formula (VI) with 9-BBN, or other suitable boranes, followed by treatment with peroxide and then oxidation yields compounds of formula (IIC), d' is 2. For d'=3 or 4, compounds of formula (VI) may be chain extended using olefin cross-metathesis (H. E. Blackwell et. al. J. Am. Chem. Soc., 2000, 122, 58-71) with a suitably functionalised olefin, for example but-2-ene-1,4-diol, followed by double bond reduction and oxidation of the terminal alcohol. Compounds of formula (VI) can be formed by palladium-catalysed allylation of suitably protected 4" hydroxy compounds, for example when A is —C(O)—, by 2',11-bis-silylation and conversion of the 9-ketone to a bicyclic ketal by interaction with the 12-OH and an alcohol, for example methanol.

(VI)

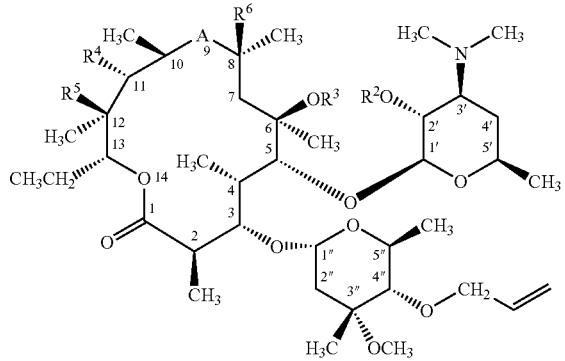

In another embodiment of the invention, compounds of formula (I) wherein $R^{13}$ is —OC(O)(CH$_2$)$_d$U$^1$R$^{14}$, d is an integer from 2 to 5, U$^1$ is —Y(CH$_2$)$_r$Z—, and Y is —N(R$^{40}$)—, —O— or —S—, may be prepared by reaction of compounds of formula (VII)

(VII)

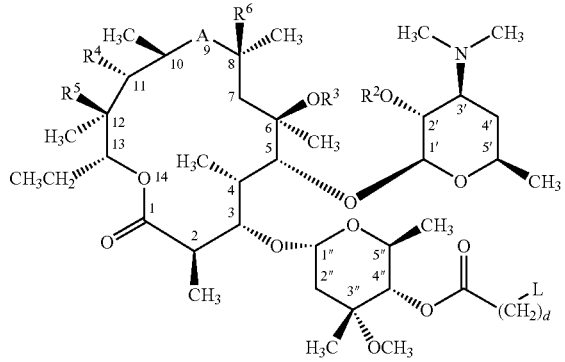

wherein d is an integer from 2 to 5 and L is a suitable leaving group, with HU$^{1z}$R$^{14z}$ (VIII) in which Y is —N(R$^{40}$)—, —O— or —S—.

Similarly, compounds of formula (I) wherein $R^{13}$ is —OC(O)N(R$^{15}$)(CH$_2$)$_d$U$^1$R$^{14}$, U$^1$ is —Y(CH$_2$)$_r$Z— or —Y(CH$_2$)$_r$—, and Y is —N(R$^{40}$)— or —S—, may be prepared by reaction of compounds of formula (VIIA)

(VIIA)

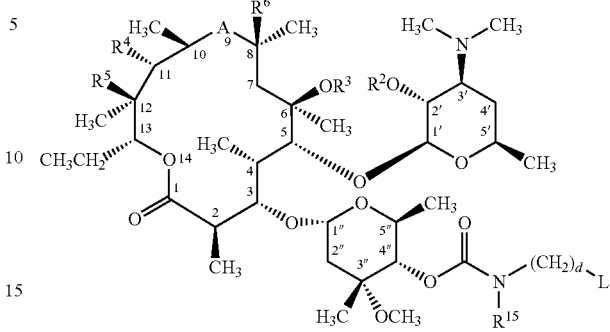

wherein d is an integer from 2 to 5 and L is a suitable leaving group, with HU$^{1z}$R$^{14z}$ (VIII) in which Y is —N(R$^{40}$)— or —S—.

Similarly, compounds of formula (I) wherein $R^{13}$ is —O(CH$_2$)$_d$U$^1$R$^{14}$, U is Y(CH$_2$)$_r$Z or —Y(CH$_2$)$_r$—, and Y is —N(R$^{40}$)— or —S—, may be prepared by reaction of compounds of formula (VIIB)

(VIIB)

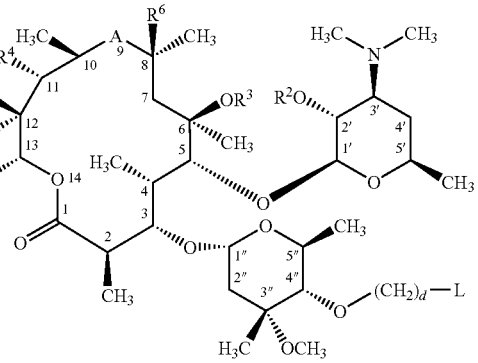

wherein d is an integer from 2 to 5 and L is a suitable leaving group, with HU$^{1z}$R$^{14z}$ (VIII) in which Y is —N(R$^{40}$)— or —S—.

Further, compounds of formula (I) wherein $R^{13}$ is —NHC(O)(CH$_2$)$_d$U$^1$R$^{14}$, d is an integer from 2 to 5, U$^1$ is —Y(CH$_2$)$_r$Z— or —Y(CH$_2$)$_r$—, and Y is —N(R$^{40}$)— or —S—, may be prepared by reaction of compounds of formula (VIIC)

(VIIC)

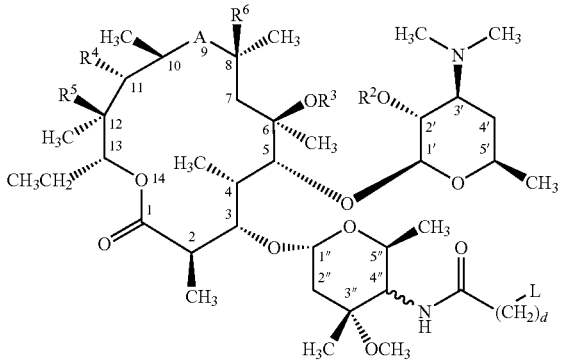

wherein d is an integer from 2 to 5 and L is a suitable leaving group, with $HU^{1z}R^{14z}$ (VIII) in which Y is —$N(R^{40})$— or —S—.

The reaction between (VII), (VIIA), (VIIB) or (VIIC) and (VIII) is preferably carried out in a solvent such as a halohydrocarbon (e.g. dichloromethane), an ether (e.g. tetrahydrofuran or dimethoxyethane), acetonitrile or ethyl acetate and the like, dimethylsulfoxide, N,N-dimethylformamide or 1-methyl-pyrrolidinone and in the presence of a base, followed, if desired, by removal of the hydroxyl protecting group $R^2$ and conversion of the $U^{1z}R^{14z}$ group to $U^1R^{14}$. Examples of the bases which may be used include organic bases such as diisopropylethylamine, triethylamine and 1,8-diazabicyclo[5.4.0]undec-7-ene, and inorganic bases such as potassium hydroxide, cesium hydroxide, tetraalkylammonium hydroxide, sodium hydride and potassium hydride. Suitable leaving groups for this reaction include halide (e.g. chloride, bromide or iodide) or a sulfonyloxy group (e.g. tosyloxy or methanesulfonyloxy).

Compounds of formula (VII) and (VIIC) may be prepared by reaction of a compound of formula (II) or (IIA), wherein $R^2$ is a hydroxyl protecting group, with a suitable activated derivative of the carboxylic acid $HOC(O)(CH_2)_dL$ (IX), wherein L is a suitable leaving group as above defined. Suitable activated derivatives of the carboxyl group are those defined above for carboxylic acids (III) or (IIIA). The reaction is carried out using the conditions described above for the reaction of a compound of formula (II) or (IIA) with carboxylic acid (III) or (IIIA).

In another embodiment of the invention, compounds of formula (I) wherein $R^{13}$ is —$O(CH_2)_dU^1R^{14}$, $U^1$ is —$O(CH_2)_r$ Z— or —$O(CH_2)_r$—, may be prepared by reaction of compounds of formula (X)

(X)

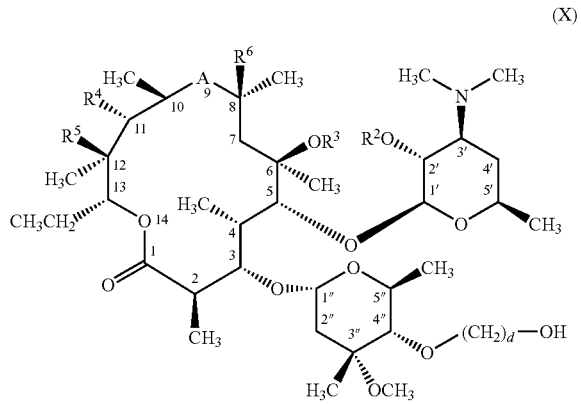

wherein d is an integer from 2 to 5 with a suitable compound of formula $HU^{1z}R^{14z}$ (VII), for example a compound of formula (XI)

(XI)

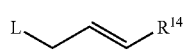

in which L is a suitable leaving group, in the presence of a catalyst such as tetrakis(triphenylphospine) palladium.

In a preferred embodiment of the invention, compounds of formula (I) wherein $R^{13}$ is —$OC(O)(CH_2)_dU^1R^{14}$, d is 2, $U^1$ is as above defined and Y is —$N(R^{40})$— or —S—, may be prepared by Michael reaction of a compound of formula (XII), wherein $R^2$ is optionally a hydroxyl protecting group (XII)

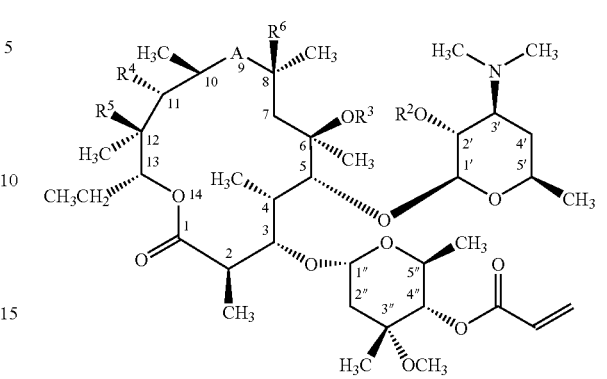

with a compound of formula $HU^{1z}R^{14z}$ (VIII). The reaction is suitably carried out in a solvent such as dimethylsulfoxide, N,N-dimethylformamide, 1-methyl-pyrrolidinone, a halohydrocarbon (e.g. dichloromethane), an ether (e.g. tetrahydrofuran or dimethoxyethane), acetonitrile or alcohol (e.g methanol or isopropanol) and the like, and in the presence of a base, followed, if desired, by removal of hydroxyl protecting group $R^2$ and conversion of the $U^{1z}R^{14z}$ group to $U^1R^4$. Similarly, compounds of formula (I) wherein $R^1$ is —OC(O)$(CH_2)_dU^1R^{14}$, d is 2, $U^1$ is as above defined and Y is —O— may also be prepared by Michael reaction in a solvent such as dimethylsulfoxide, N,N-dimethylformamide, 1-methyl-pyrrolidinone, a halohydrocarbon (e.g. dichloromethane), an ether (e.g. tetrahydrofuran or dimethoxyethane) or acetonitrile, and in the presence of a base.

Compounds of formula (I) may be converted into other compounds of formula (I). Thus compounds of formula (I) wherein Y is —$S(O)_s$— and s is 1 or 2 may be prepared by oxidation of the corresponding compound of formula (I) wherein s is 0. The oxidation is preferably carried out using a peracid, e.g. peroxybenzoic acid, followed by treatment with a phosphine, such as triphenylphosphine. The reaction is suitably carried out in an organic solvent such as methylene chloride. Compounds of formula (I) wherein Y is —$N(R^{40})$— and $R^{40}$ is $C_{1-4}$alkyl can be prepared from compounds wherein $R^{40}$ is hydrogen by reductive alkylation. Compounds of formula (I) wherein Y is —$N(R^{40})$— and $R^{40}$ is acetyl or benzoyl can be prepared from compounds wherein $R^{40}$ is hydrogen by acylation.

Compounds of formula (II), (IIA) and (IIB), wherein A is —C(O)—, —$N(R^7)$—$CH_2$— or —$CH(NR^8R^9)$—, $R^4$ or $R^5$ are hydroxy or $R^4$ and $R^5$ taken together with the intervening atoms form a cyclic group having the following structure:

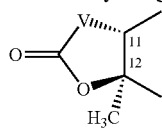

wherein V is a bivalent radical selected from —O— and —$N(R^{17})$—, and $R^3$ is $C_{1-4}$alkyl, or $C_{3-6}$alkenyl optionally substituted by 9- or 10-membered fused bicyclic heteroaryl are known compounds or they may be prepared by analogous methods to those known in the art. Thus they can be prepared according to the procedures described in EP 0 307 177, EP 0 248 279, WO 00/78773 and WO 97/42204.

Compounds of formula (II), (IIA), (IIB) and (IIC) wherein A is —N(CH₃)—CH₂—, R⁴ or R⁵ are hydroxy or R⁴ and R⁵ taken together with the intervening atoms form a cyclic group having the following structure:

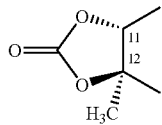

and R⁶ is hydrogen are known compounds or they may be prepared by analogous methods to those known in the art. Thus they can be prepared according to the procedures described in EP 0 508 699, J. Chem. Res. Synop. (1988, pages 152-153) and U.S. Pat. No. 6,262,030.

Compounds of formula (II), (IIA) and (IIB), wherein A is —C(=NR¹⁰)—, R⁴ or R⁵ are hydroxy or R⁴ and R⁵ taken together with the intervening atoms form a cyclic group having the following structure:

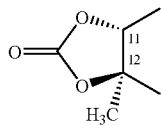

and R⁶ is hydrogen, are known compounds or they may be prepared by analogous methods to those known in the art. Thus they can be prepared according to the procedures described in EP 0 284 203.

Compounds of formula (II), (IIA), (IIB) and (IIC) wherein A is —C(O)—, R⁴ and R⁵ taken together with the intervening atoms form a cyclic group having the following structure:

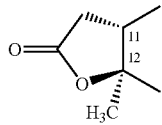

R⁶ is hydrogen and R³ is C₁₋₄alkyl may be prepared by decarboxylation of a compound of formula (XIII), wherein R⁴³ is a hydroxy protecting group followed, if required, by removal of the protecting group R² or R⁴³.

(XIII)

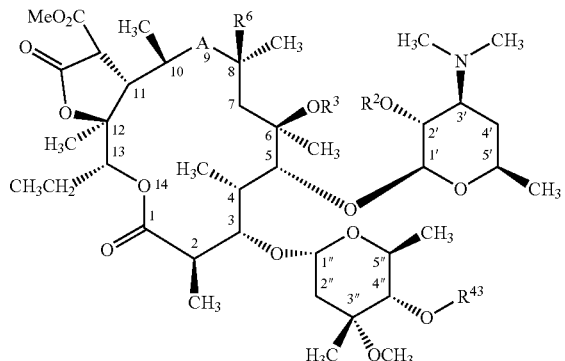

The decarboxylation may be carried out in the presence of a lithium salt such as lithium chloride, preferably in an organic solvent such as dimethylsulfoxide.

Compounds of formula (II), (IIA), (IIB) and (IIC) wherein A is —C(O)—, R⁴ and R⁵ taken together with the intervening atoms form a cyclic group having the following structure:

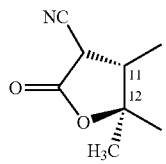

and R³ is C₁₋₄ alkyl may be prepared according to the procedures described in WO 02/50091 and WO 02/50092.

Compounds of formula (III) and (IIIA) wherein U¹ is —Y(CH₂)ᵣN(R⁴⁰)— or —Y(CH₂)ᵣ—, wherein Y is —N(R⁴⁰)—, —O— or —S—, may be prepared by reaction of HU¹ᶻR¹⁴ᶻ (VIII), wherein U¹ᶻ has the meaning defined above with R⁴⁴OC(O)(CH₂)ₐL (XIV) wherein R⁴⁴ is carboxyl protecting group and L is a suitable leaving group, followed by removal of R⁴⁴. Suitable R⁴⁴ carboxyl protecting groups include t-butyl, allyl or benzyl.

Compounds of formula (III) and (IIIA) may also be prepared by reaction of HU¹ᶻR¹⁴ᶻ (VIII) with acrylonitrile followed by hydrolysis of the nitrile to the acid, or by reaction of HU¹ᶻR¹⁴ᶻ (VII) with t-butyl acrylate followed by removal of the t-butyl group.

Compounds of formula (VII) wherein U¹ is —Y(CH₂)ᵣZ— in which Z is —N(R⁴⁰)—, —O— or —S—, may be prepared by reaction of a compound of formula R¹⁴ᶻL (XV), wherein L is a suitable leaving group such as chlorine, fluorine or bromine, with a compound of formula —Y(CH₂)ᵣZ— (XVI) in which Z is —N(R⁴⁰)—, —O— or —S—.

Compounds of formula (I) wherein R¹³ is —O(CH₂)ₐU¹R¹⁴, U¹ is —Y(CH₂)ᵣZ— or —Y(CH₂)ᵣ—, and Y is —C(O)N(R⁴⁰)—, may be prepared by reaction of compounds of formula (XVII)

(XVII)

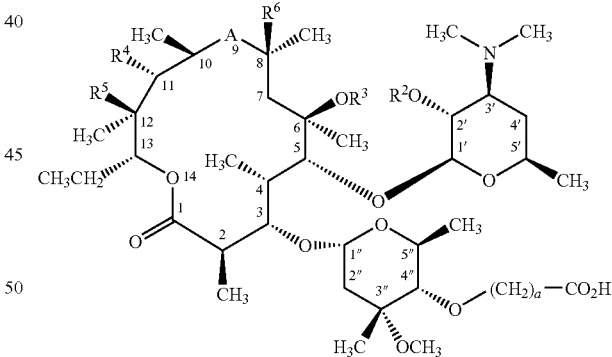

with a suitable amine compound.

Where, R¹⁴ is a heterocyclic group having the following structure:

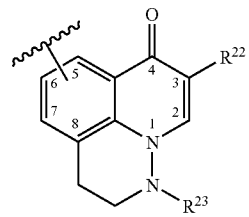

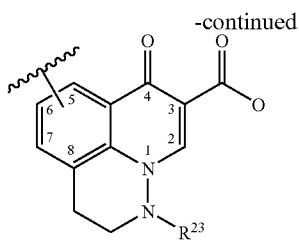

the relevant starting material may be prepared as set out in the reaction scheme below:

General guidance in the preparation of cyclised compounds similar to those shown in the scheme about can be obtained from US patent application publication number 2002/0025959, which will be referred to as '959 hereafter.

Step a may, for example, be performed by N-iodosucinimide in the presence of trifluoromethane sulfonic acid at from 0° C. to room temperature. This process is similar to that described in preparation 19 of '959.

Preparation of the β-ketoester of step b may, for example, be performed by conversion of the acid product of step a to the corresponding imidazole by treatment with 1,1'-carbonyldiimidazole followed by treatment with the trimethylsilyl ester

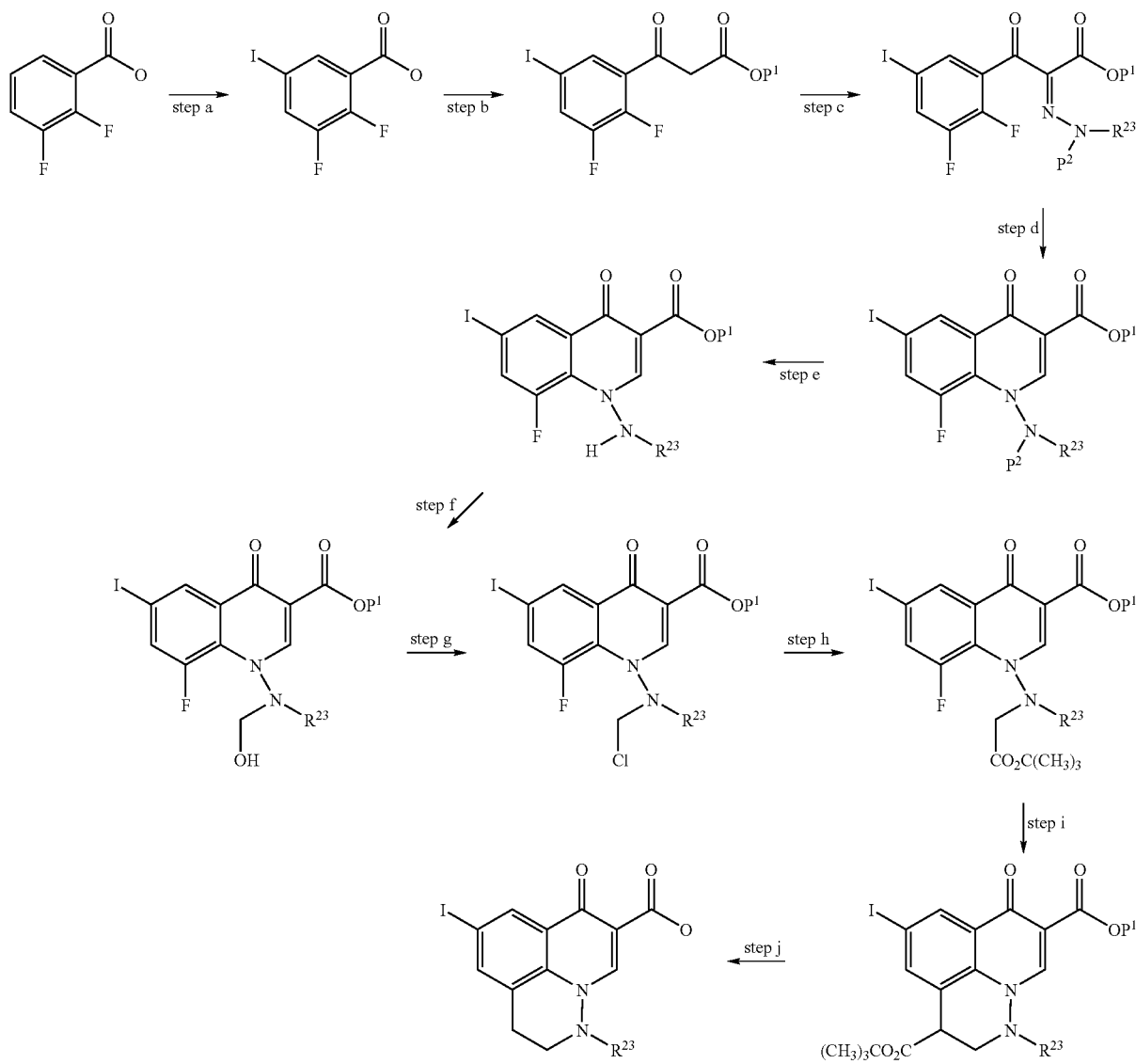

In the above scheme:
$P^1$ represents a carboxylic acid protecting group such as alkyl or benzyl,
$P^2$ represents an amino protecting group such as tert-butyl-dicarbonate (Boc), and
$R^{23}$ represents $C_{1-4}$alkyl.

of ethyl hydrogen malonate in the presence of DBU. This process is similar to that described in preparation 20 in '959.

Step c may be effected by treatment with a Boc-protected hydrazine, for example, tert-butyl 1-methylhydrazinecarboxylate in tert-butanol, at room temperature to 45° C. See preparation 21 and 33 in '959.

The cyclisation of step d may, for example, be performed in the presence of a base, such as, sodium hydride in DMF at room temperature. This process is similar to preparation 34 described in '959.

The deprotection of step e may be performed using common synthetic methods (see Green, T. W. Wutts P. G. M *Protective Groups in Organic Synthesis,* 1999), for example, by treatment with trifluoroacetic acid in DCM (dichloromethane) at room temperature. This process is similar to preparation 35 in '959.

The condensation of Step f may, for example, be performed by treatment with formaldehyde at an elevated temperature such as about 85° C. This process is similar to preparation 36 in '959.

Step g conversion of the hydroxy group to an appropriate leaving group such as chloride may, for example, be performed with thionyl chloride in THF at room temperature. This process is similar to preparation 37a in '959.

Step h, displacement may be performed by treatment with a malonate diester anion, for example, di-tert-butylmalonate anion in THF at 0-5° C. This process is similar to preparation 37b in '959.

The cyclisation of step i may be performed by heating in the presence of an inorganic base, for example, cesium carbonate in DMSO at about 85° C. This process is similar to preparation 38 in '959.

Step j, hydrolysis and decarboxylation may be performed by initially heating in the presence of an acid, for example, acetic acid or trifluoroacetic acid followed by further decarboxylation by heating in DMSO at about 135-165° C. This process is similar to preparation 39 in '959.

The product of step j can be subsequently coupled to the further portion of the molecule by methods analogous to those described above.

The carboxylic acid moiety (which ultimately corresponds to $R^{22}$ in compounds of formula (I)) in the product of step j above can be converted into —C(O)NHR$^{34}$, —C(O)CH$_2$NO$_2$, or —C(O)SO$_2$R$^7$ as required by routine techniques.

All publications, including but not limited to patents and patent applications, cited in this specification are herein incorporated by reference as if each individual publication were specifically and individually indicated to be incorporated by reference herein as though fully set forth.

In order that the invention may be more fully understood the following examples are given by way of illustration only.

The following abbreviations are used in the text: 9-BBN for 9-borabicyclo[3.3.1]nonane, BOC for t-butoxycarbonyl, DBU for 1,8-diazabicyclo[5.4.0]undec-7-ene, DCM for dichloromethane, DMF for N,N-dimethylformamide, DMSO for dimethyl sulfoxide, EtOAc for ethyl acetate, EtOH for ethanol, MeCN for acetonitrile, MeOH for methanol, TFA for trifluoroacetic acid, THF for tetrahydrofuran, MgSO$_4$ for anhydrous magnesium sulphate and Na$_2$SO$_4$ for anhydrous sodium sulphate.

In the procedures that follow, reference to an Intermediate or Example by number is typically provided. This is provided merely for assistance to the skilled chemist to identify the starting material used. The starting material may not necessarily have been prepared from the batch referred to. In addition, the preparation of an Example compound is typically presented as a series of individual reaction steps, for example a), b), c), etc. This is also provided merely for assistance to the skilled chemist to identify a suitable sequence of reaction steps to prepare the Example. Although each of the reaction steps indicated will have been carried out as described, the steps a), b), c), etc. may not have been performed in one continuous sequence from the same batch of starting materials.

In the procedures that follow, reference is made to certain compounds being made "using a similar procedure". As is appreciated by those skilled in the art, such analogous processes may involve variations in synthetic procedure, for example in the solvent(s) used for extraction, or in the eluting solvent system used for chromatographic purification.

EXAMPLES

2'-O-Acetyl-6-O-methyl-erythromycin A may be prepared by the procedure described by W. R. Baker et al. in *J. Org. Chem.* 1988, 53, 2340 and 2'-O-acetyl-azithromycin-11,12-carbonate may be prepared by the procedure described by S. Djokic et al. in *J. Chem. Res. (S)* 1988, 152.

Erythromycin A (9E)-oxime may be prepared by the procedure described by R. R. Wilkening in EP 0 508 726 A1.

Erythromycin A (9E) methoxime may be prepared by the procedure described by J. R. Everett et al. in J. Chem. Soc. Perkin 2, 1989, 11, 1719-1728.

6-O-Methyl erythromycin A (9E)-oxime may be prepared by the procedure described by R. A. Dominguez et al in US 2003023053.

2'-O-acetyl-azithromycin and 2'-O-Acetyl-azithromycin-11,12-carbonate may be prepared by the procedures described by S. Djokic et al. in *J. Chem. Res. (S)* 1988, 152.

2'-O-Acetyl-erythromycin A-(9E)-O-acetyl-oxime may be prepared by the procedure described by J Berge et. al. in WO 2004039822.

2'-O-Acetyl-erythromycin A 11,12-carbonate may be prepared by the procedure described by L. Freidberg et. al. in U.S. Pat. No. 4,686,207A.

Erythromycin A-(9E)-O-methoxymethyloxime may be prepared by the procedure described by Gasc, Jean Claude et al. in *Journal of Antibiotics.,* 1991, 44(3), 313-30.

Erythromycin A (9E)-O-(1-methoxy-1-methylethyl)-oxime may be prepared by the procedure described by S. Morimoto et al. in U.S. Pat. No. 4,990,602.

Erythromycin A (9E)-O-(2-diethylaminoethyl)-oxime may be prepared by the procedure described by S. Gouin d' Ambrieres et al. in U.S. Pat. No. 4,349,545.

(9S)-9-O,11-O-Ethylidene-9-dihydroerythromycin A may be prepared by the procedure described by E. Hunt et al. in *J. Antibiotics,* 1989, 42, 293-298.

Reverse phase HPLC refers to the use of an XTerra MS C18 column with a gradient of MeCN containing 0.1% TFA in water containing 0.1% TFA as eluent.

Mass directed automatic preparative HPLC refers to the use of Waters Atlantis dC18 5 micron columns with a gradient of MeCN containing 0.1% HCO$_2$H in H$_2$O containing 0.1% HCO$_2$H as eluent.

Where Example compounds are isolated as salts, these are typically characterised and the stoichiometry determined using proton NMR, for example by considering the chemical shift values, the integrated number of protons, and by assignment of one or more relevant peak(s) from the acid and from the parent base.

Intermediate 1: 6-(3-Aminopropyl)-1-(dimethylamino)-4-oxo-1,4-dihydro-3-quinolinecarboxylic acid hydrochloride a) Ethyl 3-(dimethylamino)-2-(2-fluoro-5-iodobenzoyl)-2-propenoate A stirred suspension of 2-fluoro-5-iodobenzoic acid (28.1 g) in DCM (300 mL) at 20° C. was treated with oxalyl chlo ride (13.9 mL) and DMF (5 drops). After 3 h the clear solution was evaporated and re-evaporated from toluene (2×) under reduced pressure. The acid chloride was re-dissolved in toluene (500 mL) and treated with triethylamine (22.5 mL) and ethyl 3-(dimethylamino)acrylate (19.95 g). After stirring for 1.5 h at 90° C. the mixture was filtered and the solution flash chromatographed on silica gel eluting with 40 to 70% EtOAc in light petroleum 40-60° C. to give the title compound (30.8 g); APCI m/z 392.1 [M+H]$^+$.

b) Ethyl 3-(2,2-dimethyl hydrazino)-2-(2-fluoro-5-iodobenzoyl)-2-propenoate

A stirred suspension of Intermediate 1a (28.2 g) in EtOH (300 mL) was treated with 1,1-dimethylhydrazine (4.76 mL). After stirring overnight the clear solution was evaporated under reduced pressure to give the title compound (29.6 g); APCI m/z 407.0 [M+H]$^+$.

c) Ethyl 1-(dimethylamino)-6-iodo-4-oxo-1,4-dihydro-3-quinolinecarboxylate

A mixture of Intermediate 1b (28.5 g) and potassium carbonate (14.5 g) in DMF (300 mL) was stirred at 100° C. for 1 h and then cooled to 20° C. The mixture was poured into water, the solid filtered off, washed with water and dried to give the title compound (22.8 g); APCI m/z 387.0 [M+H]$^+$.

d) 1-(Dimethylamino)-6-iodo-4-oxo-1,4-dihydro-3-quinolinecarboxylic acid

Intermediate 1c (12.8 g) was suspended in EtOH (130 mL) and treated with 1N aqueous sodium hydroxide (49.7 mL). The mixture was stirred overnight, diluted with 50% aqueous EtOH (200 mL) and heated at 50° C. for 4 h to complete the hydrolysis. The solution was evaporated under reduced pressure to ca. 200 mL and then acidified. The solid was filtered off, washed with water and dried to give the title compound (11 g); APCI m/z 359.0 [M+H]$^+$.

e) 6-(3-t-Butoxycarbonylaminopropyn-1-yl)-1-(dimethylamino)-4-oxo-1,4-dihydro-3-quinolinecarboxylic acid A stirred suspension of Intermediate 1d (20.46 g) and copper (I) iodide (1.08 g) in triethylamine (260 mL) and MeCN (380 mL) was degassed and covered with argon. After 15 min N-t-butoxycarbonylpropargylamine (Casara et al. J. Chem. Soc. Perkin Trans. 1 1985; 2201-2208) (10.6 g) and dichlorobis(triphenylphosphine)palladium (II) (1.26 g) were added. After 30 min the mixture was evaporated under reduced pressure and redissolved in aqueous potassium carbonate (16 g in 300 mL). The mixture was washed with diethyl ether (3×), filtered and acidified with citric acid. The solid was filtered off, washed with water and dried to give the title compound (16.5 g); APCI m/z 386.0 [M+H]$^+$.

f) 6-(3-t-Butoxycarbonylaminopropyl)-1-(dimethylamino)-4-oxo-1,4-dihydro-3-quinolinecarboxylic acid A solution of Intermediate 1e (17.26 g) and sodium hydroxide (2.7 g) in MeOH (150 mL) and water (300 mL) was treated with 10% palladium on carbon (1 g) and hydrogenated at room temperature and atmospheric pressure overnight. The reaction mixture was filtered, acidified with citric acid, the solid filtered off, washed with water and dried to give the title compound (16.2 g); APCI m/z 390.0 [M+H]$^+$.

g) 6-(3-Aminopropyl)-1-(dimethylamino)-4-oxo-1,4-dihydro-3-quinolinecarboxylic acid hydrochloride A solution of Intermediate 1f (16.2 g) in DCM (500 mL) at 20° C. was treated with 4M HCl in 1,4-dioxan (100 mL). After 1.5 h the solid was filtered off, washed with acetone and dried to yield the title compound (13.5 g); δ$_H$ (250 MHz; DMSO-d6) 1.94 (2H, m), 2.85 (4H, m), 2.97 (6H, s), 7.87 (1H, dd, J=1.8 & 8.8 Hz), 8.01 (3H, s), 8.20 (1H, d, J=1.8 Hz), 8.24 (1H, d, J=8.8 Hz), 9.28 (1H, s), APCI m/z 290.2 [M+H]$^+$.

Intermediate 2: 6-(3-Aminopropyl)-1-(morpholin-4-yl)-4-oxo-1,4-dihydro-3-quinolinecarboxylic acid hydrochloride a) Ethyl 3-(dimethylamino)-2-{[5-(3-t-butoxycarbonylamino)propyn-1-yl]-2-fluorobenzoyl}-2-propenoate A stirred suspension of Intermediate 1a (2.64 g) and copper (I) iodide (0.129 g) in triethylamine (30 mL) and MeCN (60 mL) was degassed and covered with argon. After 15 min N-t-butoxycarbonylpropargylamine (1.58 g) and dichlorobis(triphenylphosphine)palladium (II) (0.150 g) were added. After 30 min the mixture was evaporated under reduced pressure and redissolved in EtOAc. The mixture was washed with saturated sodium hydrogen carbonate solution, water (2×), dried (Na$_2$SO$_4$) and evaporated under reduced pressure. The residue was flash chromatographed on silica gel eluting with 10 to 40% EtOAc in DCM to give the title compound, (2.97 g); APCI m/z 419.2 [M+H]$^+$.

b) Ethyl 3-(dimethylamino)-2-[5-(3-t-butoxycarbonylamino)propyl]-2-fluorobenzoyl)-2-propenoate A solution of Intermediate 2a (3.97 g) in DCM (100 mL) was treated with 10% palladium on carbon (0.200 g). After 10 sec the solution was filtered and the catalyst replaced (0.300 g). The mixture was hydrogenated at room temperature and atmospheric pressure for 2 h, filtered and evaporated under reduced pressure to give the title compound (3.71 g); APCI m/z 423.3 [M+H]$^+$.

c) Ethyl 6-(3-t-butoxycarbonylaminopropyl)-1-(morpholin-4-yl)-4-oxo-1,4-dihydro-3-quinolinecarboxylate A mixture of Intermediate 2b (0.570 g) and potassium carbonate (0.224 g) in DMF (10 mL) was stirred at 100° C. for 1 h and then cooled to 20° C. The mixture was diluted with EtOAc, washed with water (2×) and a solid crystallised out. The solid was filtered off, washed with EtOAc and dried to give the title compound (0.445 g); APCI m/z 460.2 [M+H]$^+$.

d) 6-(3-t-Butoxycarbonylaminopropyl)-1-(morpholin-4-yl)-4-oxo-1,4-dihydro-3-quinolinecarboxylic acid Intermediate 2c (0.439 g) was suspended in THF (5 mL) and treated with 1N aqueous sodium hydroxide (1.43 mL) and water (5 mL). The mixture was stirred overnight. The solution was evaporated under reduced pressure to ca 5 mL and then acidified with citric acid. The solid was filtered off, washed with water and dried to give the title compound (0.308 g); APCI m/z 432.0 [M+H]⁺.

e) 6-(3-Aminopropyl)-1-(morpholin-4-yl)-4-oxo-1,4-dihydro-3-quinolinecarboxylic acid hydrochloride A solution of Intermediate 2d (0.384 g) in DCM (5 mL) at 20° C. was treated with 4M HCl in 1,4-dioxan (5 mL). After 1.5 h the mixture was evaporated under reduced pressure. The residue was triturated with acetone. The solid was filtered off, washed with acetone and dried to yield the title compound (0.325 g); APCI m/z 332.0 [M+H]⁺.

Intermediate 3: 6-(3-Aminopropyl)-1-(methylamino)-4-oxo-1,4-dihydro-3-quinolinecarboxylic acid trifluoroacetate a) Ethyl 3-(2-t-butoxycarbonyl-2-methylhydrazino)-2-(5-[3-t-butoxycarbonylaminopropyl)-2-fluorobenzoyl]-2-propenoate A stirred suspension of Intermediate 1a (0.839 g) in EtOH (10 mL) was treated with 1-t-butoxycarbonyl-1-methylhydrazine (0.320 g) (W. P. Malachowski et al., J. Org. Chem., 67(25), 2002, 8962-9). After stirring overnight the clear solution was evaporated under reduced pressure to give the title compound (1.03 g); APCI m/z 524.3 [M+H]⁺.

b) Ethyl 6-(3-t-butoxycarbonylaminopropyl)-1-(N-t-butoxycarbonyl-N-methylamino)-4-oxo-1,4-dihydro-3-quinolinecarboxylate A mixture of Intermediate 3a (1.0 g) and potassium carbonate (0.412 g) in DMF (10 mL) was stirred at 100° C. for 1 h and then cooled to 20° C. The mixture was diluted with EtOAc and acidified with citric acid, washed with water (2×) saturated brine, dried ($Na_2SO_4$) and evaporated under reduced pressure. The residue was flash chromatographed on silica gel eluting with 0 to 5% MeOH in DCM to give the title compound (0.79 g); APCI m/z 504.2 [M+H]⁺.

c) 6-(3-t-Butoxycarbonylaminopropyl)-1-(N-t-butoxycarbonyl-N-methylamino)-4-oxo-1,4-dihydro-3-quinolinecarboxylic acid Intermediate 3b (0.78 g) was suspended in THF (10 mL) and treated with 1N aqueous sodium hydroxide (2.33 mL). The mixture was stirred overnight, diluted with 50% aqueous EtOH (5 mL) and heated at 50° C. for 1 h to complete the hydrolysis. The solution was evaporated under reduced pressure to ca 10 mL and then acidified with citric acid. The mixture was extracted with DCM (2×). The combined extracts were dried ($Na_2SO_4$) and evaporated under reduced pressure to give the title compound (0.71 g); APCI m/z 476.2 [M+H]⁺.

d) 6-(3-Aminopropyl)-1-(methylamino)-4-oxo-1,4-dihydro-3-quinolinecarboxylic acid trifluoroacetate A solution of Intermediate 3c (0.71 g) in DCM (5 mL) at 20° C. was treated with TFA (3 mL). After 1 h toluene (5 mL) was added and the solution evaporated under reduced pressure. Re-evaporation from DCM (2×) and trituration with ether gave the title compound as a solid (0.57 g); APCI m/z 276.1 [M+H]⁺.

Intermediate 4: 4"-O-Propenoylerythromycin A (9E)-oxime a) 2'-O-Acetylerythromycin A (9E)-acetyloxime A solution of erythromycin A (9E)-oxime (8.5 g) in DCM (130 mL) was treated with sodium bicarbonate (2.09 g) followed by acetic anhydride (2.35 mL). After stirring overnight at room temperature the mixture was diluted with DCM and washed with water. The organic layer was separated, dried and evaporated under reduced pressure. The crude product was taken up in EtOAc and rewashed with saturated aqueous sodium bicarbonate. The organic layer was separated, dried and evaporated under reduced pressure to yield the title compound as a solid; ESMS m/z 833.6 [M+H]⁺.

b) 2'-O-Acetyl-4"-O-propenoyl erythromycin A (9E)-acetyloxime

A mixture of Intermediate 4a (8 g), triethylamine (4 mL) and 3-chloropropionyl chloride (1.37 mL) in toluene (200 mL) was stirred at 20° C. for 20 h. The reaction mixture was concentrated by evaporation under reduced pressure then partitioned between a saturated solution of $NH_4Cl$ and EtOAc. The organic phase was dried over $Na_2SO_4$, filtered and evaporated under reduced pressure. The crude product was purified by flash-chromatography 0-10% (9:1 MeOH/20 M $NH_3$) in DCM affording the title compound (4.0 g); ESMS m/z 887.6 [M+H]⁺.

c) 4"-O-Propenoylerythromycin A (9E)-oxime

Intermediate 4b (4.0 g) was dissolved in MeOH (200 mL) and stirred at 55° C. for 20 h, then at room temperature for 72 h. The solvent was evaporated under reduced pressure affording the title compound (3.53 g); ESMS m/z 803.5 [M+H]⁺.

Intermediate 5: 4"-O-Propenoyl erythromycin A (9E)-methoxime a) 2'-O-Acetylerythromycin A (9E)-methoxime A solution of erythromycin A (9E) methoxime (5.7 g) in DCM (70 mL) was treated with triethylamine (2.25 mL) followed by acetic anhydride (1.18 mL). After stirring overnight at room temperature the mixture was diluted with DCM and washed with aqueous sodium bicarbonate. The organic layer was separated, dried and evaporated to yield the title compound as a solid; ESMS m/z 805.8 [M+H]⁺.

b) 2'-O-Acetyl-4"-O-propenoyl erythromycin A (9E)-methoxime

Using a similar procedure to that described in Example 4b, Intermediate 5a (5.3 g) gave the title compound as a white solid; ESMS m/z 859.8 [M+H]⁺.

c) 4"-O-Propenoyl erythromycin A (9E)-methoxime

Using a similar procedure to that described in Example 4c, Intermediate 5b (4.17 g) gave the title compound as a white solid; ESMS m/z 817.6 [M+H]⁺.

Intermediate 6:
4"-O-Propenoyl-6-O-methyl-erythromycin A (9E)-oxime a) 2'-O-Acetyl-6-O-methyl-erythromycin A (9E)-acetyloxime

A solution of 6-O-methyl-erythromycin A oxime (0.995 g) in DCM (15 mL) was treated with sodium bicarbonate (0.24 g) followed by acetic anhydride (0.27 mL). After stirring overnight at room temperature the mixture was diluted with DCM and washed with aqueous sodium bicarbonate. The organic layer was separated, dried and evaporated to yield the title compound as a solid. ESMS m/z 847.5 [M+H]$^+$.

b) 2'-O-Acetyl-4"-O-propenoyl-6-O-methyl-erythromycin A (9E)-acetyloxime

Using a similar procedure to that described in Example 4b, Intermediate 6a (1.1 g) gave the title compound as a white solid. ESMS m/z 901.6 [M+H]$^+$.

c) 4"-O-Propenoyl-6-O-methyl-erythromycin A (9E)-oxime

Using a similar procedure to that described in Example 4c, Intermediate 6b (0.715 g) gave the title compound as a white solid. ESMS m/z 817.5 [MH$^+$].

Intermediate 7: 2'-Acetyl-4"-O-propenoyl-6-O-methyl-erythromycin A

A solution of 2'-acetyl-6-O-methyl-erythromycin A (218.05 g, 0.276 mol) dissolved in toluene (2 L) and triethylamine (115 mL, 0.828 mol) was treated dropwise with 3-chloropropionyl chloride (40 mL, 0.414 mol). The temperature temporarily rose to 40° C. After stirring at room temperature for 16 h some starting material remained. Further portions of triethylamine (20 mL) and 3-chloropropionyl chloride (7 mL) were added and stirring was continued for a further 1 h. The mixture was partitioned between DCM and saturated ammonium chloride solution (prone to emulsions which can be separated by the addition of some chloroform). The organic layer was separated and the aqueous layer extracted with chloroform (×4). The combined organics were dried and evaporated to yield the title compound as a white solid (208 g); ESMS m/z 844.8 [M+H]$^+$.

Intermediate 8:
4"-O-propenoyl-6-O-methyl-erythromycin A

A suspension of Intermediate 7 (191 g) in methanol (1.8 L) was stirred at 55° C. After 48 h the mixture was cooled in an ice bath and the solid formed was filtered and dried to yield the title compound as a white solid (143.6 g); ESMS m/z 802.8 [M+H]$^+$.

Intermediate 9: 2'-O-Acetyl-4"-O-propenoyl-azithromycin-11,12-carbonate

A solution of 2'-O-acetyl-azithromycin-11,12-carbonate (51.4 g) in toluene (190 mL) was stirred at 0° C. under an argon atmosphere. To this solution triethylamine (26.2 mL) was added followed by 3-chloro-propionyl chloride (7.24 mL) in toluene (10 mL) dropwise over a period of 30 minutes. After 30 minutes further triethylamine (6.5 mL) was added followed by 3-chloro-propionyl chloride (5.0 mL) in toluene (5 mL) dropwise over a period of 20 minutes. The solution was treated with a saturated aqueous solution of NaHCO$_3$ (200 mL), the phases separated and the aqueous phase extracted with toluene (200 mL and 100 mL). The combined organic phases were washed with water and brine, dried (Na$_2$SO$_4$), filtered and concentrated under reduced pressure. The residue was dissolved in acetonitrile (150 mL), the title compound crystallised as a white solid (29.7 g); ESMS m/z 871.6 [M+H]$^+$. A second crop of impure material (4.5 g) was obtained by concentration of the mother liquors.

Intermediate 10:
4"-O-Propenoyl-azithromycin-11,12-carbonate

A solution of Intermediate 9 (11.0 g) in MeOH (200 mL) was stirred at room temperature for 48 h. The solvent was evaporated under reduced pressure affording the title compound (9.81 g); $\delta_H$ (500 MHz) 6.45 (d, 1H), 6.17 (dd, 1H), 5.87 (d, 1H), 5.11 (d, 1H), 4.88 (dd, 1H), 4.77 (d, 1H), 4.53 (d, 1H), 4.47-4.40 (m, 3H), 3.72 (m, 1H), 3.60 (d, 1H), 3.33 (s, 3H), 3.25 (dd, 1H), 2.87-2.85 (m, 2H), 2.58 (m, 1H), 2.44-2.38 (m, 2H), 2.32 (s, 6H), 2.21 (s, 3H), 2.06 (m, 1H), 2.00 (m, 1H), 1.92 (m, 1H), 1.84 (m, 1H), 170-1.56 (m, 4H), 1.45 (s, 3H), 1.40 (dd, 1H), 1.29 (s, 3H), 1.25 (m, 1H), 1.22 (d, 3H), 1.18 (d, 6H), 1.12 (s, 3H), 108-1.06 (2 d, 6H), 0.93 (m, 6H); ESMS m/z 829.1 [M+H]$^+$.

Intermediate 11: 6-(2-Aminoethylsufanyl)-1-dimethylamino-4-oxo-14-dihydro-[1,7]-naphthyridine-3-carboxylic acid hydrochloride salt a) 2-[1-(2,5-Dichloropyridin-4-yl)methanoyl]-3-dimethylaminoacrylic acid ethyl ester A stirred suspension of 2,5-dichloroisonicotinic acid (1.49 g) in DCM (20 mL) was treated with oxalyl chloride (1 mL) and dimethylformamide (1 drop). After 1 h the clear solutin was evaporated and re-evaporated from toluene (2×). The acid chloride was re-dissolved in toluene (50 mL) and treated with triethylamine (1.62 mL) and ethyl 3-(dimethylamino) acrylate (1.44 g). After stirring for 1.5 h at 90° C. the mixture cooled, filtered and purified by chromatography (silica gel, 50-70% EtOAc in petroleum ether [b.p. 40-60° C.]) to give the title compound as a yellow gum (2.3 g); APCIMS m/z 317.0, 319.0, 321.0 [M+H]$^+$.

b) 2-[1-(2,5-Dichloropyridin-4-yl)methanoyl]3-(2,2-dimethylhydrazino) acrylic acid ethyl ester A stirred solution of Intermediate 11a (2.3 g) in ethanol (25 mL) was treated with 1,1-dimethylhydrazine (0.61 mL). After 2 h the solution was evaporated to give the title compound as a yellow gum (2.38 g); ESMS m/z 332.1, 334.1, 336.1 [M+H]$^+$.

c) 6-Chloro-1-(dimethylamino)-4-oxo-1,4-dihydro-[1,7]-naphthyridine-3-carboxylic acid ethyl ester A mixture of Intermediate 11b (0.538 g) and potassium carbonate (0.336 g) in dimethylformamide (5 mL) was stirred at 100° C. for 3 h and then cooled to room temperature. The mixture was poured into 1% citric acid, the solid filtered off, washed with water and dried to give the title compound as a yellow solid (0.295 g); APCIMS m/z 296.0, 298.0 [M+H]$^+$.

d) 6-(2-tert-Butylcarbonylaminoethylsufanyl)-1-dimethylamino-4-oxo-1,4-dihydro-[1,7]-naphthyridine-3-carboxylic acid ethyl ester A solution of Intermediate 11c (0.285 g) in N,N-dimethylformamide (5 mL) was treated with potassium carbonate (0.200 g) and tert-butyl N-(2-mercaptoethyl)-carbamate (0.2 mL). The mixture was stirred at 50° C. for 1.5 h and then at 70° C. overnight. Further tert-butyl N-(2-mercaptoethyl)-carbamate (0.2 mL) was added and heating continued for 4 h. The mixture was cooled, poured into water and extracted with DCM. The DCM extracts were dried ($MgSO_4$) evaporated, and the residue chromatographed (silica gel, 0-5% methanol in DCM) to give the title compound as a yellow solid (0.309 g); ESMS m/z 437.1 $[M+H]^+$.

e) 6-(2-tert-Butylcarbonylaminoethylsufanyl)-1-dimethylamino-4-oxo-1,4-dihydro-[1,7]-naphthyridine-3-carboxylic acid Intermediate 11d (0.306 g) in ethanol (33 mL) was treated with 1M NaOH (1.05 mL) and the solution stirred for 30 min. Water (5 mL) was added and the solution stirred overnight. The ethanol was evaporated and the aqueous acidified with 5% citric acid solution. The solid was filtered off, washed with water and dried to give the title compound as a yellow solid (0.280 mg); APCIMS m/z 409.2 $[M+H]^+$.

f) 6-(2-Aminoethylsufanyl)-1-dimethylamino-4-oxo-1,4-dihydro-[1,7]-naphthyridine-3-carboxylic acid hydrochloride salt Intermediate 11e (0.280 g) in DCM (5 mL) was treated with 4M HCl in 1,4-dioxan (5 mL). After 2 h the solid was filtered off, washed with acetone and dried to give the title compound as a yellow solid (0.214 g); APCIMS m/z 309.1 $[M+H]^+$.

Intermediate 12: 7-(2-Aminoethoxy)-1-(dimethylamino)-4-oxo-1,4-dihydroquinoline-3-carboxylic acid hydrochloride salt a) 4-Acetoxy-2-fluorobenzoic acid

A stirred mixture of 2-fluoro-4-hydroxybenzoic acid (5 g) (G. W. Gray et al. Mol. Cryst. Liq. Cryst. 67, 1981, 1-24), 4-dimethylaminopyridine (0.010 g) and triethylamine (11 mL) in DCM (100 mL) was treated with acetic anhydride (6.35 mL). After 2 h the solution was evaporated and the residue redissolved in EtOAc, washed with 5% citric acid, water (3×), dried ($Na_2SO_4$) and evaporated to give the title compound as a white solid (4.92 g); APCI m/z 199.1 $[M+H]^+$.

b) Ethyl 3-(dimethylamino)-2-(2-fluoro-4-acetoxybenzoyl)-2-propenoate

A stirred solution of Intermediate 12a (4.91 g) in DCM (80 mL) was treated with oxalyl chloride (3.25 mL) and dimethylformamide (2 drops). After 2 h the clear solution was evaporated and re-evaporated from DCM (2×). The acid chloride was re-dissolved in toluene (100 mL) and treated with triethylamine (5.17 mL) and ethyl 3-(dimethylamino)acrylate (4.13 g). After stirring for 2 h at 90° C. the mixture was cooled, filtered and the solution flash chromatographed (silica gel 40 to 100% EtOAc in petroleum ether [b.p. 40-60° C.]) to give the title compound as a white solid (4.3 g); APCI m/z 324.0 $[M+H]^+$.

c) Ethyl 1-dimethylamino-7-hydroxy-4-oxo-1,4-dihydro-quinoline-3-carboxylate A solution of Intermediate 12b (1.77 g) in EtOH (20 mL) was treated with 1,1-dimethylhydrazine (2.08 mL) and stood for 2 h. The solution was evaporated and the residue redissolved in dimethylformamide (20 mL), treated with potassium carbonate (1.51 g) and stirred at 100° C. for 1 h. The mixture was cooled, filtered, evaporated to low volume and poured into 5% citric acid. The title compound was filtered off, washed with water and dried to give a white solid (1.09 g); APCI m/z 277.0 $[M+H]^+$.

d) Ethyl 7-(2-t-butoxycarbonylaminoethoxy)-1-dimethylamino-4-oxo-1,4-dihydro-quinoline-3-carboxylate A stirred mixture of Intermediate 12c (1.09 g) t-butyl 2-hydroxyethylcarbamate (0.67 mL) and triphenylphosphine (1.35 g) in dry THF (20 mL) under argon was treated with diisopropyl azodicarboxylate (1 mL) and stirred overnight. The solution was evaporated and the residue redissolved in EtOAc. Washed with 5% sodium carbonate solution (2×), water (2×), dried ($Na_2SO_4$), evaporated and flash chromatographed (silica gel 30 to 50% EtOAc in DCM then 5% methanol in DCM) to give the title compound as a white solid (1.5 g); APCI m/z 420.3 $[M+H]^+$.

e) 7-(2-t-Butoxycarbonylaminoethoxy)-1-dimethylamino-4-oxo-1,4-dihydro-quinoline-3-carboxylic acid Intermediate 12d (1.5 g) was suspended in methanol (10 mL) and treated with 1N aqueous sodium hydroxide (5.4 mL). The mixture was stirred overnight. The solution was evaporated to low volume, acidified with 5% citric acid and extracted with DCM (2×). The combined extracts were washed with water (2×) dried ($Na_2SO_4$) and evaporated to give the title compound as a white solid (1.27 g); APCI m/z 392.2 $[M+H]^+$.

f) 7-(2-Aminoethoxy)-1-dimethylamino-4-oxo-1,4-dihydro-quinoline-3-carboxylic acid A solution of Intermediate 12e (1.27 g) in DCM (10 mL) was treated with 4M HCl in 1,4-dioxan (5 mL). After 2 h the solid was filtered off, washed with acetone and dried to give the title compound as a white solid (1 g); APCI m/z 292.2 $[M+H]^+$.

Intermediate 13: 4"-O-Propenoyl-azithromycin

To a solution of Intermediate 10 (24.9 g) in acetonitrile (500 mL), a saturated aqueous solution of potassium carbonate (250 mL) was added. The resulting mixture was heated to 80° C. for 18 h. The mixture was cooled and the phases separated. The organic phase was concentrated by evaporation under reduced pressure and the residue taken up in EtOAc (500 mL) and washed with water (2×25 mL). The organic phase was dried ($Na_2SO_4$), filtered and concentrated under reduced pressure. The crude product was crystallised from diethyl ether (100 mL) and light petroleum [bp 40-60°] (100 mL) affording the title compound (12.6 g) as a white solid; ESMS m/z 803.9 $[M+H]^+$.

Intermediate 14: 9-(3-Aminopropyl)-3-methyl-7-oxo-2,3-dihydro-7H-[1,3,4]oxadiazino[6,5,4-ij]quinoline-6-carboxylic acid hydrochloride a) Ethyl 3-(dimethylamino)-2-(2,3-difluoro-5-iodobenzoyl)-2-propenoate A stirred suspension of 2,3-difluoro-5-iodobenzoic acid (Pharmacia & Upjohn Company patent WO 02/04445 p 90) (2.84 g) in DCM (50 mL) was treated with oxalyl chloride (1.3 mL) and dimethylformamide (2 drops). After 1.5 h the clear solution was evaporated and re-evaporated from toluene (2×). The acid chloride was dissolved in toluene (50 mL) and treated with triethylamine (2.1 mL) and ethyl 3-(dimethylamino)acrylate (1.86 g). After stirring for 2 h at 90° C. the mixture was cooled, filtered and the solution chromatographed on silica gel eluting with 0% to 70% EtOAc in hexane to give the title compound as a yellow solid (3.05 g); ESMS m/z 410.1 [M+H]$^+$.

b) Ethyl 1-(tert-butoxycarbonyl-methylamino)-8-fluoro-6-iodo-4-oxo-1,4-dihydro-3-quinolinecarboxylate A stirred solution of Intermediate 14a (2.2 g) in ethanol (27 mL) was treated with 1-tert-butoxycarbonyl-1-methylhydrazine (0.865 g). After 1.5 h the clear solution was evaporated and chromatographed on silica gel eluting with 0% to 30% EtOAc in hexane to give the title compound as a white solid (3 g); APCI m/z 491.2 [M+H]$^+$.

c) Ethyl 8-fluoro-6-iodo-1-methylamino-4-oxo-1,4-dihydro-3-quinoline carboxylate A solution of Intermediate 14b (0.333 g) in DCM (2 ml) and TFA (4 mL) was kept for 1 h and then concentrated. The residue was chromatographed on silica gel eluting with 0-5% (9:1 methanol/20M aq. ammonia) in DCM to give the title compound as a white solid (0.27 g); ESMS m/z 391.2 [M+H]$^+$.

d) Ethyl 8-fluoro-1-[(hydroxymethyl)(methyl)amino]-6-iodo-4-oxo-1,4-dihydro-3-quinolinecarboxylate A suspension of Intermediate 14c (2.76 g) and paraformaldehyde (9.37 g) in water (350 mL) was refluxed for 16 h then allowed to cool. The mixture was extracted with chloroform, the organic phase was washed with water then dried (MgSO$_4$) and concentrated to give the title compound as a white solid (2.1 g); ESMS m/z 421.2 [M+H]$^+$.

e) Ethyl 9-iodo-3-methyl-7-oxo-2,3-dihydro-7H-[1,3,4]oxadiazino[6,5,4-ij]quinoline-6-carboxylate A suspension of Intermediate 14d (0.21 g) in THF (35 mL) was heated quickly to reflux (<5 min). Tetrabutylammonium fluoride (1.1 mL of 1.0M solution in THF) was added as quickly as possible via syringe and the mixture was heated at reflux for 20 min. The reaction mixture was poured into saturated sodium bicarbonate solution and the product extracted into EtOAc. The combined extracts were washed with brine then dried (MgSO$_4$) and concentrated. The residue was chromatographed on silica gel eluting with 0-5% (9:1 methanol/20M aq. ammonia) in DCM to give the title compound as a white solid (0.07 g); ESMS m/z 401.2 [M+H]$^+$.

f) Ethyl 9-[3-(tert-butoxycarbonylamino)prop-2-yn-1-yl]-3-methyl-7-oxo-2,3-dihydro-7H-[1,3,4]oxadiazino[6,5,4-ij]quinoline-6-carboxylate A stirred suspension of Intermediate 14e (0.54 g) and copper (I) iodide (0.028 g) in triethylamine (6.5 mL) and acetonitrile (13 mL) was degassed with argon at 50° C. After 20 mins N-t-butoxycarbonylpropargylamine (0.35 g) and dichlorobis(triphenylphosphine)palladium (II) (0.028 g) were added and the brown suspension was stirred at 50° C. After 15 min the mixture was evaporated and the residue was chromatographed on silica gel eluting with 0-3% (9:1 20M aq. ammonia/methanol) in DCM to give the title compound as a beige solid (0.58 g); ESMS m/z 428.4 [M+H]$^+$.

g) Ethyl 9-[3-(tert-butoxycarbonylamino)propyl]-3-methyl-7-oxo-2,3-dihydro-7H-[1,3,4]oxadiazino[6,5,4-ij]quinoline-6-carboxylate A solution of Intermediate 14f (0.58 g) in DCM (20 mL) was treated with 10% palladium on carbon (0.5 g) and hydrogenated at room temperature and atmospheric pressure overnight. The reaction mixture was filtered through celite and the solution was chromatographed on silica gel eluting with 0-10% (9:1 methanol/20M aq. ammonia) in DCM to give the title compound as a pale yellow solid (0.185 g); ESMS m/z 432.4 [M+H]$^+$.

h) 9-(3-aminopropyl)-3-methyl-7-oxo-2,3-dihydro-7H-[1,3,4]oxadiazino[6,5,4-ij]quinoline-6-carboxylic acid hydrochloride A solution of Intermediate 14g (0.17 g) in dioxan (4 mL) was treated with 2M aqueous hydrogen chloride (5 mL). The reaction mixture was heated to 50° C. overnight then concentrated to yield the title compound as a pale yellow solid (0.34 g); ESMS m/z 319.3 [M+H]$^+$.

Intermediate 15: 6-(2-Aminoethylsulfanyl)-1-(dimethylamino)-4-oxo-1,4-dihydro-quinoline-3-carboxylic acid trifluoroacetate salt a) Ethyl 2-[(2,5-difluorophenyl)carbonyl]-3-(dimethylamino)-2-propenoate A solution of 2,5-difluorobenzoyl chloride (5.26 g, 29.8 mmol) in toluene (100 mL) was treated with ethyl-3-(dimethylamino)-2-propenoate (5.27 g, 36.8 mmol), followed by triethylamine (5.9 mL, 42.5 mmol). The mixture was stirred at 90° C. for 6.5 h then allowed to cool, and the precipitate removed by filtration. The filtrate was concentrated under reduced pressure to give a residue which was purified by flash chromatography (silica gel, 50-100% diethyl ether in petroleum ether [b.p. 40-60° C.]) to give the title compound as a yellow oil (0.95 g); ESMS m/z 284.4 [M+H]$^+$.

b) Ethyl 2-[(2,5-difluorophenyl)carbonyl]-3-(2,2-dimethylhydrazino)-2-propenoate A stirred solution of Intermediate 15a (0.93 g, 3.28 mmol) in ethanol (10 mL) was treated with 1,1-dimethylhydrazine (0.27 mL, 3.61 mmol). After 2 h a further aliquot of 1,1-dimethylhydrazine (0.05 mL, 0.66 mmol) was added, and stirring continued for another 25 min. The mixture was concentrated under reduced pressure to give the title compound as a yellow oil (1.01 g); ESMS m/z 299.1 [M+H]$^+$.

c) Ethyl 1-(dimethylamino)-6-fluoro-4-oxo-1,4-dihydro-quinoline-3-carboxylate A mixture of Intermediate 15b (0.98 g, 3.28 mmol) and potassium carbonate (0.68 g, 4.92 mmol) in N,N-dimethylformamide (10 mL) was stirred at 100° C. for 55 min and then cooled. The mixture was treated with water, the solid filtered off, washed with water then dried in vacuo to give the title compound as a pale yellow solid (0.63 g); ESMS m/z 279.2 [M+H]$^+$.

d) 6-(2-tert-Butoxycarbonylamino-ethylsulfanyl)-1-(dimethylamino)-4-oxo-1,4-dihydro-quinoline-3-carboxylic acid ethyl ester A mixture of Intermediate 15c (1.00 g, 3.60 mmol), and potassium carbonate (0.99 g, 7.16 mmol) in dimethyl sulfoxide (18 mL) was treated with tert-butyl N-(2-mercaptoethyl)-carbamate (1.3 mL, 7.7 mmol) and heated to 70° C. After 21 h the mixture was allowed to cool to room temperature then diluted with water and extracted with EtOAc. The organic extracts were combined, dried (MgSO$_4$), filtered, and concentrated under reduced pressure to give a residue which was purified by flash chromatography (silica gel, 20-100% EtOAc in petroleum ether [b.p. 40-60° C.]) to give the title compound as a white solid (1.08 g); ESMS m/z 436.2 [M+H]$^+$.

e) 6-(2-tert-Butoxycarbonylamino-ethylsulfanyl)-1-(dimethylamino)-4-oxo-1,4-dihydro-quinoline-3-carboxylic acid Intermediate 15d (1.07 g, 2.46 mmol) was dissolved in THF (16 mL) and treated with 0.2N aqueous sodium hydroxide (15 mL). The solution was stirred for 18.5 h then concentrated under reduced pressure to give a residue which was taken up in water and treated with excess solid carbon dioxide. The resulting precipitate was removed by filtration and dried in vacuo to give the title compound as a white solid (0.92 g); ESMS m/z 408.2 [M+H]$^+$.

f) 6-(2-Aminoethylsulfanyl)-1-(dimethylamino)-4-oxo-1,4-dihydro-quinoline-3-carboxylic acid trifluoroacetate salt Intermediate 15e (0.90 g, 2.21 mmol) was dissolved in DCM (20 mL) and treated with TFA (8 mL). After stirring for 30 min the mixture was concentrated under reduced pressure. Toluene, and DCM were added to the residue and the mixture concentrated under reduced pressure. The resulting residue was triturated with diethyl ether then dried in vacuo to give the title compound as a white solid (0.92 g); ESMS m/z 308.1 [M+H]$^+$.

Intermediate 16: 4"-O-Propenoyl-erythromycin A-(9E)-oxime-11,12-carbonate a) 2'-O-acetyl-erythromycin A-(9E)-O-acetyl-oxime-11,12-carbonate

To an ice cooled solution of Intermediate 4a (4.64 g, 5.57 mmol) and pyridine (4.50 mL, 55.8 mmol) in DCM (40 mL) was added triphosgene (1.65 g, 5.57 mmol). The mixture was stirred for 2.5 h then further triphosgene (0.55 g, 1.86 mmol) added. Stirring was continued for 50 min then the mixture concentrated under reduced pressure to give a residue which was taken up in EtOAc and washed with a saturated sodium hydrogen carbonate solution. The organic layer was dried (Na$_2$SO$_4$), filtered, then concentrated under reduced pressure to give a residue which was purified by flash chromatography (silica gel, 0-8% methanol in DCM) to give the title compound as a cream solid (3.25 g); ESMS m/z 859.9 [M+H]$^+$.

b) 4"-O-Propenoyl-2'-O-acetyl-erythromycin A-(9E)-O-acetyl-oxime-11,12-carbonate To a stirred solution of Intermediate 16a (2.10 g, 2.45 mmol) in toluene (25 mL) was added triethylamine (1.02 mL, 7.32 mmol), followed by 3-chloropropanoyl chloride (0.35 mL, 3.67 mmol). After 1.5 h further 3-chloropropanoyl chloride (0.35 mL, 3.67 mmol) and triethylamine (1.02 mL, 7.32 mmol) were added, and stirring continued for 35 min. Saturated sodium ammonium chloride was then added, and the mixture concentrated under reduced pressure to give a residue which was taken up in water and extracted with DCM. The organic phase was dried (Na$_2$SO$_4$), filtered, then concentrated under reduced pressure to give a residue which was purified by flash chromatography (silica gel, 0-7% methanol in DCM) to give the title compound as a white solid (1.36 g); ESMS m/z 913.9 [M+H]$^+$.

c) 4"-O-Propenoyl-erythromycin A-(9E)-oxime-11,12-carbonate

A solution of Intermediate 16b (1.36 g, 1.49 mmol) in methanol (100 mL) was stirred at 50° C. for 17 h, then 60° C. for a further 70 h. The mixture was then concentrated under reduced pressure and the residue purified by flash chromatography (silica gel, 0-8% methanol in DCM) to give the title compound as a white solid (0.79 g); ESMS m/z 829.8 [M+H]$^+$.

Intermediate 17: 6-((Z)-3-tert-Butoxycarbonyloxypropen-1-yl)-1,4-dihydro-1-dimethylamino-4-oxo-quinoline-3-carboxylic acid ethyl ester a) 6-(3-Hydroxypropyn-1-yl)-1,4-dihydro-1-dimethylamino-4-oxo-quinoline-3-carboxylic acid ethyl ester Intermediate 1c (2.0 g, 5.4 mmol), copper (I) iodide (0.05 g, 0.26 mmol) were suspended in dry acetonitrile (100 mL) and triethylamine (40 mL). The light green suspension was heated to 40° C. under argon. After 30 min, the reaction was cooled to room temperature and dichlorobis(triphenylphosphine)palladium (II) (0.05 g, 0.07 mmol) and propargyl alcohol (0.63 mL, 10.8 mmol) were added. The mixture was stirred under argon at for 1 h. The reaction mixture was diluted with EtOAc (100 mL) and diethyl ether (100 mL) and washed with water (200 mL) and brine (20 mL). The aqueous layers were extracted with EtOAc (3×100 mL) and the combined organic extracts dried (MgSO$_4$) and evaporated under reduced pressure. The crude product was suspended in ethanol (50 mL). The title compound (1.07 g) was filtered off. The ethanol soluble material was purified by chromatography on silica gel eluting with a gradient of methanol in DCM. Product containing fractions were evaporated to dryness to yield further title compound (0.3 g); total title compound as a white solid (1.37 g); ESMS m/z 315.3 [M+H]$^+$.

b) 6-((Z)-3-Hydroxypropen-1-yl)-1,4-dihydro-1-dimethylamino-4-oxo-quinoline-3-carboxylic acid ethyl ester Intermediate 17a (1.37 g, 4.35 mmol) in ethanol (10 mL) and DCM (10 mL) was stirred with 10% palladium on carbon for 10 min under argon. The catalyst was filtered off and washed with 1:1 ethanol/DCM (30 mL). The combined filtrates were hydrogenated at 20° C. and 1 atm over Lindlar catalyst (0.5 g). After 4 h the catalyst was filtered off and washed well with ethanol/DCM. The combined filtrates were evaporated to dryness to give the title compound as a yellow solid contaminated with 6-(3-hydroxypropyl)-1,4-dihydro-1-dimethylamino-4-oxo-quinoline-3-carboxylic acid ethyl ester (1.46 g); ESMS m/z 317.2, 319.2 $[M+H]^+$.

c) 6-((Z)-3-tert-Butoxycarbonyloxypropen-1-yl)-1,4-dihydro-1-dimethylamino-4-oxo-quinoline-3-carboxylic acid ethyl ester Intermediate 17b (1.46 g) in THF (40 mL) was treated with di-tert-butyl dicarbonate (1.3 g, 6.0 mmol) and N-methylimidazole (0.038 g, 0.46 mmol). After stirring for 40 min DCM (10 mL) was added. After 24 h at 20° C. further di-tert-butyl dicarbonate (0.9 g, 4.1 mmol) and N-methylimidazole (0.040 g, 0.48 mmol) were added. After a further 20 h, the solvents were evaporated and the crude product was purified by chromatography on silica gel eluting with a gradient of methanol in DCM to give the title compound contaminated with 6-(-3-tert-butoxycarbonyloxypropyl)-1,4-dihydro-1-dimethyamino-4-oxo-quinoline-3-carboxylic acid ethyl ester (1.31 g) as a white solid; ESMS m/z 417.2, 419.3 $[M+H]^+$.

Intermediate 18: 9-Dihydro-4"-O-(3-hydroxypropyl)-9-methoxy-2',11-bis-O-trimethylsilyl-6-O-methyl-9,12-anhydro-erythromycin A a) 4"-O-(Imidazol-1-yl-carbonyl)-6-O-methyl-erythromycin A

6-O-Methyl-erythromycin A (30 g, 40.1 mmol) in THF (100 mL) was treated portionwise with carbonyldiimidazole (16 g, 97 mmol) with ice bath cooling. After 1 h the cooling bath was removed. After a further 48 h, THF (100 mL) and water (200 mL) were added slowly precipitating the title compound, which was collected by filtration and dried to give the title compound as a white solid (24.7 g). Extraction of the mother liquors with diethyl ether gave further material (8.5 g) which was precipitated from THF solution with water to give a further portion of the title compound (3.92 g, total of 28.64 g); ESMS m/z 842.6 $[M+H]^+$.

b) 4"-O-(Allyloxycarbonyl)-6-O-methyl-erythromycin A

Intermediate 18a (28.64 g, 34 mmol) in DCM (100 mL) was cooled to 0° C. and treated with allyl alcohol (13.6 mL) and DBU (5.23 mL). The reaction was stirred at 0° C. for 2.5 h and at room temperature for 1.75 h. The reaction mixture was quenched with 3% aq citric acid (100 mL), the phases separated, and the organic phase washed with sat sodium hydrogen carbonate and brine. After drying and evaporation to dryness, the residue was triturated with petroleum ether (bp 40-60° C.) to give the title compound as a white solid (25.08 g); ESMS m/z 832.5 $[M+H]^+$.

c) 4"-O-(Allyloxycarbonyl)-9-dihydro-9-methoxy-2',11-bis-O-trimethylsilyl-6-O-methyl-9,12-anhydro-erythromycin A Intermediate 18b (21.29 g, 25.6 mmol) in pyridine (100 mL) was treated with chlorotrimethylsilane (26 mL). The reaction was stirred at room temperature for 6 h and left at 4° C. for 16 h. The reaction mixture was evaporated to dryness under reduced pressure and the residue taken up in methanol (100 mL). After 80 min at room temperature, the solvent was removed by evaporation under reduced pressure and the residue taken up in EtOAc and water. The phases were separated, the organic layer dried, and evaporated to dryness under reduced pressure. Toluene (two 500 mL portions) were added and evaporated under reduced pressure to give the crude title compound as a white foam (26.27 g). This material (5.8 g) was purified by chromatography on silica gel eluting with 0-3% 2 M methanolic ammonia in DCM to give the title compound as a white solid foam (3.0 g); ESMS m/z 990.7 $[M+H]^+$.

d) 4"-O-Allyl-9-dihydro-9-methoxy-2',11-bis-O-trimethylsilyl-6-O-methyl-9,12-anhydro-erythromycin A Intermediate 18c (3.0 g, 3.03 mmol) in THF (20 mL) was treated with tetrakis triphenylphosphine palladium (0.1 g) at reflux under argon. After 35 min, t-butyl allyl carbonate (F. Houlihan et al, *Can. J. Chem.* 1985, 63, 153; 1.2 mL) and tetrakis(triphenylphosphine) palladium (0.1 g) were added and the reflux continued for a further 1 h. The reaction was cooled and evaporated to dryness under reduced pressure, and the residue purified by chromatography on silica gel eluting with 0-5% methanolic ammonia [2M] in DCM to give the title compound as a white foam (1.07 g); ESMS m/z 946.7 $[M+H]^+$.

e) 9-Dihydro-4"-O-(3-hydroxypropyl)-9-methoxy-2',11-bis-O-trimethylsilyl-6-O-methyl-9,12-anhydro-erythromycin A Intermediate 18d (0.255 g, 0.27 mmol) in THF (4 mL) under argon was treated with 9-BBN (0.5 M in THF, 1.6 mL). After 30 min, the reaction was cooled to 0° C. and a precooled mixture of sodium hydroxide (2 M, 0.5 mL) and hydrogen peroxide (27% in water, 0.68 mL) were added. This was stirred at 0° C. for 10 min before addition of cold diethyl ether and water. The phases were separated and the organic phase washed with water and brine. After drying and evaporation under reduced pressure the residue was purified by chromatography on silica gel eluting with 0-10% methanolic ammonia [2M] in DCM to give the title compound as a white solid foam (0.16 g); ESMS m/z 964.7 $[M+H]^+$.

Intermediate 19: 6-(2-Aminoethylsufanyl)-1-dimethylamino-4-oxo-1,4-dihydro-[1,8]-naphthyridine-3-carboxylic acid trifluoroacetate salt a) 2-[1-(5-Bromo-2-chloro-3-pyridin-3-yl)methanoyl]3-(dimethylamino)acrylic acid ethyl ester A stirred suspension of 2-chloro-5-bromo pyridine-3-carboxylic acid (5 g) in DCM (50 mL) was treated with oxalyl chloride (2.8 mL) and N,N-dimethylformamide (1 drop). After 1 h the clear solution was evaporated and re-evaporated from toluene (2×). The acid chloride was re-dissolved in toluene (80 mL) and treated with triethylamine (4.7 mL) and ethyl 3-(dimethylamino)acrylate (3.94 g). After stirring for 1 h at 90° C. the mixture was cooled and poured onto ice. Saturated aqueous sodium hydrogen carbonate (50 mL) was added and the organic layer washed with water and brine, dried (MgSO$_4$), evaporated and the residue purified by chromatography (silica gel, 50-100% diethyl ether in petroleum ether [b.p. 40-60° C.]) to give the title compound as a colourless gum, (6.45 g); ESMS m/z 361.0, 363.0, 365.0 [M+H]$^+$, 315.0, 317.0, 319.0 [M–OEt]$^+$.

b) [1-(5-Bromo-2-chloro-3-pyridin-3-yl)methanoyl] 2,2-dimethylhydrazino acrylic acid ethyl ester A stirred suspension of Intermediate 19a (6.45 g) in ethanol (50 mL) was treated with 1,1-dimethylhydrazine (1.29 mL). After standing at overnight the colourless solid was collected by filtration. A second crop was obtained by concentrating the mother liquors and combined with the first crop to give the title compound (6.36 g) as a white solid; ESMS m/z 376.0, 378.0, 380.0 [M+H]$^+$.

c) 6-Bromo-1-(dimethylamino)-4-oxo-1,4-dihydro-[1,8]-naphthyridine-3-carboxylic acid ethyl ester A mixture of Intermediate 19b (3.65 g) and potassium carbonate (3.5 g) in N,N-dimethylformamide (50 mL) was stirred at 60° C. for 1 h and then cooled. The mixture was poured into water, the solid filtered off then washed with water and dried to give the title compound as a white solid (5.36 g); ESMS m/z 340.0, 342.0 [M+H]$^+$.

d) 6-(2-tert-Butylcarbonylaminoethylsufanyl)-1-dimethylamino-4-oxo-1,4-dihydro-[1,8]-naphthyridine-3-carboxylic acid ethyl ester Intermediate 19c (1.5 g) was suspended in dimethyl sulfoxide (20 mL) treated with potassium carbonate (1.12 g) and tert-butyl N-(2-mercaptoethyl)-carbamate (1.06 g). The mixture was stirred at 55° C. for 2.25 h and then cooled, poured into water and extracted with EtOAc. The EtOAc extracts were dried (MgSO$_4$) evaporated, and the residue triturated with diethyl ether/petroleum ether [b.p. 40-60° C.] (1:1, 20 mL) to give the title compound as a yellow solid (1.46 g); ESMS m/z 437.2 [M+H]$^+$.

e) 6-(2-tert-Butylcarbonylaminoethylsufanyl)-1-dimethylamino-4-oxo-1,4-dihydro-[1,8]-naphthyridine-3-carboxylic acid Intermediate 19d (1.46 g) in THF (30 mL) and water (10 mL) was treated with 2M NaOH (2 mL) and the mixture stirred under argon for 17 h. Solid carbon dioxide was added to precipitate a yellow solid. This was filtered, washed with water and dried to give the title compound (0.954 g); ESMS m/z 409.2 [M+H]$^+$.

f) 6-(2-Aminoethylsufanyl)-1-dimethylamino-4-oxo-1,4-dihydro-[1,8]-naphthyridine-3-carboxylic acid trifluoroacetate salt Intermediate 19e (0.954 g) in DCM (10 mL) was treated with TFA (5 mL). After 15 min toluene (15 mL) was added, and the mixture evaporated to dryness to give a yellow gum. Addition of diethyl ether and sonication gave the title compound as a white solid (1.01 g); $\delta_H$ (250 MHz; DMSO-d$_6$) 14.4 (1H, bs), 9.1 (1H, d), 9.0 (1H, s), 8.7 (1H, d), 8.0 (3H, bs) 3.4 (2H, t), 3.2 (6H, s), 3.0 (2H, bm).

Intermediate 20: 6-(3-Aminopropyl)-1-dimethylamino-4-oxo-1,4-dihydro-[1,8]-naphthyridine-3-carboxylic acid trifluoroacetate salt a) 6-(3-tert-Butylcarbonylaminopropyl)-1-dimethylamino-4-oxo-1,4-dihydro-[1,8]-naphthyridine-3-carboxylic acid ethyl ester To Boc-allylamine (0.785 mL, 5 mmol) under argon was added 9-BBN (0.5M in THF, 10 mL). After stirring at 20° C. for 2.25 h, Intermediate 18c (1.02 g, 3.0 mmol) tetrakistriphenylphosphine palladium (0.1 g), and potassium phosphate (2.15 g) were added. The mixture was heated to reflux for 1.5 h. The reaction was cooled, diluted with EtOAc (50 mL) and washed with water (20 mL). The organic layer was dried (MgSO$_4$), evaporated and the residue purified by chromatography on silica gel eluting with 0-40% EtOAc in DCM to give the title compound as a white solid (0.93 g); ESMS m/z 419.3 [M+H]$^+$.

b) 6-(3-tert-Butylcarbonylaminopropyl)-1-dimethylamino-4-oxo-1,4-dihydro-[1,8]-naphthyridine-3-carboxylic acid To Intermediate 20a (0.93 g) in THF (20 mL) and water (10 mL) under argon was added 2M NaOH (1.5 mL). After stirring at for 3.5 h, solid carbon dioxide was added. The mixture was extracted with EtOAc, acidified to pH 6 and extracted with EtOAc, then acidified to pH 3 and extracted with EtOAc. The combined extracts were dried (MgSO$_4$), and evaporated to give the title compound as a white solid (0.68 g); ESMS m/z 491.2 [M+H]$^+$.

c) 6-(3-Aminopropyl)-1-dimethylamino-4-oxo-1,4-dihydro-[1,8]-naphthyridine-3-carboxylic acid trifluoroacetate salt To Intermediate 20b (0.68 g) in DCM (20 mL) was added TFA (10 mL). After 20 min, toluene (20 mL) was added and the solvents evaporated. To the residual gum was added diethyl ether (50 mL) and the mixture sonicated to give the title compound as a white solid (0.72 g); ESMS m/z 291.3 [M+H]$^+$, 273.3 [M–OH]$^+$.

Intermediate 21: 4"-O-Propenoyl-erythromycin A-(9E)-O-methoxymethyloxime a) 2'-O-Acetyl-erythromycin A-(9E)-O-methoxymethyloxime To a stirred mixture of erythromycin A-(9E)-O-methoxymethyloxime (0.48 g, 0.605 mmol) and sodium hydrogen carbonate (0.056 g, 0.665 mmol) in DCM (10 mL) was added acetic anhydride (0.068 g, 0.665 mmol). After 16 h the mixture was concentrated and the residue purified by flash chromatography (silica gel, 0-10% methanol in DCM) to give the title compound as a white solid (0.44 g); ESMS m/z 835.8 [M+H]$^+$.

b) 2'-O-Acetyl-4"-O-propenoyl-erythromycin A-(9E)-methoxymethyloxime

A solution of Intermediate 21a (3.8 g, 4.55 mmol) dissolved in toluene (50 mL) and triethylamine was treated with 3-chloropropionyl chloride (0.54 mL, 5.7 mmol). After stirring for 24 h the mixture was diluted with EtOAc (100 mL) and washed with water (2×50 mL). The organic phase was separated, dried (MgSO$_4$), concentrated under reduced pressure and the residue purified by flash chromatography (silica gel, 0-8% methanol in DCM) to give the title compound as a white solid (3.17 g); ESMS m/z 888.9 [M+H]$^+$.

c) 4"-O-Propenoyl-erythromycin A-(9E)-O-methoxymethyloxime

A solution of Intermediate 21b (3.16 g, 3.55 mmol) in methanol (75 mL) was stirred at 55° C. for 16 h. The mixture was concentrated under reduced pressure and the residue purified by flash chromatography (silica gel, 0-10% methanol in DCM) to give the title compound as a white solid (1.78 g); ESMS m/z 847.9 [M+H]$^+$.

Intermediate 22:
4"-O-Allyl-6-O-methyl-erythromycin A

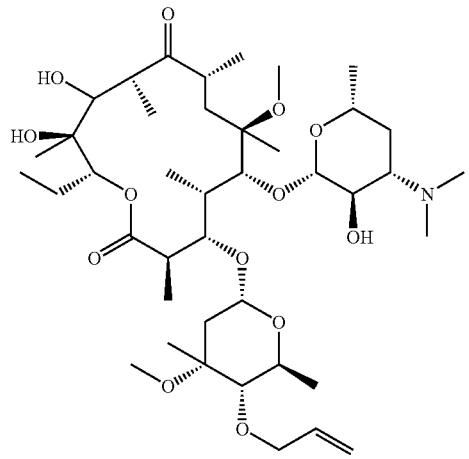

a) 4"-O-(1-Imidazol-1-yl-carbonyl)-6-O-methyl-erythromycin A

6-O-Methyl-erythromycin A (108 g, 0.144 mol) in dry THF (500 mL) under an atmosphere of argon was treated portionwise with carbonyldiimidazole (43.2 g, 0.267 mol) with ice bath cooling. After 1 h the cooling bath was removed. After 24 h additional THF (300 mL) was added to dissolve any solid material formed followed by the dropwise addition of water (500 mL). After stirring for 2.5 h a thick white precipitate had formed. The mixture was filtered under vacuum, washed with cold water (2×250 mL) and dried under vacuum to yield the title compound (100 g) as a white solid. The mother liquors yielded further title compound (12 g) after standing overnight; ESMS m/z 842.7 [M+H]$^+$.

b) 4"-O-(Allyloxycarbonyl)-6-O-methyl-erythromycin A

Intermediate 22a (50 g, 59.3 mmol) in DCM (200 mL) was cooled to 0° C. and treated with allyl alcohol (23.8 mL) and DBU (9.1 mL, 61 mmol). The reaction was stirred at 0° C. for 2.5 h and at 20° C. for 1.75 h. The reaction mixture was quenched with 3% aq citric acid (100 mL), the phases separated, and the organic phase washed with saturated sodium hydrogen carbonate and brine. After drying and evaporation to dryness, the residue was triturated with petroleum ether (bp 40-60° C.) to give the title compound as a white solid (41 g); ESMS m/z 832.6 [M+H]$^+$.

c) 4"-O-(Allyloxycarbonyl)-9-dihydro-9-methoxy-2', 11-bis-O-trimethylsilyl-9,12-anhydro-6-O-methyl-erythromycin A

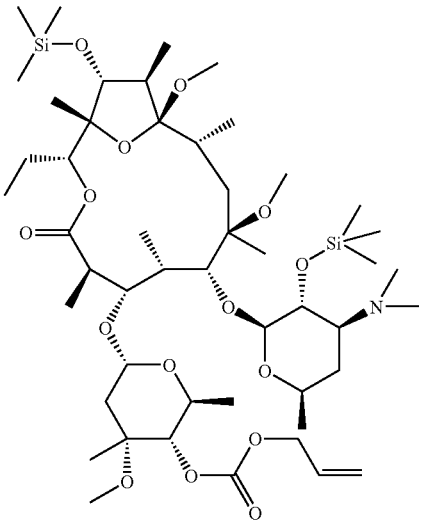

Intermediate 22b (41 g, 49.2 mmol) in dry pyridine (150 mL) under argon was treated dropwise with chlorotrimethylsilane (50 mL). The reaction was stirred at 20° C. for 6 h and left at 4° C. for 16 h. The reaction mixture was evaporated to dryness under reduced pressure and the residue taken up in methanol (200 mL).

After 80 min at 20° C., the solvent was removed by evaporation under reduced pressure and the residue taken up in diethyl ether and washed with saturated NaHCO$_3$. The phases were separated, the organic layer dried, and evaporated to dryness under reduced pressure. Toluene (two 500 mL portions) were added and evaporated under reduced pressure to give the crude title compound as a cream-coloured solid (41 g). To a solution of this material in dry pyridine (100 mL) was added chlorotrimethylsilane (30.0 mL). After 1.5 h the pyridine was evaporated, the residue dissolved in toluene and re-evaporated The resultant solid partitioned between diethyl ether (150 mL) and saturated sodium bicarbonate solution (sufficient aqueous was used to ensure a terminal pH=9). The aqueous layer was extracted with diethyl ether (150 mL) and the combined organics washed with water (150 mL) and brine (150 mL). Drying over sodium sulfate and evaporation yielded 46 g (94%) of a white solid. Crystallisation from acetonitrile (10.5 g from 100 mL) gave 5.2 g (50%) of a white solid; ESMS m/z 990.7 [M+H]$^+$.

d) 4"-O-Allyl-6-O-methyl-erythromycin A

The Intermediate 22c (15.0 g, 15.2 mmol) in dry THF (100 mL) under argon was treated with tetrakis(triphenylphosphine)palladium (0.36 g) and the resultant mixture heated at reflux for 1.5 h. Allyl t-butyl carbonate (5 mL) (F. Houlihan et al, Can. J. Chem. 1985, 63, 153) was added and heating continued for a further 3.75 h. After cooling and standing overnight at 20° C. the THF was evaporated and the dark brown residue taken up in 40/60 petroleum ether (100 mL). The solution was treated with charcoal, filtered and evaporated. The solid was then taken up in acetonitrile and re-evaporated and dried under vacuum overnight to yield 15.89 g. The product was dissolved in acetonitrile (25 mL) and 10% aqueous acetic acid (130 mL). After stirring at 20° C. for 6 h diethyl ether (50 mL) was added and the layers separated, the organic layer was extracted with water and the combined aqueous extracts made basic by the addition of potassium carbonate. The organic product was extracted with EtOAc (2×100 mL), dried and evaporated to give the title compound as a solid (11.5 g); ESMS m/z 946.7 [M+H]$^+$.

Intermediate 23:
4"-O-(2-oxoethyl)-6-O-methyl-erythromycin A

Intermediate 22 (95.8 g, 121 mmol) in DCM (1 L) and methanol was cooled to −78° C. and TFA (18 mL) added. Ozonized oxygen was bubbled through until a blue colour developed (1.25 h) Argon was bubbled through the mixture to flush out the ozone, then dimethyl sulfide (35 mL) and triethylamine (50.4 mL) were added. The reaction was stirred at −78° C. for 30 min then removed from the cooling bath. After 0.5 h the reaction was warmed to 0° C. in a water bath and stirred for a further 0.5 h.

The reaction mixture was washed with water (500 mL), dried (Na$_2$SO$_4$) and evaporated to dryness. The residue was dissolved in toluene and evaporated three times to give the title compound (103.7 g) which was used without purification; ES m/z 822.7 [M+MeOH+H]$^+$, 834.6 [M+HCO2]$^−$.

Intermediate 24: Ethyl-6-(3-methylaminopropyl)-1-(dimethylamino)-4-oxo-1,4-dihydro-3-quinolinecarboxylate a) Ethyl 3-(dimethylamino)-2-(2-fluoro-5-iodobenzoyl)-2-propenoate A stirred suspension of 2-fluoro-5-iodobenzoic acid (99.7 g) in DCM (1 L) at 20° C. was treated with oxalyl chloride (49.8 mL) and DMF (0.5 mL). After 3 h further DMF (0.1 mL) was added. After a further 2 h the clear solution was evaporated and re-evaporated from toluene (3×200 mL). The acid chloride was re-dissolved in toluene (1.5 L) and treated with triethylamine (79.2 mL) and ethyl 3-(dimethylamino)acrylate (65.3 g). After stirring for 2.5 h at 90° C. the mixture was filtered and evaporated. The residue was redissolved in EtOAc, washed with saturated sodium hydrogen carbonate solution (2×), water, saturated brine, dried (MgSO$_4$) and treated with decolourising charcoal for 0.5 h. The mixture was filtered, evaporated, redissolved in diethyl ether and allowed to crystallise. The solid was filtered off washed with diethyl ether and dried to give the title compound (91.2 g). On concentration and seeding a second crop was obtained (9.0 g); APCI m/z 391.9 [M+H]$^+$.

b) Ethyl 1-(dimethylamino)-6-iodo-4-oxo-1,4-dihydro-3-quinolinecarboxylate

A stirred suspension of Intermediate 24a (50 g) in EtOH (500 mL) was treated with 1,1-dimethylhydrazine (10.7 mL). After stirring for 2.5 h the clear solution was evaporated. The residue was dissolved in DMF (500 mL), treated with potassium carbonate (26.5 g) and the mixture stirred at 70° C. for 2 h. After cooling to 20° C. the mixture was poured into water containing excess citric acid, the solid filtered off, washed with water and dried to give the title compound (48.07 g); APCI m/z 387.0 [M+H]$^+$.

c) Ethyl 6-(3-t-butoxycarbonylmethylaminopropyn-1-yl)-1-(dimethylamino)-4-oxo-1,4-dihydro-3-quinolinecarboxylate A stirred mixture of Intermediate 24b (48.07 g) and copper (I) iodide (2.36 g) in triethylamine (510 mL) and MeCN (1 L) was degassed and covered with argon. After 15 min N-t-butoxycarbonyl-N-methylpropargylamine (31.72 g) and dichlorobis(triphenylphosphine)palladium (II) (2.8 g) were added. After 1.5 h the mixture was evaporated and redissolved in DCM. The solution was washed with saturated sodium hydrogen carbonate solution (2×), water, saturated brine, dried (Na$_2$SO$_4$) and evaporated. The residue was triturated with diethyl ether. The solid was filtered off washed with diethyl ether and dried, then boiled in EtOAc, filtered, the solution diluted with diethyl ether and allowed to crystallise to give the title compound (13.88 g). The solid insoluble in hot EtOAc and the evaporated mother liquors were combined and boiled in ethanol with decolourising charcoal. The hot mixture was filtered and evaporated to give more of the title compound (32.57 g); ESMS m/z 428.3 [M+H]$^+$.

d) Ethyl 6-(3-t-butoxycarbonylmethylaminopropyl)-1-(dimethylamino)-4-oxo-1,4-dihydro-3-quinolinecarboxylate A solution of Intermediate 24c (32.57 g) in DCM (300 mL) was treated with 10% Pd/C (2 g) and stirred for 1 min. The catalyst was filtered off and replaced with fresh (2 g). The mixture was hydrogenated at ambient temperature and pressures overnight, filtered and evaporated. The residue was triturated with ether. The solid was filtered off washed with ether and dried to give the title compound (26.33 g). The ether solution was evaporated, redissolved in EtOH and treated with decolourising charcoal. Filtration, evaporation and trituration with diethyl ether gave a second crop (3.96 g); ESMS m/z 432.2 [M+H]$^+$.

e) Ethyl-6-(3-methylaminopropyl)-1-(dimethylamino)-4-oxo-1,4-dihydro-3-quinolinecarboxylate A stirred solution of Intermediate 24d (30.29 g) in DCM (120 mL) was treated with 4M HCl in 1,4-dioxan (120 mL). After 1 h the mixture was evaporated and the residue partitioned between DCM and 10% K$_2$CO$_3$ solution. The DCM solution was collected, washed with saturated brine, dried (Na$_2$SO$_4$) and evaporated. The gummy solid was triturated with diethyl ether and diluted portionwise with light petroleum 40-60. The solid was filtered off, washed with light petroleum 40-60 and dried to yield the title compound (19 g); ESMS m/z 332.1 [M+H]$^+$.

Intermediate 25: 7-(3-Aminopropoxy)-1-dimethylamino-4-oxo-1,4-dihydroquinoline-3-carboxylic acid hydrochloride a) Ethyl 7-(3-t-butoxycarbonylaminopropoxy)-1-dimethylamino-4-oxo-1,4-dihydro-quinoline-3-carboxylate A stirred mixture of Intermediate 12c (1.07 g), t-butyl 3-hydroxypropylcarbamate (0.75 g) and triphenylphosphine (1.32 g) in dry THF (20 mL) under argon was treated with diisopropyl azodicarboxylate (0.98 mL) and stirred overnight. The solution was evaporated under reduced pressure and the residue redissolved in EtOAc, washed with 5% sodium carbonate solution (2×) and water (2×), dried (Na$_2$SO$_4$), evaporated under reduced pressure and flash chromatographed (silica gel, 30 to 50% EtOAc in DCM then 5% methanol in DCM) to give the title compound as a white solid (1.54 g); APCI m/z 434.1 [M+H]$^+$.

b) 7-(3-t-Butoxycarbonylaminopropoxy)-1-dimethylamino-4-oxo-1,4-dihydro-quinoline-3-carboxylic acid Intermediate 25a (1.53 g) was suspended in methanol (10 mL) and treated with 1M aqueous sodium hydroxide (5.3 mL). The mixture was stirred overnight. The solution was evaporated to low volume under reduced pressure and acidified with 5% citric acid. The solid was filtered, off washed with water and dried to give the title compound as a white solid (1.4 g); APCI m/z 406.1 [M+H]$^+$.

c) 7-(3-Aminopropoxy)-1-dimethylamino-4-oxo-1,4-dihydro-quinoline-3-carboxylic acid A solution of Intermediate 25b (1.4 g) in DCM (10 mL) was treated with 4M HCl in 1,4-dioxan (5 mL). After 2 h the solid was filtered off, washed with acetone and dried to give the title compound as a white solid (1.16 g); APCI m/z 306.1 [M+H]$^+$.

Intermediate 26: 6-[3-(2-Amino-ethoxy)-propyl]-1-dimethylamino-4-oxo-1,4-dihydro-quinoline-3-carboxylic acid trifluoroacetate a) (2-Prop-2-ynyloxy-ethyl)-carbamic acid tert-butyl ester

To a solution of (2-hydroxy-ethyl)-carbamic acid tert-butyl ester (1.56 g) in DCM (25 mL) benzyltrimethylammonium chloride (0.18 g) was added. To this solution aqueous 50% NaOH (30 g) and propargyl bromide (1.05 mL of 80% solution in toluene) were added and the mixture was vigorously stirred at room temperature for 3 h. Phases were diluted and separated; the organic phase was washed with water (2×15 mL), dried and evaporated under reduced pressure. The residue was purified by chromatography (silica gel, 0-5% methanol in DCM) to give the title compound as a pale-orange oil (1.53 g); ESMS m/z 222.4 [M+Na]$^+$.

b) 6-[3-(2-tert-Butoxycarbonylamino-ethoxy)-prop-1-ynyl]-1-dimethylamino-4-oxo-1,4-dihydro-quinoline-3-carboxylic acid ethyl ester Intermediate 1c (0.79 g) and copper (I) iodide (0.020 g) were suspended in a mixture of CH$_3$CN (30 mL) and triethylamine (6 mL); the suspension was degassed bubbling nitrogen for 30 min. Intermediate 26a (0.73 g) and dichlorobis(triphenylphospine)palladium (II) (0.046 g) were added under nitrogen and the mixture was heated under reflux. After 2 h the solvents were removed under reduced pressure and the residue was dissolved in DCM (20 mL) and extracted with aqueous 20% citric acid (2×15 mL). The organic phase was dried and evaporated under reduced pressure. The residue was purified by chromatography (silica gel, 0-2% methanol in DCM) to give the title compound (0.93 g); ESMS m/z 458.6 [M+H]$^+$.

c) 6-[3-(2-tert-Butoxycarbonylamino-ethoxy)-propyl]-1-dimethylamino-4-oxo-1,4-dihydro-quinoline-3-carboxylic acid ethyl ester Intermediate 26b (0.93 g) was dissolved in DCM (25 mL) and 10% palladium on carbon (0.10 g) was added. The mixture was hydrogenated at room temperature at 20 psi of hydrogen for 2 h. The catalyst was filtered and the solvent evaporated under reduced pressure to give the title compound (0.93 g); ESMS m/z 462.1 [M+H]$^+$.

d) 6-[3-(2-tert-Butoxycarbonylamino-ethoxy)-propyl]-1-dimethylamino-4-oxo-1,4-dihydro-quinoline-3-carboxylic acid A solution of Intermediate 26c (0.93 g) and potassium hydroxide (0.57 g) in a mixture of dioxane (25 mL) and water (5 mL) was stirred overnight at room temperature. Dioxane was removed under reduced pressure and the aqueous solution was acidified and extracted with DCM (2×15 mL). The organic phase was dried and evaporated under reduced pressure to give the title compound (0.90 g) as a white solid; ESMS m/z 434.2 [M+H]$^+$.

e) 6-[3-(2-Amino-ethoxy)-propyl]-1-dimethylamino-4-oxo-1,4-dihydro-quinoline-3-carboxylic acid trifluoroacetate A solution of Intermediate 26d (0.9 g) in DCM (5 mL) was treated with TFA (3 mL) and stirred at room temperature for 2 h. The solvent was evaporated under reduced pressure; the residue was re-evaporated from DCM (2×) and triturated with isopropylether to give the title compound as a solid (0.75 g); ESMS m/z 334.0 [M+H]$^+$.

Intermediate 27: 6-[2-(2-Amino-ethoxy)-ethylsulfanyl]-1-dimethylamino-4-oxo-1,4-dihydro-quinoline-3-carboxylic acid trifluoroacetate a) [2-(2-Hydroxy-ethoxy)-ethyl]-carbamic acid tert-butyl ester

To a solution of 2-(2-amino-ethoxy)-ethanol (5.00 g) in water (35 mL) at 0° C. potassium hydroxide (2.93 g) was added. To this mixture maintained at 0° C., a solution of di-tert-butyldicarbonate (11.40 g) in dioxane (17 mL) was added dropwise. The resulting mixture was stirred at 0° C. for 1 h and then 4 h at room temperature. Dioxane was evaporated under reduced pressure and the aqueous solution was extracted with DCM (2×25 mL). The organic phase was dried and evaporated under reduced pressure. The residue was purified by flash chromatography (silica gel, EtOAc/petroleum ether 40/60 to 60/40) to give the title compound (8.50 g); ESMS m/z 205.3 [M+H]$^+$.

b) Toluene-4-sulfonic acid 2-(2-tert-butoxycarbonylamino-ethoxy)-ethyl ester Intermediate 27a (7.39 g) was dissolved in DCM (75 mL) and to the solution triethylamine (5.00 mL) and p-toluensulfonyl chloride (6.87 g) were added at 0° C. The resulting solution was stirred at room temperature overnight. The suspension was filtered off and the organic phase was evaporated under reduced pressure. The residue was purified by chromatography (silica gel, EtOAc/petroleum ether from 20/80 to 40/60) to give the title compound (11.25 g); ESMS m/z 360.4 [M+H]$^+$.

c) Thioacetic acid S-[2-(2-tert-butoxycarbonylamino-ethoxy)-ethyl]ester

To a solution of Intermediate 27b (11.69 g) in acetone (250 mL) potassium thioacetate (7.42 g) was added; the resulting suspension was refluxed for 2 h. The solid was filtered and washed with acetone. The solution was evaporated under reduced pressure and the residue was purified by filtration on a short silica pad (EtOAc/petroleum ether 20/80) to obtain the title compound (6.85 g); ESMS m/z 264.4 [M+H]+.

d) 6-[2-(2-tert-Butoxycarbonylamino-ethoxy)-ethyl-sulfanyl]-1-dimethylamino-4-oxo-1,4-dihydro-quinoline-3-carboxylic acid A suspension of Intermediate 1c (0.70 g), Intermediate 27c (0.48 g), copper (I) iodide (0.020 g), potassium carbonate (0.51 g) and ethylene glycol (0.21 mL) in absolute ethanol (10 mL) was degassed bubbling nitrogen for 0.5 h. The mixture was then heated in a sealed tube at 120° C. for 1 h under microwave irradiation. The mixture was acidified with 20% aqueous citric acid and extracted with EtOAc. The organic phase was dried and evaporated under reduced pressure. The residue was purified by chromatography (silica gel, 0-10% methanol in DCM). The residue, still containing disulfide dimer of Intermediate 27c, was dissolved in DCM/triethylamine mixture and shaken overnight in the presence of polymer supported thiophenol. The polymer was filtered and the solvents removed under reduced pressure to give the title compound (0.60 g); ESMS m/z 452.1 [M+H]+.

e) 6-[2-(2-Amino-ethoxy)-ethylsulfanyl]-1-dimethylamino-4-oxo-1,4-dihydro-quinoline-3-carboxylic acid trifluoroacetate A solution of Intermediate 27d (0.60 g) in DCM (5 mL) was treated with TFA (3 mL) and stirred at room temperature for 2 h. The solvent was evaporated under reduced pressure; the residue was re-evaporated from DCM (2×) and triturated with isopropylether to give the title compound as a solid (0.42 g); ESMS m/z 352.1 [M+H]+.

Intermediate 28: 2'-O-Acetyl-4"-O-(imidazol-1-yl-carbonyl)-erythromycin A-(9E)-O-methyloxime To a solution of Intermediate 5a (0.50 g) in dry THF (20 mL) 4-dimethylaminopyridine (0.38 g) and carbonyl diimidazole (0.50 g) were added; the resulting mixture was stirred under nitrogen at room temperature for 6 h. To the solution EtOAc and 5% aqueous KH$_2$PO$_4$ were added (50 mL each) and the phases were separated. The organic phase was dried and evaporated under reduced pressure to give the title compound (0.50 g) as white foam; ESMS m/z 899.8 [M+H]+.

Intermediate 29: 2'-O-Acetyl-4"-O-(imidazol-1-yl-carbonyl)-erythromycin A-(9E)-O-methoxymethyloxime To a solution of Intermediate 21a (1.10 g) in dry THF (40 mL) 4-dimethylaminopyridine (0.80 g) and carbonyl diimidazole (1.10 g) were added; the resulting mixture was stirred under nitrogen at room temperature for 6 h. To the solution EtOAc and 5% aqueous KH$_2$PO$_4$ were added (100 mL each) and the phases were separated. The organic phase was dried and evaporated under reduced pressure to give the title compound (1.10 g) as white foam; ESMS m/z 929.9 [M+H]+.

Intermediate 30: 2'-O-Acetyl-4"-O-(imidazol-1-yl-carbonyl)-(9S)-9-O,11-O-ethylidene-9-dihydroerythromycin A a) 2'-O-Acetyl-(9S)-9-O,11-O-ethylidene-9-dihydro-erythromycin A

To a solution of (9S)-9-O,11-O-ethylidene-9-dihydro-erythromycin A (0.95 g) in DCM (30 mL) NaHCO$_3$ (0.16 g) was added followed by acetic anhydride (0.18 mL). After stirring overnight at room temperature the mixture was diluted with DCM and washed with 5% aqueous NaHCO$_3$. The organic layer was separated, dried and evaporated under reduced pressure to yield the title compound (1.0 g) as a solid; ESMS m/z 804.4 [M+H]+.

b) 2'-O-Acetyl-4"-O-(imidazol-1-yl-carbonyl)-(9S)-9-O,11-O-ethylidene-9-dihydroerythromycin A To a solution of Intermediate 30a (1.0 g) in dry THF (30 mL) 4-dimethylaminopyridine (0.80 g) and carbonyl diimidazole (1.0 g) were added; the resulting mixture was stirred under nitrogen at room temperature for 6 h. To the solution EtOAc and 5% aqueous KH$_2$PO$_4$ were added (100 mL each) and the phases were separated. The organic phase was dried and evaporated under reduced pressure to give the title compound (1.10 g) as white foam; ESMS m/z 898.6 [M+H]+.

Intermediate 31: 2'-O-Acetyl-4"-O-(imidazol-1-yl-carbonyl)-erythromycin A-9-O-(1-methoxy-1-methylethyl)-oxime a) 2'-O-Acetyl-erythromycin A-9-O-(1-methoxy-1-methylethyl)-oxime

To a solution of erythromycin A-9-O-(1-methoxy-1-methylethyl)-oxime (0.86 g) in DCM (15 mL) NaHCO$_3$ (0.13 g) was added followed by acetic anhydride (0.15 mL). After stirring overnight at room temperature the mixture was diluted with DCM and washed with 5% aqueous NaHCO$_3$. The organic layer was separated, dried and evaporated under reduced pressure to yield the title compound (0.90 g) as a solid; ESMS m/z 863.4 [M+H]+.

b) 2'-O-Acetyl-4"-O-(imidazol-1-yl-carbonyl)-erythromycin A-(9E)-O-(1-methoxy-1-methylethyl)-oxime To a solution of Intermediate 31a (0.90 g) in dry THF (25 mL) 4-dimethylaminopyridine (0.70 g) and carbonyl diimidazole (0.90 g) were added; the resulting mixture was stirred under nitrogen at room temperature for 6 h. To the solution EtOAc and 5% aqueous KH$_2$PO$_4$ were added (100 mL each) and the phases were separated. The organic phase was dried and evaporated under reduced pressure to give the title compound (0.95 g) as white foam; ESMS m/z 957.4 [M+H]+.

Intermediate 32: 2'-O-Acetyl-4"-O-(imidazol-1-yl-carbonyl)-erythromycin A-(9E)-O-(2-diethylaminoethyl)-oxime a) 2'-O-Acetyl-erythromycin A-(9E)-O-(2-diethylaminoethyl)-oxime

To a solution of erythromycin A-(9E)-O-(2-diethylaminoethyl)-oxime (4.05 g) in DCM (50 mL) NaHCO$_3$ (0.60 g) was added followed by acetic anhydride (0.68 mL). After stirring overnight at room temperature the mixture was diluted with DCM and washed with 5% aqueous NaHCO$_3$. The organic layer was separated, dried and evaporated under reduced pressure to yield the title compound (4.1 g) as a solid; ESMS m/z 890.3 [M+H]+.

b) 2'-O-Acetyl-4"-O-(imidazol-1-yl-carbonyl)-erythromycin A-(9E)-O-(2-diethylaminoethyl)-oxime To a solution of Intermediate 32a (3.7 g) in dry THF (125 mL) 4-dimethylaminopyridine (2.54 g) and carbonyl diimidazole (3.37 g) were added; the resulting mixture was stirred under nitrogen at room temperature for 6 h. The solvent was removed under reduced pressure and the residue was dissolved in EtOAc (150 mL) and extracted with 5% aqueous $KH_2PO_4$ (2×100 mL) and brine (100 mL). The organic phase was dried and evaporated under reduced pressure to give the title compound (4.1 g) as white foam; ESMS m/z 984.3 $[M+H]^+$.

Intermediate 33: 2'-O-Acetyl-4"-O-(imidazol-1-yl-carbonyl)-erythromycin A-(9E)-O-cyanomethyloxime a) Erythromycin A-(9E)-O-cyanomethyloxime

To a solution of erythromycin A-(9E)-oxime (3.0 g) in dry THF (120 mL) a solution of tetrabutylammonium hydroxide 1M in methanol (4.4 mL) was added at room temperature. After 5 min chloroacetonitrile (0.38 mL) was added dropwise and the resulting mixture was heated at 50° C. for 1 h. The solvent was removed under reduced pressure and the residue was dissolved in diethyl ether and extracted with brine (3×75 mL); the organic phase was dried and evaporated under reduced pressure. The residue was purified by flash chromatography (silica gel, 0-3% of 9/1 methanol/20M ammonia in DCM) to give the title compound (2.27 g) as a solid; ESMS m/z 788.4 $[M+H]^+$.

b) 2'-O-Acetyl-erythromycin A-(9E)-O-cyanomethyloxime

To a solution of Intermediate 33a (2.24 g) in DCM (50 mL) $NaHCO_3$ (0.36 g) was added followed by acetic anhydride (0.40 mL). After stirring overnight at room temperature the mixture was diluted with DCM and washed with 5% aqueous $NaHCO_3$. The organic layer was separated, dried and evaporated under reduced pressure to yield the title compound (2.35 g) as a solid; ESMS m/z 830.4 $[M+H]^+$.

c) 2'-O-Acetyl-4"-O-(imidazol-1-yl-carbonyl)-erythromycin A-(9E)-O-cyanomethyloxime To a solution of Intermediate 33b (2.35 g) in dry THF (90 mL) 4-dimethylaminopyridine (1.73 g) and carbonyl diimidazole (2.30 g) were added; the resulting mixture was stirred under nitrogen at room temperature for 6 h. The solvent was removed under reduced pressure and the residue was dissolved in EtOAc (150 mL) and extracted with 5% aqueous $KH_2PO_4$ (2×100 mL) and brine (100 mL). The organic phase was dried and evaporated under reduced pressure to give the title compound (2.65 g) as white foam; ESMS m/z 924.4 $[M+H]^+$.

Intermediate 34: 4"-O-Propenoyl-erythromycin A-(9E)-O-2-(N-morpholino)ethyloxime a) Erythromycin A-(9E)-O-2-(N-morpholino)ethyloxime

To a stirred suspension of sodium hydride (0.80 g of a 60% dispersion in oil equivalent to 20 mmol) in dry DMF (20 mL) was added a solution of erythromycin A (9E)-oxime (7.49 g, 10 mmol) in dry DMF (40 mL). After hydrogen evolution had ceased 2-(N-morphilino)chloroethane hydrochloride (1.72 g, 9.3 mmol) was added in one portion. The resultant mixture was stirred at 50° C. for 1.5 h, cooled and allowed to stand overnight at room temperature. Quenching with water (100 mL) gave a white precipitate which was filtered and dried to yield the title compound (5.39 g); ESMS m/z 862.7 $[M+H]^+$.

b) 2'-O-Acetyl-erythromycin A-(9E)-O-2-(N-morpholino) ethyloxime

A solution of Intermediate 34a (0.29 g, 0.336 mmol) dissolved in DCM (5 mL) was treated with acetic anhydride (57.5 uL, 0.422 mmol). After stirring for 18 h at room temperature the mixture was partitioned between DCM (25 mL) and water. The mixture was made alkaline, pH 9, with 2M sodium hydroxide. The organic layer was separated, washed, dried and evaporated under reduced pressure to yield the title compound (0.285 g); $\delta_H$ (400 MHz; $CD_3OD$) inter alia 2.03 (3H, s); ESMS m/z 453.1 $[M+2H]^{++}$.

c) 2'-O-Acetyl-4"-O-propenoyl-erythromycin A-(9E)-O-2-(N-morpholino) ethyloxime A solution of Intermediate 34b (0.253 g, 0.28 mmol) dissolved in toluene (5 mL) and triethylamine (0.1 mL, 0.72 mmol) was treated with 3-chloropropionyl chloride (0.033 mL, 0.35 mmol). After stirring at room temperature for 16 h triethylamine (0.2 mL, 1.44 mmol) and chloropropionyl chloride (0.066 mL, 0.7 mmol) were added and the reaction stirred for a further 16 h. The mixture was quenched with saturated sodium hydrogen carbonate and the organic layer separated, dried and evaporated under reduced pressure to yield the crude product. Chromatography on silica gel eluting with 0-7% (9:1 MeOH/0.880 $NH_3$) in DCM gave the title compound (0.048 g); $\delta_H$ (400 MHz; $CD_3OD$) inter alia 2.03 (3H, s), 5.96 (1H, dxd, J=10.4 & 1.6 Hz), 6.18 (1H, dxd, J=17.2 & 10.4 Hz), 6.42 (1H, dxd, J=17.2 & 1.6 Hz); ESMS m/z 958.7 $[M+H]^+$.

d) 4"-O-Propenoyl-erythromycin A-(9E)-O-2-(N-morpholino)ethyloxime

A solution of Intermediate 34c (0.048 g, 0.05 mmol) in methanol (5 mL) was stirred at 50° C. for 18 hours. The mixture was concentrated under reduced pressure to give the title compound as a white solid (0.043 g); ESMS m/z 916.8 $[M+H]^+$.

Intermediate 35: 2'-O-Acetyl-4"-O-allyl-azithromycin 11,12-carbonate

2'-O-Acetyl-azithromycin-11,12-carbonate (67.82 g, 83 mmol) in dry THF (600 mL) was treated with allyl t-butyl-carbonate (50 g, 0.315 mol) and tetrakis(triphenylphosphine) palladium (1.5 g 1.3 mmol). The resultant mixture was heated at 75° C. under argon. After 16 h the reaction was cooled, evaporated under reduced pressure and the residue purified by chromatography on silica eluting with 0-10% (9:1 MeOH/0.880 $NH_3$) in DCM gave the title compound (48 g); ESMS m/z 857.7 $[M+H]^+$.

Intermediate 36: 4"-O-Propenoyl-erythromycin A-(9E)-O-2-(N,N-diethylamino)ethyloxime a) Erythromycin A-(9E)-O-2-(N,N-diethylamino)ethyloxime

To a solution of erythromycin A (9E)-O-oxime (2.5 g, 3.33 mmol) in THF (25 mL) and water (5 drops) was added 2-N,N-diethylaminoethyl chloride hydrochloride (1.14 g, 6.66 mmol) and sodium carbonate (1.4 g, 13.3 mmol). After heating under reflux for 24 h the mixture was cooled and partitioned between EtOAc and water. The organic layer was separated and the aqueous phase extracted with DCM. The combined organic phases were dried and evaporated under reduced pressure to yield a pale yellow solid. Chromatography on silica gel eluting with 0-7% (9:1 MeOH/0.880 NH$_3$) in DCM gave the title compound (0.52 g); ESMS m/z 848.9 [M+H]$^+$.

b) 2'-O-Acetyl-erythromycin A-(9E)-O-2-(N,N-diethylamino)ethyloxime

To a solution Intermediate 36a (0.52 g, 0.61 mmol) in DCM (10 mL) was added acetic anhydride (0.078 mL, 0.766 mmol). After stirring at room temperature for 14 h the mixture was diluted with DCM and washed with 2M sodium hydroxide solution. The organic was separated, dried and evaporated under reduced pressure to yield the title compound (0.575 g); ESMS m/z 890.9 [M+H]$^+$.

c) 2'-O-Acetyl-4''-propenyl-erythromycin A-(9E)-O-2-(N,N-diethylamino)ethyloxime A solution of Intermediate 36b (0.185 g, 0.21 mmol) dissolved in toluene (8 mL) and triethylamine (0.087 mL, 0.62 mmol) was treated with 3-chloropropionyl chloride (0.03 mL, 0.312 mmol). After stirring at room temperature for 16 h triethylamine (0.087 mL, 0.62 mmol) and chloropropionyl chloride (0.03 uL, 0.132 mmol) were added and the reaction stirred for a further 3 h. The mixture was quenched with saturated sodium hydrogen carbonate and the organic layer separated, dried and evaporated under reduced pressure to yield the crude product. Chromatography on silica gel eluting with 0-10% (9:1 MeOH/0.880 NH$_3$) in DCM gave the title compound (0.196 g); ESMS m/z 944.8 [M+H]$^+$.

d) 4''-Propenyl-erythromycin A-(9E)-O-2-(N,N-diethylamino)ethyloxime

A solution of Intermediate 36c (0.21 g, 0.22 mmol) in methanol (15 mL) was stirred at 55° C. After 16 h the mixture was evaporated under reduced pressure and the crude product purified by chromatography over silica gel eluting with 0-11% (9:1 MeOH/0.880 NH$_3$) in DCM gave the title compound (0.17 g); ESMS m/z 902.6 [M+H]$^+$.

Intermediate 37: 6-(3-(Cyclopropylamino)prop-1-yl)-1,4-dihydro-1-dimethylamino-4-oxo-quinoline-3-carboxylic acid ethyl ester a) 6-(3-Hydroxypropyn-1-yl)-1,4-dihydro-1-dimethylamino-4-oxo-quinoline-3-carboxylic acid ethyl ester Intermediate 1c (15.0 g) and copper (I) iodide (0.74 g) in dry acetonitrile (300 mL) and triethylamine (250 mL) were degassed and covered with Argon. Dichlorobis(triphenylphosphine)palladium (II) (0.87 g) and propargyl alcohol (3.4 mL) were added. The mixture was stirred under argon for 30 min. The reaction mixture was evaporated under reduced pressure and triturated with EtOAc. The solid material was filtered off, washed with EtOAc and dried, then taken up in ethanol and DCM and stirred with charcoal for 30 min. The filtered solution was evaporated under reduced pressure to yield the title compound as a solid (10.8 g); ESMS m/z 315.0 [M+H]$^+$.

b) 6-(3-Hydroxyprop-1-yl)-1,4-dihydro-1-dimethylamino-4-oxo-quinoline-3-carboxylic acid ethyl ester Intermediate 37a (10.8 g) in DCM (500 mL) was hydrogenated at 20° C. and 1 atm over 10% palladium on carbon (1.0 g). After 16 h the catalyst was filtered off and washed well with DCM. The combined filtrates were rehydrogenated at 20° C. and 1 atm over 10% palladium on carbon (1.0 g). After a further 20 h the catalyst was filtered off and washed well with DCM. The combined filtrates were evaporated under reduced pressure to dryness to give the title compound (10.01 g); ESMS m/z 319.1 [M+H]$^+$.

c) 6-(3-Oxoprop-1-yl)-1,4-dihydro-1-dimethylamino-4-oxo-quinoline-3-carboxylic acid ethyl ester To a stirred solution of oxalyl chloride (4.4 mL) in DCM (100 mL) at –78 C was treated with dimethyl sulfoxide (4.47 mL) in DCM (10 mL). After 15 min Intermediate 37b (8.03 g) in DCM (10 mL) was added over 5 min. The reaction was stirred at –78° C. for 1.5 h, then triethylamine (17.5 mL) was added and the reaction warmed to 0° C. Brine was added and the organic layer collected, washed with more brine, dried (Na$_2$SO$_4$) and evaporated under reduced pressure to give the title compound (8.1 g); $\delta_H$ (250 MHz; CDCl3) 1.43 (3H, t, J=7.1 Hz), 2.87 (2H, t, J=7.3 Hz), 2.92 (6H, s), 3.09 (2H, t, J=7.3 Hz), 4.41 (2H, q, J=7.1 Hz), 7.55 (1H, dd, J=2.0 & 8.8 Hz), 8.02 (1H, d, J=8.8 Hz), 8.28 (1H, d, J=2.0 Hz), 8.74 (1H, s), 9.84 (1H, t, J=1.1 Hz).

d) 6-(3-(Cyclopropylamino)prop-1-yl)-1,4-dihydro-1-dimethylamino-4-oxo-quinoline-3-carboxylic acid ethyl ester Intermediate 37b (0.8 g) and cyclopropylamine (0.87 mL) in DCM (10 mL) was treated with 1 A molecular sieves (1 g). After stirring for 30 min sodium triacetoxyborohydride (1.1 g) was added followed after 5 min by acetic acid (26 drops). After 1 h the solution was decanted from the sieves, washed twice with saturated sodium hydrogen carbonate and with brine, dried (Na$_2$SO$_4$) and evaporated under reduced pressure. The residue was purified by chromatography on silica gel eluting with 4-8% (9:1 MeOH/0.880 NH$_3$) in DCM gave the title compound (0.566 g); ESMS m/z 358.1 [M+H]$^+$.

Intermediate 38 4''-O-Allyl Erythromycin A-(9E)-(cyanomethyl)oxime a) Erythromycin A-(9E)-(1-isopropoxycyclohex-1-yl)oxime Erythromycin (9E)-oxime hydrochloride (US2003/0023053A1) (10.2 g) in DCM (100 mL) at 5° C. was treated with 1,1-diisopropoxycyclohexane (15.1 mL) and pyridinium bromide (0.05 g). After 15 min the cooling bath was removed and the reaction stirred for a further 1 h. The solution was washed with 5% aq. sodium hydrogen carbonate, dried (Na$_2$SO$_4$) and evaporated under reduced pressure. Chromatography on silica eluting with 0-8% (9:1 MeOH/0.880 ammonia) in DCM gave the title compound as a white foam (9.76 g); ES m/z 889.7 [M+H]$^+$.

b) 2'-O-Acetyl-erythromycin A-(9E)-(1-isopropoxycyclohex-1-yl)oxime

Intermediate 38a (9.76 g) and sodium hydrogen carbonate (1.1 g) in DCM (100 mL) was treated with acetic anhydride (1.24 mL). After stirring for 24 h the mixture was washed with water, dried (Na$_2$SO$_4$) and evaporated under reduced pressure to give the title compound as a white foam (9.95 g); ES m/z 931.8 [M+H]$^+$.

c) 2'-O-Acetyl-erythromycin A-(9E)-(1-isopropoxy-cyclohex-1-yl)oxime-11,12-carbonate Intermediate 38b (9.95 g) and pyridine (8.63 mL) in DCM (100 mL) at 0° C. was treated dropwise with a solution of triphosgene (3.18 g) in DCM (20 mL). After 1 h, the mixture was evaporated under reduced pressure and the residue dissolved in EtOAc washed with saturated aq. sodium hydrogen carbonate, brine, dried (Na$_2$SO$_4$) and evaporated under reduced pressure. The residue was taken up in MeOH/Toluene and evaporated under reduced pressure to remove pyridine. Chromatography on silica eluting with 0-10% (9:1 MeOH/0.880 ammonia) in DCM gave the title compound as a white foam (8.87 g); ES m/z 957.6 [M+H]$^+$.

d) 2'-O-Acetyl-4"-O-allyl-erythromycin A-(9E)-(1-isopropoxycyclohex-1-yl)oxime-11,12-carbonate Intermediate 38c (9.87 g), allyl t-Butyl carbonate (2.45 g) and tetrakis(triphenylphosphine)palladium (0.36 g) in THF (150 mL) was refluxed under argon for 1 h. Further allyl t-Butyl carbonate (2.45 g) and tetrakis(triphenylphosphine) palladium (0.36 g) was added and the reflux continued. After a further 1 h, the reaction was cooled and evaporated under reduced pressure. Chromatography on silica eluting with 0-7% (9:1 MeOH/0.880 ammonia) in DCM gave the title compound as a white foam (9.8 g); ES m/z 997.9 [M+H]$^+$.

e) 4"-O-Allyl-erythromycin A-(9E)-(1-isopropoxy-cyclohex-1-yl)oxime-11,12-carbonate Intermediate 38d (9.38 g) in methanol (200 ml) was warmed to 55° C. for 16 h. The reaction was cooled and evaporated under reduced pressure. Chromatography on silica eluting with 2-8% (9:1 MeOH/0.880 ammonia) in DCM gave the title compound as a white foam (6.0 g); ES m/z 955.8 [M+H]$^+$.

f) 4"-O-Allyl-erythromycin A-(9E)-(1-isopropoxycyclohex-1-yl)oxime

Intermediate 38e (6.0 g) in acetonitrile (200 mL) and 10% aq potassium carbonate (80 mL) was refluxed for 12 h. After cooling the actonitrile was removed by evaporation under reduced pressure. The mixture was diluted with saturated brine and extracted with DCM. The extract was dried (Na$_2$SO$_4$) and evaporated under reduced pressure. Chromatography on silica eluting with 2-5% (9:1 MeOH/0.880 ammonia) in DCM gave the title compound as a white foam (4.59 g); ES m/z 929.8 [M+H]$^+$.

g) 4"-O-Allyl-erythromycin A-(9E)-oxime

Intermediate 38f (4.58 g) in methanol (30 mL), water (15 mL) and formic acid (1.5 mL) was heated at 40° C. for 4 h. The solvent was evaporated under reduced pressure and the residue partitioned between DCM and saturated aq. sodium hydrogen carbonate. The organic layer was dried (Na$_2$SO$_4$) and evaporated under reduced pressure. Chromatography on silica eluting with 3-8% (9:1MeOH/0.880 ammonia) in DCM gave the title compound as a white foam (2.44 g); ES m/z 789.7 [M+H]$^+$.

h) 4"-O-Allyl-erythromycin A-(9E)-(cyanomethyl) oxime

Intermediate 38g (2.44 g) and tetrabutylammonium bromide (0.1 g) in a rapidly stirred mixture of DCM (20 mL) and 2M sodium hydroxide (10 mL) was added chloroacetonitrile (0.3 mL). After 2 h the phases were separated and the aq extracted with DCM. The combined organic phases were washed with brine, dried and evaporated under reduced pressure. Chromatography on silica eluting with 2-8% (9:1 MeOH/0.880 ammonia) in DCM gave the title compound as a white foam (2.12 g); ES m/z 828.7 [M+H]$^+$.

Example 1

4"-O-{3-[3-(3-Carboxy-1,4-dihydro-1-dimethylamino-4-oxo-6-quinolinyl)propylamino]propionyl}-6-O-methyl-erythromycin A

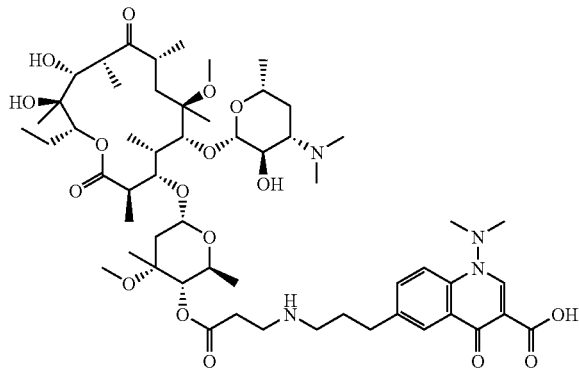

A mixture of Intermediate 8 (2.6 g) and Intermediate 1 (1.5 g) in DMSO (12 mL), water (8 drops) and triethylamine (1.92 mL) was heated at 80° C. for 12 h. The mixture was concentrated and the residue flash chromatographed on silica gel eluting with 0-14% (9:1 methanol/0.880 NH$_3$) in DCM to give the title compound as a buff solid (2.2 g); $\delta_H$ (400 MHz; CDCl$_3$) 0.84 (3H, t, J=7.0 Hz), 1.12 (18H, m), 1.19 (3H, d, J=6.0 Hz), 1.21 (3H, d, J=7.6 Hz), 1.24 (1H, m), 1.38 (3H, s), 1.49 (1H, m), 1.60-1.73 (3H, m), 1.79-1.96 (5H, m), 2.33 (6H, s), 2.42 (1H, d, J=14.9 Hz), 2.49-2.63 (4H, m), 2.68 (2H, t, J=7.0 Hz), 2.85 (2H, t, J=7.5 Hz), 2.90 (3H, m), 2.98 (6H, s), 3.00 (1H, m), 3.03 (3H, s), 3.18 (1H, s), 3.20 (1H, t, J=7.9 Hz), 3.30 (3H, s), 3.40 (1H, broad), 3.65 (1H, d, J=6.4 Hz), 3.72 (1H, m), 3.76 (1H, s), 3.77 (1H, d, J=9.8 Hz), 4.00 (1H, s), 4.34 (1H, m), 4.57 (1H, d, J=7.0 Hz), 4.68 (1H, d, J=9.5 Hz), 4.99 (1H, d, J=3.8 Hz), 5.06 (1H, d, J=10.7 Hz), 7.67 (1H, d, J=8.7 Hz), 8.18 (1H, d, J=8.6 Hz), 8.29 (1H, s), 9.03 (1H, s); ESMS m/z 1091.9 [M+H]$^+$.

Example 2

4"-O-{3-[3-(3-Carboxy-1,4-dihydro-1-dimethylamino-4-oxo-6-quinolinyl)propylamino]propionyl}-azithromycin-11,12-carbonate

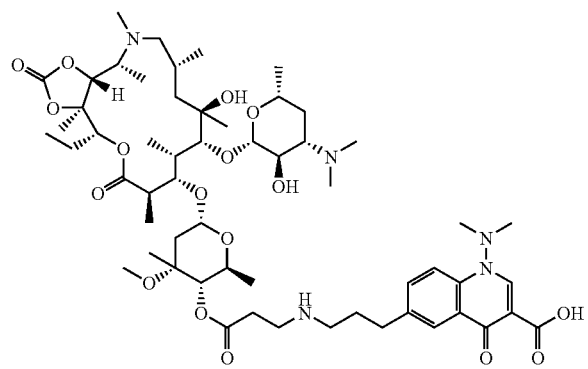

A mixture of Intermediate 10 (0.083 g) and Intermediate 1 (0.049 g) in DMSO (0.5 mL), water (1 drop) and triethylamine (0.03 mL) was heated at 80° C. for 42 h. The mixture was concentrated and the residue chromatographed on silica gel eluting with 0-16% (9:1 MeOH/0.880 NH$_3$) in DCM to give the title compound as a white solid (0.073 g); ESMS m/z 1118.9 [M+H]$^+$.

Example 3

4"-O-{3-[3-(3-Carboxy-1,4-dihydro-1-(morpholin-4-yl)-4-oxo-6-quinolinyl)propylamino]propionyl}-6-O-methyl-erythromycin A

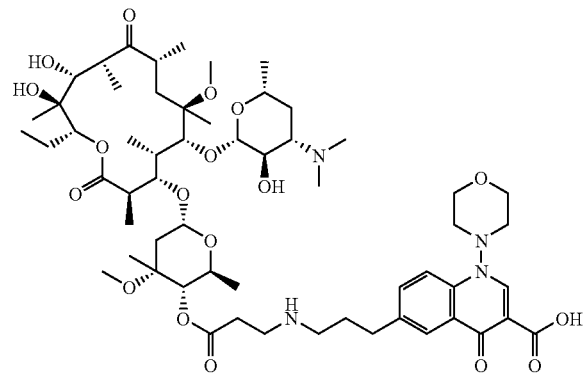

A mixture of Intermediate 8 (0.080 g) and Intermediate 2 (0.055 g) in DMSO (0.5 mL), water (1 drop) and triethylamine (0.03 mL) was heated at 80° C. for 88 h. The mixture was concentrated and the residue chromatographed on silica gel eluting with 0-20% (9:1 MeOH/0.880 NH$_3$) in DCM. Purification by mass directed automatic preparative HPLC, followed by freeze drying from dilute aqueous ammonia, gave the title compound as a white solid (0.023 g); ESMS m/z 1133.9 [M+H]$^+$.

Example 4

4"-O-{3-[3-(3-Carboxy-1,4-dihydro-1-methylamino-4-oxo-6-quinolinyl)propylamino]propionyl}-6-O-methyl-erythromycin A

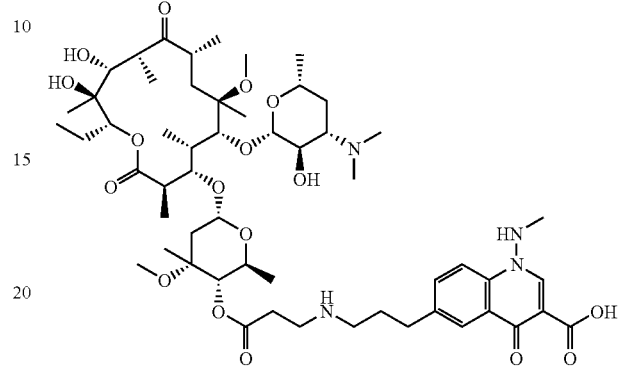

A mixture of Intermediate 8 (0.080 g) and Intermediate 3 (0.059 g) in DMSO (0.5 mL), water (1 drop) and triethylamine (0.03 mL) was heated at 80° C. for 40 h. The mixture was concentrated and the residue chromatographed on silica gel eluting with 0-20% (9:1 MeOH/0.880 NH$_3$) in DCM to give the title compound as a buff solid (0.036 g); ESMS m/z 1077.9 [M+H]$^+$.

Example 5

4"-O-{3-[3-(3-Carboxy-1,4-dihydro-1-dimethylamino-4-oxo-6-quinolinyl)propylamino]propionyl}-erythromycin A (9E)-oxime

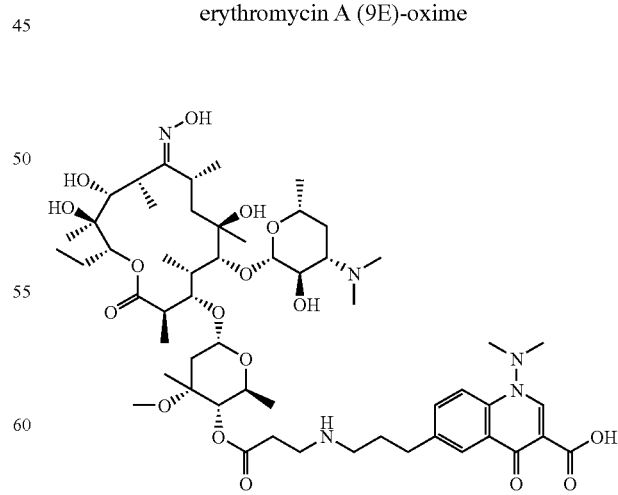

Using a similar procedure to that described in Example 1, Intermediate 1 (0.09 g) and Intermediate 4 (0.148 g) gave the title compound as a white solid; ESMS m/z 1092.8 [M+H]$^+$.

Example 6

4"-O-{3-[3-(3-Carboxy-1,4-dihydro-1-dimethylamino-4-oxo-6-quinolinyl)propylamino]propionyl}-erythromycin A (9E)-methoxime

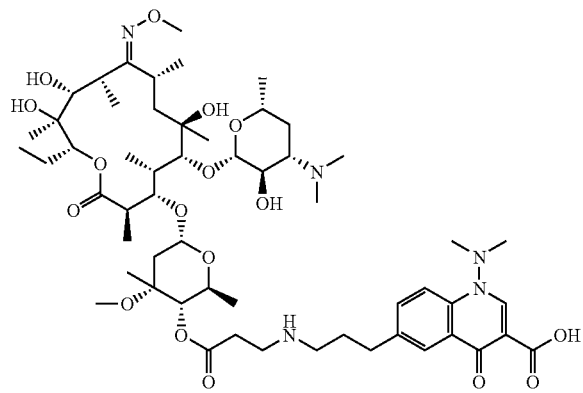

Using a similar procedure to that described in Example 1, Intermediate 1 (0.09 g) and Intermediate 5 (0.150 g) gave the title compound as a white solid; ESMS m/z 1106.9 [M+H]$^+$.

Example 7

4"-O-[3-[3-(3-Carboxy-1-dimethylamino-1,4-dihydro-4-oxo-6-quinolinyl) propylamino]propionyl]-6-O-methyl-erythromycin A (9E)-oxime

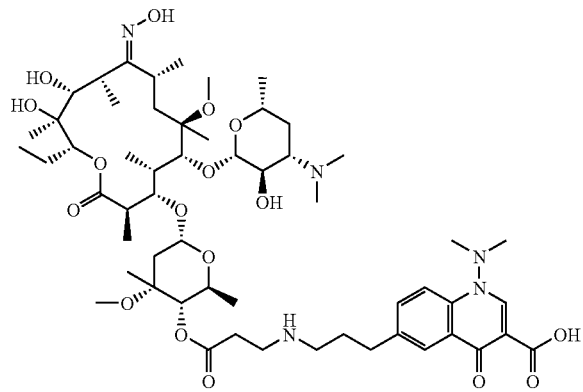

Using a similar procedure to that described in Example 1, Intermediate 1 (0.07 g) and Intermediate 6 (0.14 g) gave the title compound as a white solid; ESMS m/z 1108.0 [M+H]$^+$.

Example 8

4"-O-{3-[3-(3-Carboxy-1,4-dihydro-1-dimethylamino-4-oxo-6-quinolinyl)propylamino]propionyl}-6-O-methyl-erythromycin A lactobionate salt A solution of Example 1 (2.26 g) in methanol (20 mL) was treated with a solution of lactobionic acid (0.74 g) in water (200 mL) at ca. 20° C. The methanol was evaporated under reduced pressure and the aqueous lyophillized to give the title compound as a white freeze dried solid (2.7 g); ESMS m/z 1091.9 [M+H]$^+$, $\delta_H$ (400 MHz; CD$_3$OD) inter alia 4.44 (1H, d, J=7.6 Hz, lactobionate galactopyranosyl 1-H).

Example 9

4"-O-{3-[3-(3-Carboxy-1,4-dihydro-1-dimethylamino-4-oxo-6-quinolinyl)propylamino]propionyl}-6-O-methyl-erythromycin A citrate salt A solution of Example 1 (1.09 g) in methanol (10 mL) was treated with citric acid (192 mg). The solution was evaporated under reduced pressure to give the title compound (1.28 g). A portion (400 mg) of this solid was dissolved in warm 1-propanol (50 mL) and allowed to cool and crystallise to give the title compound as a white solid (0.210 g); ESMS m/z 1091.9 [M+H]$^+$.

Example 10

4"-O-{3-[2-(3-Carboxy-1,4-dihydro-1-dimethylamino-4-oxo-[1,7]naphthyridin-6-ylsulfanyl)-ethylamino]propionyl}-6-O-methyl-erythromycin A

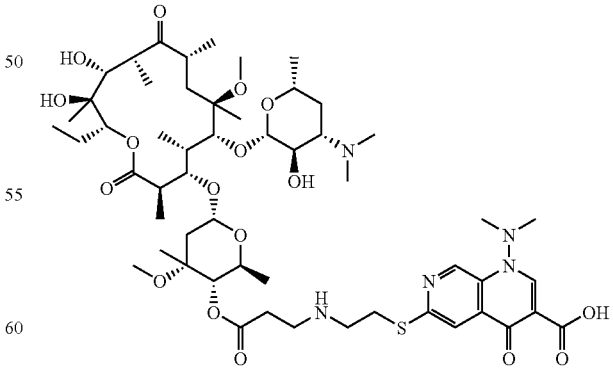

Using a similar procedure to that described in Example 1, Intermediate 8 (0.080 g) and Intermediate 11 (0.069 g) gave the title compound as a pale yellow solid (0.059 g); ESMS m/z 1111.0 [M+H]$^+$.

Example 11

4"-O-{3-[2-(3-Carboxy-1,4-dihydro-1-dimethylamino-4-oxo-7-quinolinyl)oxyethylamino]propionyl}-6-O-methyl-erythromycin A

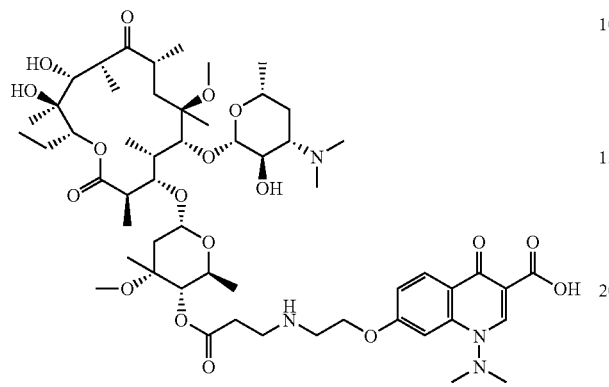

Using a similar procedure to that described in Example 1, Intermediate 8 (0.080 g) and Intermediate 12 (0.049 g) gave the title compound as a white solid (0.064 g); ESMS m/z 1094.0 [M+H]+.

Example 12

4"-O-{3-[2-(3-Carboxy-1,4-dihydro-1-dimethylamino-4-oxo-7-quinolinyl)oxyethylamino]propionyl}-azithromycin

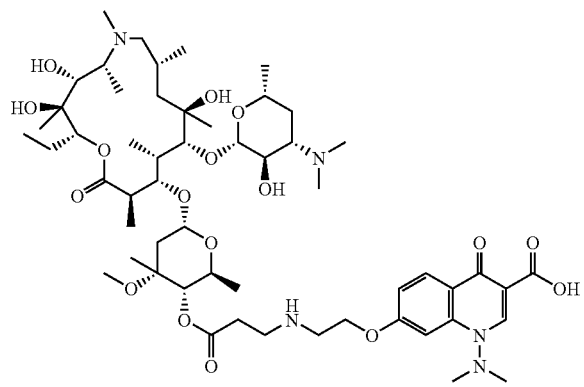

Using a similar procedure to that described in Example 1, Intermediate 13 (0.080 g) and Intermediate 12 (0.049 g) gave the title compound as a white solid (0.059 g); ESMS m/z 1095.1 [M+H]+.

Example 13

4"-O-{3-[2-(3-Carboxy-1,4-dihydro-1-dimethylamino-4-oxo-7-quinolinyl)oxyethylamino]propionyl}-erythromycin A (9E)-oxime

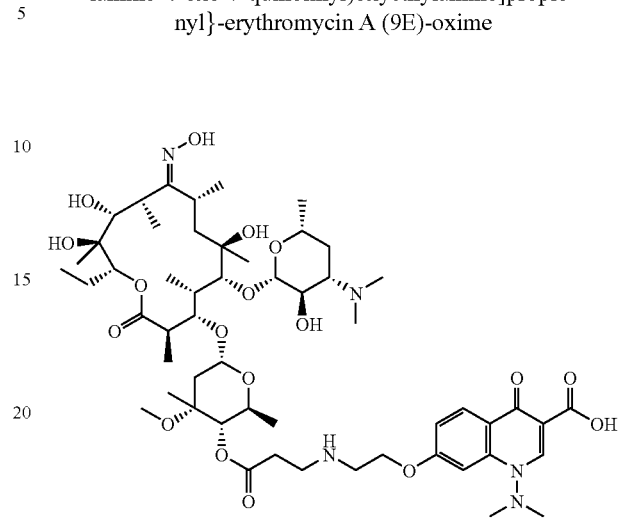

Using a similar procedure to that described in Example 1, Intermediate 4 (0.080 g) and Intermediate 12 (0.049 g) gave the title compound as a white solid, (0.042 g), ESMS m/z 1094.9 [M+H]+.

Example 14

4"-O-{3-[3-(3-Carboxy-1,4-dihydro-1-dimethylamino-4-oxo-6-quinolinyl)propylamino]propionyl}-azithromycin

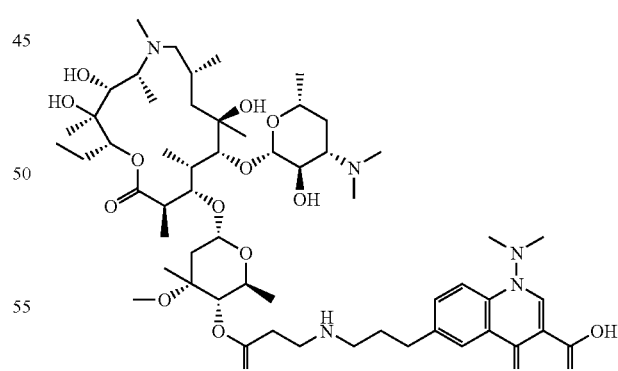

A mixture of Intermediate 13 (0.16 g) and Intermediate 1 (0.084 g) in dimethylsulfoxide (1.5 mL) and triethylamine (0.2 mL) was heated at 80° C. for 20 h. The mixture was concentrated and the residue chromatographed on silica gel eluting with 0-12% (9:1 methanol/20M aq. ammonia) in DCM to give the title compound as a white solid (0.123 g); ESMS m/z 1093.0 [M+H]+.

Example 15

4"-O-{3-[3-(6-Carboxy-2,3-dihydro-3-methyl-7-oxo-7H-[1,3,4]oxadiazino[6,5,4-ij]quinolin-9-yl)propylamino]propionyl}-6-O-methyl-erythromycin A

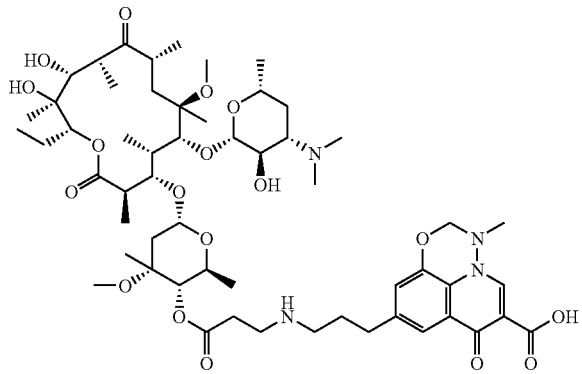

A mixture of Intermediate 8 (0.128 g) and Intermediate 14 (0.068 g) in dimethylsulfoxide (1.5 mL) and triethylamine (0.15 mL) was heated at 80° C. for 20 h. The mixture was concentrated and the residue chromatographed on silica gel eluting with 0-12% (9:1 methanol/20M aq. ammonia) in DCM to give the title compound as a white solid (0.070 g); ESMS m/z 1105.9 [M+H]$^+$.

Example 16

4"-O-{3-[3-(6-Carboxy-2,3-dihydro-3-methyl-7-oxo-7H-[1,3,4]oxadiazino[6,5,4-ij]quinolin-9-yl)propylamino]propionyl}-erythromycin A-(9E)-O-methoxymethyloxime

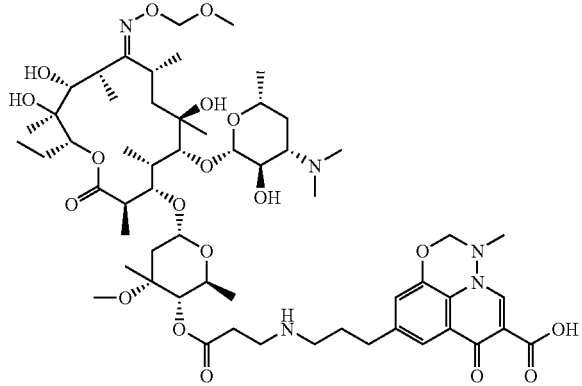

A mixture of Intermediate 21 (0.135 g) and Intermediate 14 (0.068 g) in dimethylsulfoxide (1.5 mL) and triethylamine (0.15 mL) was heated at 80° C. for 20 h. The mixture was concentrated and the residue chromatographed on silica gel eluting with 0-12% (9:1 methanol/20M aq. ammonia) in DCM to give the title compound as a white solid (0.078 g); ESMS m/z 1151.0 [M+H]$^+$.

Example 17

4"-O-{3-[[3-(3-Carboxy-1-dimethylamino-4-oxo-1,4-dihydro-quinolin-6-yl)-propyl]-methylamino]-propyl}-6-O-methyl-11-desoxy-11-(R)-amino-erythromycin A 11,12-carbamate

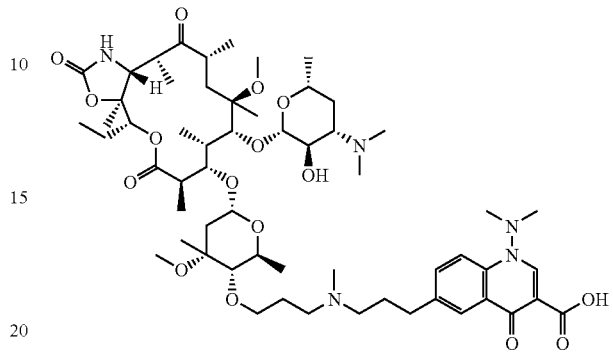

a) 2'-O-Acetyl-4"-O-allyloxycarbonyl-6-O-methyl-erythromycin A 11,12-carbonate 2'-O-Acetyl-6-O-methyl-erythromycin A (31.56 g) was dissolved in DCM (300 mL), cooled in an ice/salt bath, and pyridine (32 mL) added. To this solution was added a solution of triphosgene (10.69 g) in DCM (40 mL), keeping the temperature below −2° C. After stirring at −3° C. to 4° C. for 4.75 h, allyl alcohol (32 mL) was added dropwise. After 5 min at 0° C. the cooling bath was removed and stirring continued for 1 h. The mixture was then reduced in volume, diluted with EtOAc, washed with water (×2), saturated sodium hydrogen carbonate (×2), and brine (×2), dried (MgSO$_4$), and evaporated under reduced pressure. This residue was dissolved in warm EtOAc/DCM, reduced to a low volume (~45 mL), and the product allowed to crystallise. Diethyl ether was then added and the solid filtered off, washing with more diethyl ether. This solid was dried under reduced pressure to give the title compound as an off-white powder (28.5 g); ESMS m/z 900.5 [M+H]$^+$. Further product was obtained from the mother liquors, by chromatography.

b) 2'-O-Acetyl-4"-O-allyl-6-O-methyl-erythromycin A 11,12-carbonate

Example 17a (26.97 g) in THF (300 mL) was treated with tetrakis(triphenylphosphine)palladium (0.809 g) and triphenylphosphine (0.184 g) at reflux under argon. After 1.25 h, t-butyl allyl carbonate (F. Houlihan et al, Can. J. Chem. 1985, 63, 153; 12 mL) was added and the reflux continued for a further 3.5 h. The reaction was cooled and evaporated to dryness under reduced pressure to give a solid. This residue was triturated with diethyl ether to give the title compound as an off-white solid (17.67 g); ESMS m/z 856.7 [M+H]$^+$. Further product was obtained from the mother liquors, by chromatography.

c) 2'-O-Acetyl-4"-O-allyl-6-O-methyl-11-desoxy-11-(R)-amino-erythromycin A 11,12-carbamate Example 17b (25.65 g), carbonyldiimidazole (19.44 g) and imidazole (0.02 g) were dissolved in THF (230 mL) at 40° C., then DBU (4.93 mL) added. The mixture was stirred for 8 h at 63° C. and 10 h at 55° C. The mixture was allowed to cool over 5.5 h, then further cooled to −10° C. in an ice/salt bath before ammonia gas was added over 1 h and allowed to reflux using a low temperature condenser. After stirring for 1 h at −20° C., the condenser was removed and the reaction allowed to warm to 21° C. over 3 h. Argon was then bubbled through the mixture before the addition of potassium tert-butoxide (1 M in THF, 36 mL). After 3 h more potassium tert-butoxide (1 M in THF, 18 mL) was added. The mixture was then stirred for 16 h, reduced under reduced pressure to a small volume, diluted with water and the mixture extracted with EtOAc (×3). The combined organic extracts were washed with brine, dried, and evaporated under reduced pressure to give the crude solid product. This was triturated with diethyl ether to give the title compound as an off-white powder (8.43 g). A second batch of solid product was obtained, contaminated with imidazole. This was dissolved in EtOAc, washed with water, dried (MgSO$_4$) and evaporated under reduced pressure to give the title compound as an off-white powder (9.2 g); ESMS m/z 855.8 [M+H]$^+$. Further product was obtained from the mother liquors, by chromatography.

d) 2'-O-Acetyl-4"-O-(3-hydroxypropyl)-6-O-methyl-11-desoxy-11-(R)-amino-erythromycin A 11,12-carbamate Example 17c (20.54 g) in THF (150 mL) was treated with 9-borabicyclo[3.3.1]nonane (0.5 M in THF, 144 mL). After 1.25 h the solution was cooled to −14° C. in an ice/salt bath then pre-mixed and cooled hydrogen peroxide (30% aq, 1.7 mL) in sodium hydroxide (2 N, 2.5 mL) was added over 20 min (max. temp. −4° C.). After a further 5 min the reaction was diluted with brine and extracted with EtOAc (×3). The combined organic extracts were washed with brine (×3), dried (MgSO$_4$), and evaporated under reduced pressure to give the crude product. This was purified firstly by chromatography on silica gel (800 g), eluting with 0-6% methanolic ammonia [2M] in DCM, to give a white foam (contaminated with cyclooctanediol), then by chromatography, eluting with EtOAc followed by 4-8% methanolic ammonia [2M] in DCM, to give the title compound as a white powder (13.34 g); ESMS m/z 873.8 [M+H]$^+$.

e) 2'-O-Acetyl-4"-O-(3-oxopropyl)-6-O-methyl-11-desoxy-11-(R)-amino-erythromycin A 11,12-carbamate To Example 17d (2.15 g) in DCM (20 mL) was added Dess-Martin periodinane (3.44 g). Further portions of Dess-Martin periodinane (1.48 g, 0.16 g, 0.87 g and 0.71 g) were added after 50, 100, 130 and 250 min reaction time. After 360 min total reaction time, the reaction was diluted with DCM, washed with a mixture of aq sodium thiosulfate and aq sodium hydrogen carbonate, then brine, dried (MgSO$_4$) and evaporated under reduced pressure to give the crude title compound as a white foam (2.3 g), which was used without purification; ESMS m/z 871.8 [M+H]$^+$.

f) 2'-O-Acetyl-4"-O-{3-[3-(3-carboxy-1-dimethylamino-4-oxo-1,4-dihydro-quinolin-6-yl)-propylamino]-propyl}-6-O-methyl-11-desoxy-11-(R)-amino-erythromycin A 11,12-carbamate To Example 17e (1.27 g) in DCM (7 mL) was added 3 A molecular sieves (0.7 g), sodium acetate (0.275 g) and Intermediate 1 (0.57 g), followed by methanol (7 mL). Stirred for 5 min, then sodium cyanoborohydride (0.246 g) was added, followed by acetic acid (0.7 mL). Reaction mixture stirred for 30 min, then filtered and evaporated under reduced pressure, and again from toluene, to give a yellow gum. This residue was purified by chromatography on silica gel (100 g), eluting with 0-30% (20M aq. ammonia/methanol (1:9)) in DCM, to give impure title compound (0.776 g); ESMS m/z 1145.1 [M+H]$^+$.

g) 4"-O-{3-[[3-(3-Carboxy-1-dimethylamino-4-oxo-1,4-dihydro-quinolin-6-yl)-propyl]methylamino]-propyl}-6-O-methyl-11-desoxy-11-(R)-amino-erythromycin A 11,12-carbamate Example 17f (0.77 g) was dissolved in methanol and heated at 50° C. for 21 h and 60° C. for 0.5 h. evaporated under reduced pressure to dryness. This crude product was dissolved in chloroform (10 mL), then formic acid (0.192 mL) and formaldehyde (37% in water, 1.1 mL) added, and the mixture heated at 60° C. for 1 h. Evaporation under reduced pressure to dryness gave a yellow gum. This residue was purified by chromatography on silica gel (40 g), eluting with 0-35% (20M aq. ammonia/methanol (1:9)) in DCM, to give the title compound as an off white powder (0.49 g); ESMS m/z 1117.0 [M+H]$^+$.

Example 18

4"-O-(2-{(2-(3-Carboxy-1-dimethylamino-4-oxo-1,4-dihydro-[1,7]-naphthyridine-6-ylsulfanyl)-ethylamino}-ethyl)-6-O-methyl-erythromycin A 11,12-carbonate

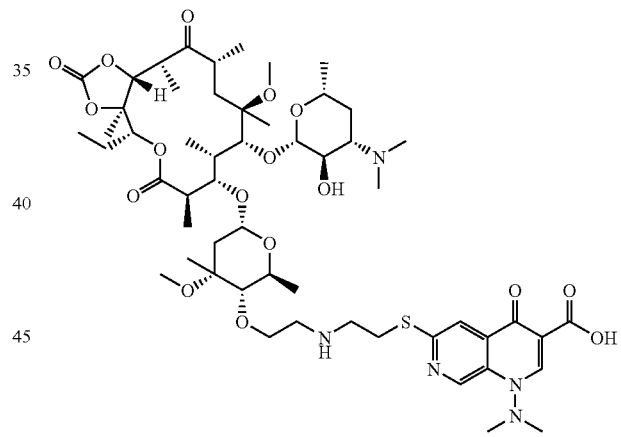

a) 2'-O-Acetyl-4"-O-(2-oxoethyl)-6-O-methyl-erythromycin A 11,12-carbonate

Example 17b (1.283 g) was dissolved in THF (10 mL) and water (2 mL), then osmium tetroxide (4% in water, 1 mL) added. After 5 min, N-methylmorpholine-N-oxide (50% in water, 0.53 mL) was added. Solution stirred for 2.75 h, then cooled in an ice bath and a solution of sodium metaperiodate (1.93 g) in water (20 mL) added slowly. Stirred, with cooling, for 0.25 h. Mixture filtered through Celite, washing well with EtOAc. Filtrate extracted with more EtOAc (×2). Combined organic extracts washed with dilute aqueous sodium thiosulfate (×2), water, and brine, dried (MgSO$_4$), and evaporated under reduced pressure to give the title compound as a pale brown foam (1.26 g); ESMS m/z 858.9 [M+H]$^+$ and 876.9 [M+H$_2$O+H]$^+$.

b) 2'-O-Acetyl-4"-O-(2-{2-(3-carboxy-1-dimethylamino-4-oxo-1,4-dihydro-[1,7]-naphthyridine-6-ylsulfanyl)-ethylamino}-ethyl)-6-O-methyl-erythromycin A 11,12-carbonate To Example 18a (0.429 g) in methanol (10 mL) was added 3 A molecular sieves (0.5 g), sodium acetate (0.123 g) and Intermediate 11 (0.258 g). Stirred for 5 min, then sodium cyanoborohydride (0.063 g) was added. Reaction mixture stirred for 1 h, then more methanol (10 mL), and acetic acid (0.5 mL) were added. Stirred for a further 17 h then filtered and evaporated under reduced pressure. The residue was purified by chromatography on silica gel (20 g), eluting with 0-24% (20M aq. ammonia/methanol (1:9)) in DCM, to give impure title compound as a pale yellow gum (0.046 g); ESMS m/z 1151.1 [M+H]$^+$ and 1109.1 [M−Ac$^-$+2H]$^+$.

c) 4"-O-(2-{2-(3-Carboxy-1-dimethylamino-4-oxo-1,4-dihydro-[1,7]-naphthyridine-6-ylsulfanyl)-ethylamino}-ethyl)-6-O-methyl-erythromycin A 11,12-carbonate Example 18b (0.046 g) in methanol (10 mL) was heated at 55° C. for 8 h and 50° C. for 15.5 h. The solution was then evaporated under reduced pressure to dryness and purified by mass directed automatic preparative HPLC to give the required product. This material was then freeze dried from dilute aqueous ammonia to give the title compound as a pale yellow powder (0.019 g); ESMS m/z 1109.0 [M+H]$^+$.

Example 19

4"-O-{3-[2-(3-Carboxy-1,4-dihydro-1-dimethylamino-4-oxo-6-quinolinyl)sulfanylethylamino]propionyl}-6-O-methyl-erythromycin A

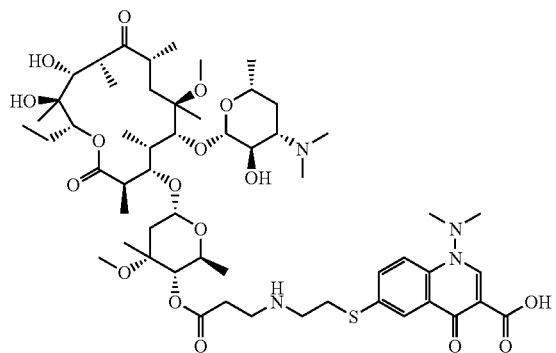

Using a similar procedure to that described in Example 1, Intermediate 8 (0.120 g), and Intermediate 15 (0.126 g) gave the title compound as a white solid (0.107 g); ESMS m/z 1110.0 [M+H]$^+$.

Example 20

4"-O-{3-[3-(3-Carboxy-1,4-dihydro-1-dimethylamino-4-oxo-6-quinolinyl)propylamino]propionyl}-erythromycin A-(9E)-oxime-11,12-carbonate

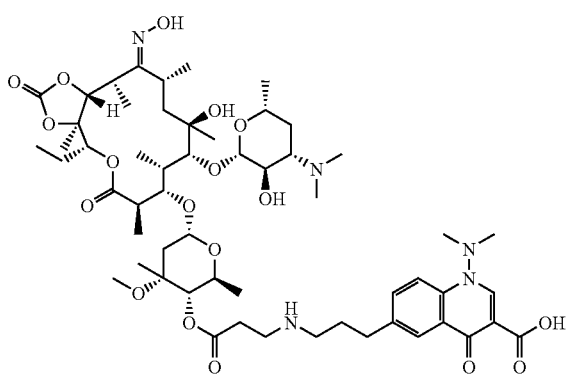

Using a similar procedure to that described in Example 1, Intermediate 16 (0.124 g) and Intermediate 1 (0.073 g) gave the title compound as a white solid (0.098 g); ESMS m/z 1119.1 [M+H]$^+$.

Example 21

4"-O-{3-[3-(3-Carboxy-1-dimethylamino-4-oxo-1,4-dihydro-quinolin-6-yl)-propoxy]-propyl}-6-O-methyl-erythromycin A

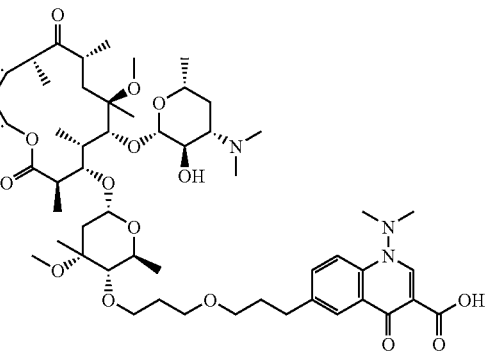

To Intermediate 18 (0.3 g) and Intermediate 17 (0.65 g) in THF (5 mL) under argon was added tetrakis(triphenylphosphine) palladium (0.020 g). The reaction was heated to reflux for 75 min after which time further tetrakis(triphenylphosphine) palladium (0.040 g) was added. After refluxing for a further 3.25 h Intermediate 17 (0.6 g) and tetrakis(triphenylphosphine) palladium (0.030 g) were added. After a further 2.5 h reflux, the reaction was cooled and evaporated under reduced pressure to dryness. The residue was taken up in acetonitrile (20 mL) and water (20 mL) containing formic acid (0.08 mL) and left for 20 h. Further formic acid (0.04 mL) was added. After a further hour, the reaction was evaporated under reduced pressure to dryness. The residue was purified by chromatography on silica gel eluting with 3-7.5% (2M methanolic ammonia) in DCM to yield impure 4"-O-{3-[3-(3-carboxy-1-dimethylamino-4-oxo-1,4-dihydro-quinolin-6-yl)-propoxy]-prop-2-en-1-yl}-6-O-methyl-erythromycin A ethyl ester as a gum (0.38 g); ESMS m/z 1105.0 [M+H]+. This material in ethanol was hydrogenated at room temperature and 1 atm over 10% Pd/C (0.1 g) for 3 h. The reaction was filtered, and the filtrate evaporated under reduced pressure to give impure 4"-O-{3-[3-(3-carboxy-1-dimethylamino-4-oxo-1,4-dihydro-quinolin-6-yl)-propoxy]-propyl}-6-O-methyl-erythromycin A ethyl ester (0.35 g) as a gum, ESMS m/z 1107.0 [M+H]+. This material (0.35 g), in 1,4-dioxan (20 mL) under argon was treated with water (5 mL) containing lithium hydroxide (0.044 g). After stirring for 90 min, the reaction mixture was evaporated under reduced pressure to low volume, and the residue taken up in water and solid $CO_2$ added. After evaporation under reduced pressure to dryness, the residue was purified by mass directed automatic preparative HPLC followed by chromatography on silica gel eluting with 0-15% (9:1 methanol/20M aq. ammonia) in DCM to give the title compound as a white solid foam (0.028 g); ESMS m/z 1079.1 [M+H]+.

Example 22

4"-O-{2-[(2-{[3-Carboxy-1-dimethylamino-4-oxo-1,4-dihydro-1,7-naphthyridin-6-yl]thio}ethyl)amino]ethyl}-6-O-methyl-erythromycin A

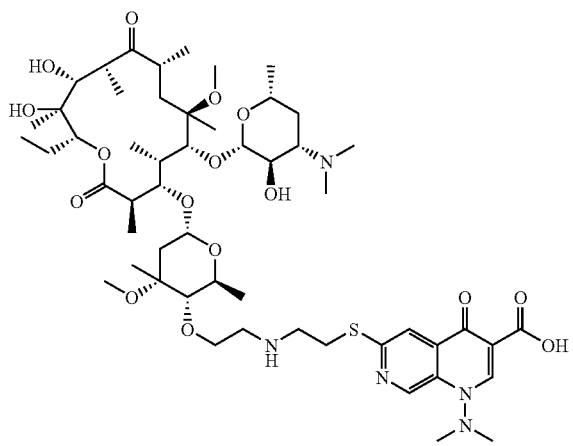

a) 9-Dihydro-9-methoxy-4"-O-2-oxoethyl-2',11-bis-O-trimethylsilyl-6-O-methyl-9,12-anhydro-erythromycin A To Intermediate 18d (2.0 g) in THF (3 mL) and water (1 mL) under argon was added osmium tetroxide (4% solution in water, 1 mL). After 5 min N-methyl morpholine N-oxide (0.36 g) was added. After stirring for 1 h the reaction was diluted with THF (18 mL) and water (30 mL) and cooled to 0° C. Sodium periodate (2.9 g) in water (30 mL) was added. After stirring for 10 m, the reaction mixture was filtered and the solid washed with EtOAc (50 mL) The filtrates were combined and the phases separated. The organic layer was washed with sat. aq. sodium thiosulfate (2×25 mL). After drying with magnesium sulfate, the solution was evaporated under reduced pressure to give a grey foam. This material was dissolved in THF (20 mL) and water (30 mL), and cooled to 0° C. Sodium periodate (1.5 g) in water (15 mL) was added. After stirring for 15 min, the reaction mixture was filtered and the solid washed with EtOAc (50 mL) The filtrates were combined and the phases separated. The organic layer was washed with sat. aq. sodium thiosulfate (2×25 mL). After drying with magnesium sulfate, the solution was evaporated under reduced pressure to give the title compound as a grey foam (1.6 g); ESMS m/z 966.8 [M+$H_2$O+H]+.

b) 4"-O-{2-[(2-{[3-Carboxy-1-dimethylamino-4-oxo-1,4-dihydro-1,7-naphthyridin-6-yl]thio}ethyl)amino]ethyl}-6-O-methyl-erythromycin A To Example 22a (0.3 g) in methanol (3 mL) was added Intermediate 11 (0.138 g) in methanol (5 mL), acetic acid (0.1 mL), and a solution of sodium cyanoborohydride (0.032 g) in methanol (0.5 mL). The reaction was stirred for 3 h then evaporated under reduced pressure. The residue was dissolved in acetonitrile (25 mL), and treated with 1.2% aq. formic acid (25 mL) for 20 h at 4° C. before evaporating under reduced pressure to dryness. The crude product was purified by mass directed automatic preparative HPLC) followed by chromatography on silica gel eluting with 5-15% (9:1 methanol/20M aq. ammonia) in DCM to give the title compound as a white solid foam (0.016 g); ESMS m/z 1082.9 [M+H]+.

Example 23

4"-O-{2-[(2-{[3-Carboxy-1-dimethylamino-4-oxo-1,4-dihydro-7-quinolinyl]oxy}ethyl)amino]ethyl}-6-O-methyl-erythromycin A

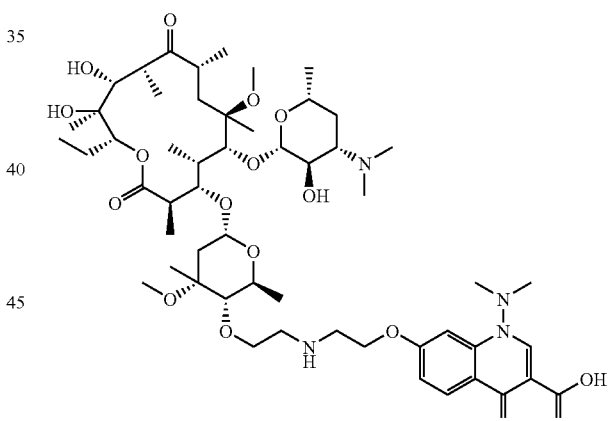

To Example 22a (0.35 g) in methanol (3 mL) was added Intermediate 12 (0.164 g) in methanol (5 mL) and dimethylformamide (5 mL), acetic acid (0.1 mL), 3 A molecular sieves (0.5 g) sodium acetate (0.1 g) and a solution of sodium cyanoborohydride (0.037 g) in methanol (0.5 mL). The reaction was stirred for 1 h then filtered. The solid was washed with methanol and the combined filtrates evaporated under reduced pressure. The residue was dissolved in acetonitrile (25 mL), and treated with 0.6% aq. formic acid (25 mL) for 20 h at 4° C. before evaporating under reduced pressure to dryness. The crude product was purified by mass directed automatic preparative HPLC followed by chromatography on silica gel eluting with 5-15% (9:1 methanol/20M aq. ammonia) in DCM to give the title compound as an off-white solid foam (0.040 g); ESMS m/z 1066.0 [M+H]+.

Example 24

4"-O-{3-[2-{[6-Carboxy-8-dimethylamino-5-oxo-5,8-dihydro-18-naphthyridin-3-yl]thio}ethylamino]propionyl}-6-O-methyl-erythromycin A

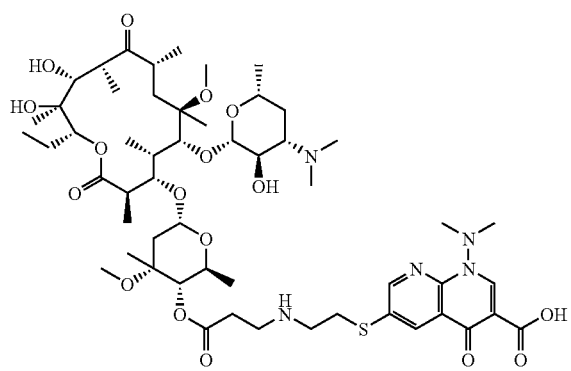

A mixture of Intermediate 8 (0.12 g) and Intermediate 19 (0.126 g) in DMSO (1 mL), water (1 drop) and triethylamine (0.084 mL) was heated at 80° C. for 24 h, 90° C. for 72 h and 100° C. for 24 h. The crude product was purified by mass directed automatic preparative HPLC followed by chromatography on silica gel eluting with 0-20% (9:1 methanol/20M aq. ammonia) in DCM to give the title compound as an off-white solid foam (0.061 g); ESMS m/z 1110.9 [M+H]$^+$.

Example 25

4"-O-{3-[3-[6-Carboxy-8-dimethylamino-5-oxo-5,8-dihydro-1,8-naphthyridin-3-yl])propylamino]propionyl}-6-O-methyl-erythromycin A

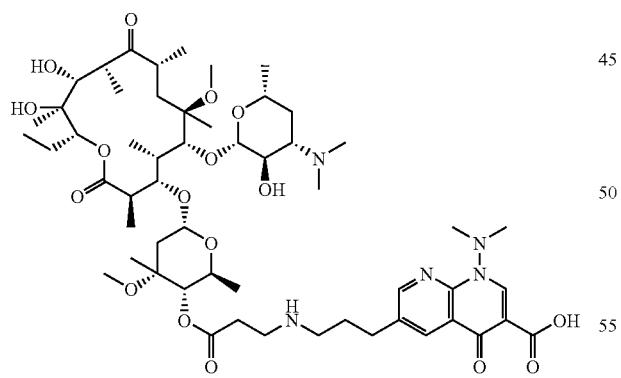

A mixture of Intermediate 8 (0.12 g) and Intermediate 20 (0.126 g) in DMSO (1 mL), water (1 drop) and triethylamine (0.084 mL) was heated at 80° C. for 16 h. The crude product was purified by mass directed automatic preparative HPLC followed by chromatography on silica gel eluting with 0-20% (9:1 methanol/20M aq. ammonia) in DCM to give the title compound as an off-white foam (0.037 g); ESMS m/z 1093.0 [M+H]$^+$.

Example 26

4"-O-[3-[3-(3-Carboxy-1-dimethylamino-1,4-dihydro-4-oxo-6-quinolinyl) propylamino]propionyl] erythromycin A-(9E)-O-methoxymethyloxime

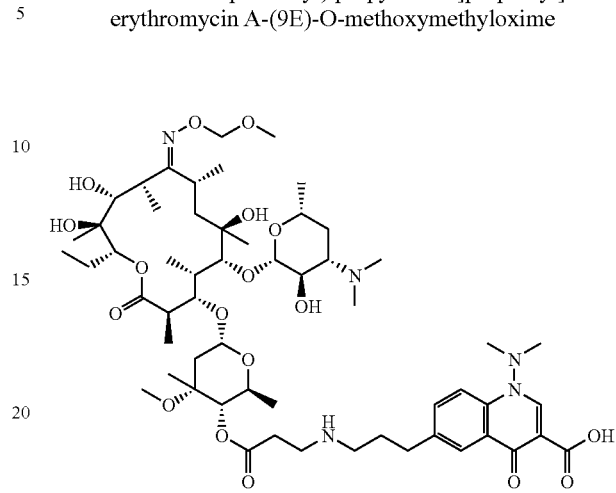

Using a similar procedure to that described in Example 1, Intermediate 1 (0.038 g) and Intermediate 21 (0.070 g) gave the title compound as a white solid; ESMS m/z 1137.0 [M+H]$^+$.

Example 27

4"-O-{2-[3-(3-Carboxy-1,4-dihydro-1-dimethylamino-4-oxo-6-quinolinyl)propylamino]ethyl}-6-O-methyl-erythromycin A

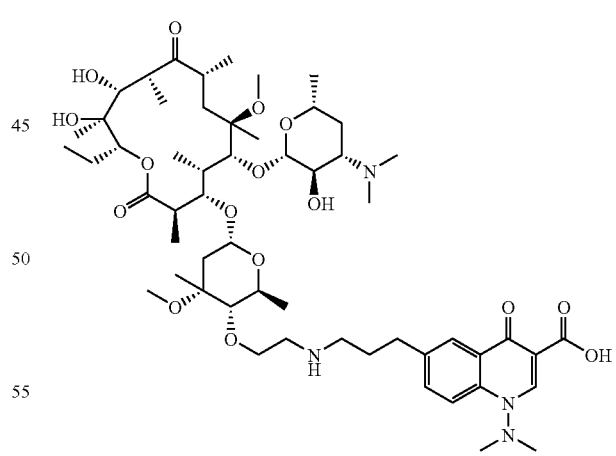

Intermediate 23 (0.64 g), Intermediate 1 (0.388 g), sodium acetate (0.082 g) and acetic acid (0.06 mL) in methanol (15 mL) were treated with a solution of sodium cyanoborohydride (0.093 g) in methanol (2 mL). After 1.5 h the reaction was evaporated under reduced pressure and purified by chromatography on silica gel eluting with 3-15% (9:1 methanol/20M aq. ammonia) in DCM to give the title compound as a yellow solid foam (0.07 g); ESMS m/z 1064.1 [M+H]$^+$.

Example 28

4"-O-{3-[3-(3-Carboxy-1,4-dihydro-1-dimethylamino-4-oxo-7-quinolinyloxy)propylamino]propionyl}-6-O-methyl-erythromycin A

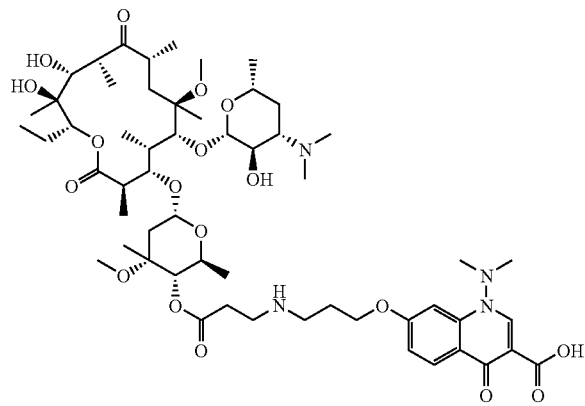

A mixture of Intermediate 8 (0.08 g) and Intermediate 25 (0.055 g) in DMSO (0.5 mL), water (1 drop) and triethylamine (0.04 mL) was heated at 80° C. for 35 h. The mixture was diluted with DCM, washed with saturated aqueous sodium hydrogen carbonate and water, dried (Na$_2$SO$_4$), concentrated and the residue flash chromatographed on silica gel eluting with 10-18% (9:1 MeOH/0.880 NH$_3$) in DCM to give the title compound as a white solid (0.055 g); ESMS m/z 1108.1 [M+H]$^+$.

Example 29

4"-O-{2-[(2-{[3-Carboxy-1-dimethylamino-4-oxo-1,4-dihydro-7-quinolinyl]oxy}ethyl)methylamino]ethyl}-6-O-methyl-erythromycin A

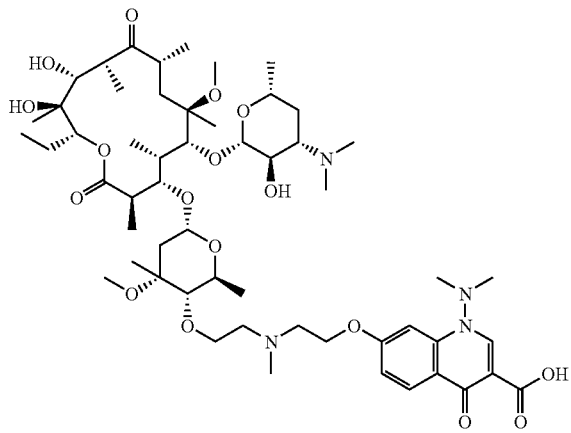

Example 23 (0.033 g) was dissolved in chloroform (2.5 mL), then formic acid (0.008 mL) and formaldehyde (37% in water, 0.008 mL) added, and the mixture heated at reflux for 15 min. The reaction was evaporated under reduced pressure to dryness, taken up in acetonitrile (5 mL) and water (5 mL) and evaporated under reduced pressure to dryness. This residue was purified by mass directed automatic preparative HPLC followed by freeze drying from dilute aqueous ammonia to give the title compound as a white solid (0.008 g); ESMS m/z 1079.9 [M+H]$^+$.

Example 30

4"-O-{2-[(3-[3-Carboxy-1-dimethylamino-4-oxo-1,4-dihydro-6-quinolinyl]propyl)methylamino]ethyl}-6-O-methyl-erythromycin A; and D-tartrate, phosphate and fumarate salts

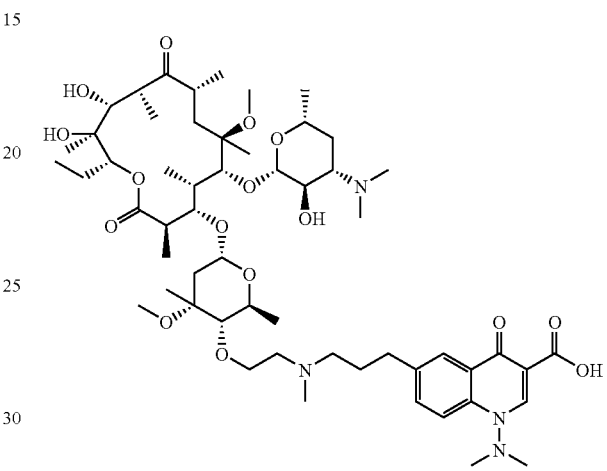

a) 4"-O-{2-[(3-[3-Carboxy-1-(dimethylamino)-4-oxo-1,4-dihydro-6-quinolinyl]propyl)methylamino]ethyl}-6-O-methyl-erythromycin A ethyl ester Intermediate 23 (91.5 g) in DCM (1 L) was stirred under argon with Intermediate 24 (33.6 g), and 3 A molecular sieves (45 g) for 30 min, then sodium triacetoxy borohydride (45.1 g) was added. After 40 min the solution was decanted from the molecular sieves, which were extracted with more DCM. The combined DCM solutions were washed with water (2×250 mL) and 5% potassium carbonate (250 mL), the combined aqueous extracted with DCM (50 mL) and the combined DCM solutions dried (Na$_2$SO$_4$) and evaporated under reduced pressure to a yellow solid foam (156.4 g). This was purified using 3 Biotage 75 800 g columns eluting with 0-6.5% (10:1 MeOH/0.880 NH$_3$) in DCM to give the title compound (65.1 g); ES m/z 1106.0 [M+H]$^+$.

b) 4"-O-{2-[(3-[3-Carboxy-1-dimethylamino-4-oxo-1,4-dihydro-6-quinolinyl]propyl)methylamino]ethyl}-6-O-methyl-erythromycin A D-tartrate salt Example 30a (65.1 g) in THF (550 mL) was treated with 0.5M LiOH (283 mL) at room temperature under argon. After 2.5 h 1M sodium dihydrogen phosphate was added to give a pH of approximately 11, and the mixture extracted with diethyl ether (500 mL). On standing a white crystalline solid separated from the organic layer, collection by filtration, washing with ether and drying gave 1.3 g, ES m/z 1078.0 [M+H]$^+$.

The aqueous layer was treated with a small amount of phosphoric acid, giving a pH 10.4 when a solid rapidly separated. This was collected by filtration to give 125 g of wet solid. A portion of this (109 g) was slurried in water and DCM (400 mL) and the pH adjusted to 7.2 with 1M sodium dihydrogen phosphate. The aqueous was extracted with a further 400 mL DCM, the combined extracts were dried ($Na_2SO_4$) and evaporated under reduced pressure to give a pale foam (47.8 g). This material was dissolved in acetone (3.5 L) at 42° C. and treated with D-tartaric acid (6.66 g in 240 mL water) and seeded with authentic material. After stirring at 20° C. for 4 h with final ice bath cooling, the solid was filtered off, washed with acetone and dried under reduced pressure to give the title compound as a white powder (43.6 g); ES m/z 1077.9 $[M+H]^+$, $\delta_H$ (400 MHz; $CD_3OD+CDCl_3$) inter alia 4.37 (2H, s, tartrate H-2 and -3).

c) 4"-O-{2-[(3-[3-Carboxy-1-(dimethylamino)-4-oxo-1,4-dihydro-6-quinolinyl]propyl)methylamino]ethyl}-6-O-methyl-erythromycin A Example 30b (20 g) was converted to free base by stirring with 0.1 M aqueous sodium hydrogen carbonate solution. The solution was extracted with DCM, dried ($Na_2SO_4$) and evaporated under reduced pressure to a solid white foam. This material was treated with water, the mixture sonicated and partially evaporated at reduced pressures down to 60 mbar to give a fine solid slurry. The solid was collected by filtration and dried under vacuum at 35° C. over phosphorus pentoxide to give the title compound as a white powder (16.27 g); ES m/z 1077.6 $[M+H]^+$.

d): 4"-O-{2-[(3-[3-Carboxy-1-dimethylamino-4-oxo-1,4-dihydro-6-quinolinyl]propyl)methylamino]ethyl}-6-O-methyl-erythromycin A phosphate salt Example 30c (9.1 g) in acetonitrile (450 mL) was treated with a solution of phosphoric acid (1.656 g) in water (40 mL) and acetonitrile (90 mL). The hazy solution was filtered through kieselguhr and allowed to crystallize overnight at 20° C. and 3 h at 4° C. The white solid was filtered off, washed with acetonitrile and dried to give the title compound, 8.238 g. ES m/z 1077.9 $[M+H]^+$.

e): 4"-O-{2-[(3-[3-Carboxy-1-dimethylamino-4-oxo-1,4-dihydro-6-quinolinyl]propyl)methylamino]ethyl}-6-O-methyl-erythromycin A fumarate salt To Example 30c (231.7 mg) was added isopropanol (2 mL). The solution was stirred for 15 minutes and then fumaric acid (52.42 mg, 2.1 equiv.) was added to the solution. The slurry was heated to 50° C. and left stirring overnight. The next day the slurry was filtered, washed with isopropanol and dried in a vacuum oven at 50° C. with a slow flow of nitrogen to yield the title compound as a white solid (112.2 mg). $\delta_H$ (DMSO-d6) inter alia 6.55 (s, fumarate H-2 and -3).

Example 31

4"-O-{2-[(3-[3-Carboxy-1-(morpholin-4-yl)-4-oxo-1,4-dihydro-6-quinolinyl]propyl)amino]ethyl}-6-O-methyl-erythromycin A

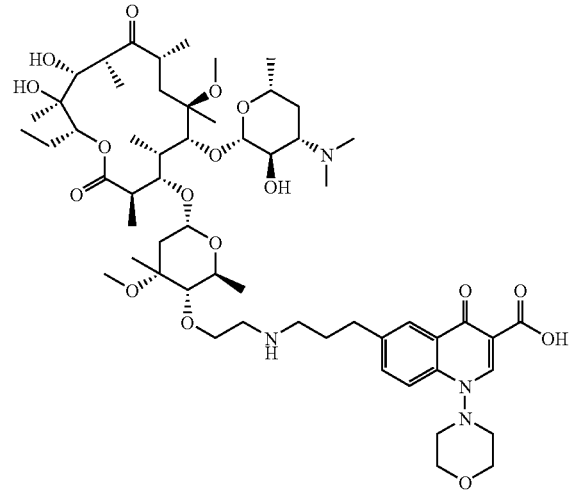

Intermediate 23 (0.292 g), Intermediate 2 (0.164 g), sodium acetate (0.051 g), 3 A molecular sieves (0.15 g) and acetic acid (0.15 mL) in methanol (15 mL) were treated with sodium cyanoborohydride (0.026 g). The reaction was stirred at 20° C. for 2 h and at 0° C. overnight. The reaction mixture was diluted with DCM and filtered through celite. The filtrate was evaporated under reduced pressure to dryness. The residue was purified by chromatography on silica gel eluting with 12-20% (9:1 methanol/20M aq. ammonia) in DCM and the product containing fractions repurified by mass directed automatic preparative HPLC followed by freeze drying from dilute aqueous ammonia to give the title compound as a white solid (0.015 g); ESMS m/z 1105.9 $[M+H]^+$.

Example 32

4"-O-{2-[(3-[3-carboxy-1-methylamino-4-oxo-1,4-dihydro-6-quinolinyl]propyl)amino]ethyl}-6-O-methyl-erythromycin A

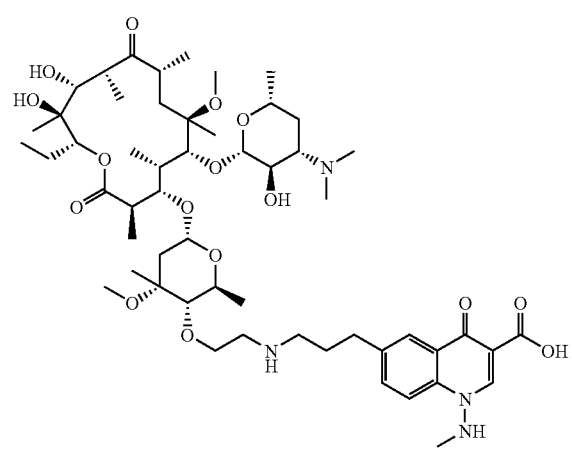

Intermediate 23 (0.40 g), Intermediate 3 (0.236 g), sodium acetate (0.117 g), 3 A molecular sieves (0.30 g) and acetic acid (0.3 mL) in methanol (10 mL) were treated with sodium cyanoborohydride (0.060 g). The reaction was stirred at 20° C. for 2 h and at 0° C. overnight. The reaction mixture was diluted with DCM and filtered through celite. The filtrate was evaporated under reduced pressure to dryness. The residue was purified by chromatography on silica gel eluting with 14-22% (9:1 methanol/20M aq. ammonia) in DCM and the product containing fractions repurified by mass directed automatic preparative HPLC followed by freeze drying from dilute aqueous ammonia to give the title compound as a white solid (0.011 g); ESMS m/z 1049.7 [M+H]+.

Example 33

4"-O-{2-[(3-[3-Carboxy-1-dimethylamino-4-oxo-1,4-dihydro-6-quinolinyl]propyl)methylamino]ethyl}-erythromycin A-(9E)-(cyanomethyl)oxime

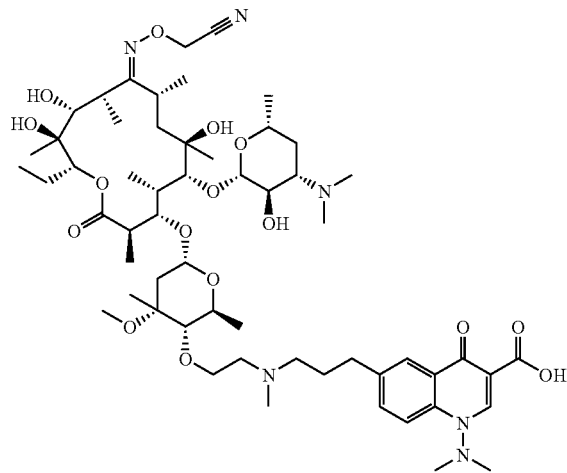

a) 4"-O-{2-[(3-[3-Carboxy-1-dimethylamino-4-oxo-1,4-dihydro-6-quinolinyl]propyl)methylamino]ethyl}-erythromycin A-(9E)-(cyanomethyl)oxime ethyl ester Intermediate 38 (0.75 g) in DCM (20 mL) and methanol (2 mL) was cooled to −78° C. under argon and TFA (0.14 mL) added. Ozonised oxygen was bubbled in until a blue colour developed. Argon was bubbled through the mixture to flush out the ozone, then dimethyl sulfide (0.27 mL) and triethylamine (0.38 mL) were added. The reaction was allowed to warm to 20° C. and stirred for 30 min.

The reaction mixture was washed with water, dried (Na2SO4) and evaporated under reduced pressure to dryness. The crude erythromycin-4"-O-(2-oxoethyl)-(9E)-(cyanomethyl)oxime (0.81 g) was used without purification.

A portion of this material (0.27 g), Intermediate 24 (0.12 g), and 3 A molecular sieves (0.15 g) in DCM (10 mL) were stirred for 15 min. Sodium triacetoxy borohydride (0.128 g) was added followed after 5 min by acetic acid (2 drops). After 45 min the solution was decanted from the molecular sieves, which were extracted with more DCM. The combined DCM solutions were evaporated under reduced pressure. Chromatography on silica eluting with 2-8% (9:1 MeOH/0.880 ammonia) in DCM gave the title compound as a yellow foam (0.28 g); ES m/z 1146.0 [M+H]+.

b) 4"-O-{2-[(3-[3-Carboxy-1-dimethylamino-4-oxo-1,4-dihydro-6-quinolinyl]propyl)methylamino]ethyl}-erythromycin A-(9E)-(cyanomethyl)oxime Example 33a (0.28 g) in THF (10 mL) was treated with 0.5M LiOH (0.95 mL) at room temperature under argon. After 4 h 1M formic acid (0.03 mL) was added and the mixture evaporated under reduced pressure. Chromatography on silica eluting with 6-14% (9:1 MeOH/0.880 ammonia) in DCM gave the title compound as a white foam (0.084 g); ES m/z 1117.8 [M+H]+.

Example 34

4"-O-{3-[(3-[3-Carboxy-1-dimethylamino-4-oxo-1,4-dihydro-6-quinolinyl]propyl)methylamino]propyl}-6-O-methyl-erythromycin A

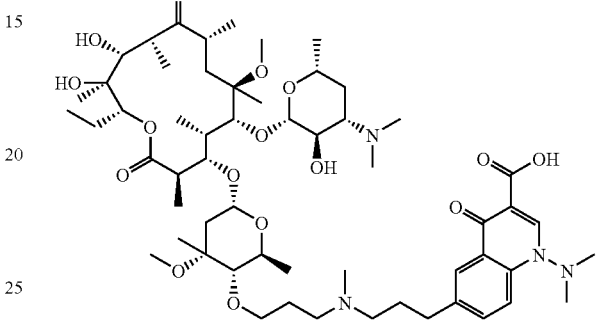

a) 4"-O-(3-Hydroxypropyl)-6-O-methyl-erythromycin A

Intermediate 22 (2.361 g) was dissolved in THF (15 mL), then 9-BBN (0.5M in THF, 12 mL) added. More 9-BBN (16 mL) was added portionwise over 2.5 h. The mixture was stirred for a total of 4 h. Cooled to −4° C. then a pre-cooled mixture of hydrogen peroxide (27% in water, 6 mL) and sodium hydroxide (2N, 4.5 mL) added slowly, maintaining temperature below 5° C. The reaction mixture was then diluted with brine and extracted with EtOAc (×3). The combined organic extracts were washed with brine (×3), dried and evaporated under reduced pressure to give a gummy white foam. Chromatography on silica gel (100 g) eluting with EtOAc then 2-8% (9:1 MeOH/0.880 ammonia) in DCM gave the title compound as a white foam (1.738 g); ESMS m/z 806.6 [M+H]+.

b) 4"-O-{3-[(3-[3-Carboxy-1-dimethylamino-4-oxo-1,4-dihydro-6-quinolinyl]propyl)amino]propyl}-6-O-methyl-erythromycin A ethyl ester To Example 34a (0.403 g) in DCM (20 mL) was added Dess-Martin periodinane (0.424 g). The mixture was stirred for 1 h, then diluted with DCM, washed with aqueous sodium thiosulphate/sodium hydrogen carbonate solution (×2), and brine, dried (Na2SO4) and evaporated under reduced pressure to give crude 4"-O-(3-oxopropyl)-6-O-methyl-erythromycin A (0.56 g), which was used without purification.

This material (0.56 g) in DCM (10 mL) was stirred under argon with Intermediate 24 (0.199 g) and 3 A molecular sieves (0.25 g) for 1 min, then sodium triacetoxy borohydride (0.213 g) was added. After 20 min the solution was filtered and evaporated under reduced pressure. The residue was purified by chromatography on silica gel (40 g) eluting with 2-7.5% (9:1MeOH/0.880 ammonia) in DCM to give the title compound as a white foam (0.418 g); ESMS m/z 1119.9 [M+H]+.

c) 4"-O-{3-[(3-[3-Carboxy-1-dimethylamino-4-oxo-1,4-dihydro-6-quinolinyl]propyl)methylamino]propyl}-6-O-methyl-erythromycin A Example 34b (0.412 g) in THF (5 mL) was treated with 0.5M LiOH (1.48 mL) at room temperature under argon. After 2.5 h glacial acetic acid (8 drops) was added and the solution evaporated under reduced pressure to dryness. The residue was purified by chromatography on silica gel (20 g) eluting with 3-9% (9:1 MeOH/0.880 ammonia) in DCM to give the title compound as a white foam (0.305 g); ESMS m/z 1089.8 [M−H]⁻.

Example 35

4"-O-{2-[3-(3-Carboxy-1-dimethylamino-4-oxo-1,4-dihydro-quinolin-6-yl)-propyloxy]-ethylcarbamoyl}-(9E)-O-methyloxime-erythromycin A

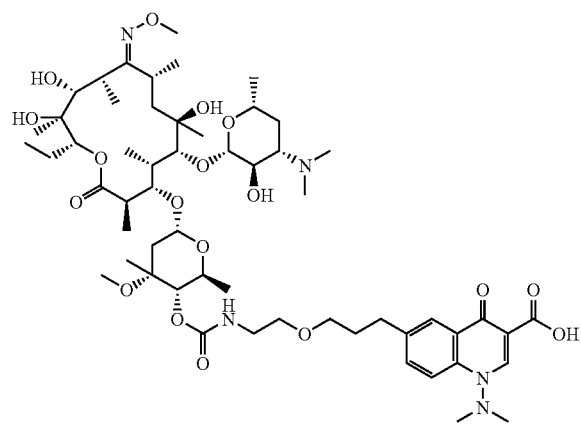

a) 2'-O-Acetyl-4"-O-{2-[3-(3-carboxy-1-dimethylamino-4-oxo-1,4-dihydro-quinolin-6-yl)-propyloxy]-ethylcarbamoyl}-(9E)-O-methyloxime-erythromycin A Intermediate 28 (0.20 g) was dissolved in dry DMF (2 mL) under nitrogen. To this solution a solution of Intermediate 26 (0.10 g) and DBU (0.10 mL) in dry DMF (2.5 mL) was added dropwise at room temperature. The resulting mixture was stirred at room temperature for 72 h. Solvent was removed under reduced pressure and the residue was dissolved in MeOH and purified using a cartridge (10 g C18 silica gel, eluent 150 mL water/acetonitrile 95/5 with 0.5% formic acid; then 100 mL water/acetonitrile 5/95 with 0.5% formic acid); the acetonitrile fraction was evaporated under reduced pressure and the resulting residue was purified by flash chromatography (silica gel, eluent 0-10% of 9/1 methanol/20M ammonia in DCM) to give the title compound as white foam (0.115 g); ESMS m/z 1164.8 [M+H]⁺.

b) 4"-O-{2-[3-(3-Carboxy-1-dimethylamino-4-oxo-1,4-dihydro-quinolin-6-yl)-propyloxy]-ethylcarbamoyl}-(9E)-O-methyloxime-erythromycin A A solution of Example 35a (0.113 g) in MeOH (5 mL) was stirred at 50° C. overnight. The solvent was removed under reduced pressure and the residue was purified by flash chromatography (silica gel, eluent 0-10% of 9/1 methanol/20M ammonia in DCM) to give the title compound as a pale yellow powder (0.082 g); ESMS m/z 1122.7 [M+H]⁺.

Example 36

4"-O-{2-[3-(3-Carboxy-1-dimethylamino-4-oxo-1,4-dihydro-quinolin-6-yl)-propyloxy]-ethylcarbamoyl}-(9E)-O-methoxymethyloxime-erythromycin A

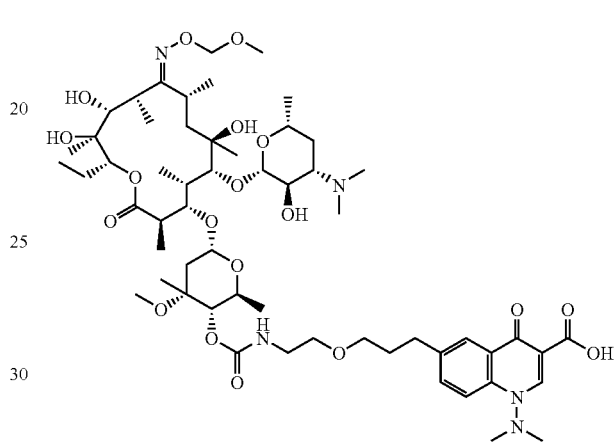

a) 2'-O-Acetyl-4"-O-{2-[3-(3-carboxy-1-dimethylamino-4-oxo-1,4-dihydro-quinolin-6-yl)-propyloxy]-ethylcarbamoyl}-(9E)-O-methoxymethyloxime-erythromycin A To a solution of Intermediate 29 (0.193 g) in dry DMF (3 mL) a solution of Intermediate 26 (0.093 g) and DBU (0.09 mL) in dry DMF (2.5 mL) was added dropwise at room temperature. The resulting mixture was stirred at room temperature for 72 h. Solvent was removed under reduced pressure and the residue was dissolved in MeOH and purified using a cartridge (10 g C18 silica gel, eluent 150 mL water/acetonitrile 95/5 with 0.5% formic acid; then 100 mL water/acetonitrile 5/95 with 0.5% formic acid); the acetonitrile fraction was evaporated under reduced pressure and the resulting residue was purified by flash chromatography (silica gel, eluent 0-10% of 9/1 methanol/20M ammonia in DCM) to give the title compound as white foam (0.119 g); ESMS m/z 1194.7 [M+H]⁺.

b) 4"-O-{2-[3-(3-carboxy-1-dimethylamino-4-oxo-1,4-dihydro-quinolin-6-yl)-propyloxy]-ethylcarbamoyl}-(9E)-O-methoxymethyloxime-erythromycin A A solution of Example 36a (0.118 g) in MeOH (5 mL) was stirred at 50° C. overnight. The solvent was removed under reduced pressure to give the title compound as a pale yellow powder (0.109 g); ESMS m/z 1152.7 [M+H]⁺.

Example 37

4"-O-{2-[3-(3-carboxy-1-dimethylamino-4-oxo-1,4-dihydro-quinolin-6-yl)-propyloxy]-ethylcarbamoyl}-6-O-methyl-erythromycin A

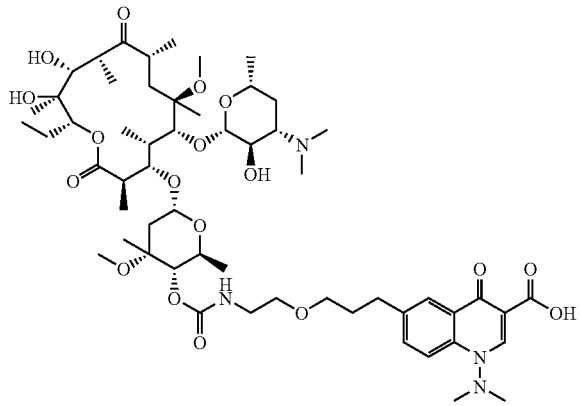

To a solution of Intermediate 18a (0.250 g) in dry DMF (5 mL) a solution of Intermediate 26 (0.159 g) and DBU (0.18 mL) in dry DMF (5 mL) was added dropwise at room temperature. The resulting mixture was stirred at room temperature for 72 h. Solvent was removed under reduced pressure and the residue was dissolved in MeOH and purified using a cartridge (10 g C18 silica gel, eluent 150 mL water/acetonitrile 95/5 with 0.5% formic acid; then 100 mL water/acetonitrile 5/95 with 0.5% formic acid); the acetonitrile fraction was evaporated under reduced pressure and the resulting residue was purified by flash chromatography (silica gel, eluent 0-10% of 9/1 methanol/20M ammonia in DCM) to give the title compound as white foam (0.210 g); ESMS m/z 1107.8 [M+H]$^+$.

Example 38

4"-O-{2-[3-(3-Carboxy-1-dimethylamino-4-oxo-1,4-dihydro-quinolin-6-yl)-propyloxy]-ethylcarbamoyl}-(9S)-9-O,11-O-ethylidene-9-dihydro-erythromycin A

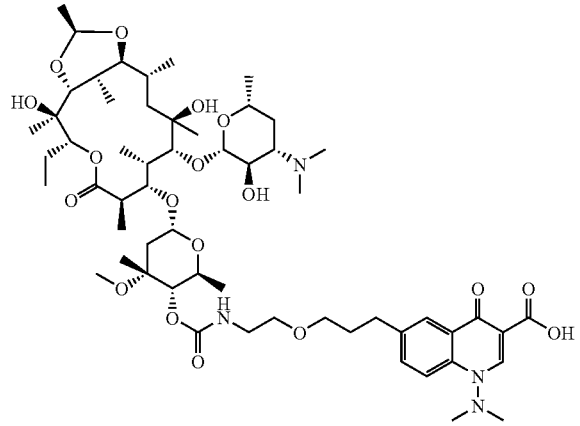

a) 2'-O-Acetyl-4"-O-{2-[3-(3-carboxy-1-dimethylamino-4-oxo-1,4-dihydro-quinolin-6-yl)-propyloxy]-ethylcarbamoyl}-(9S)-9-O,11-O-ethylidene-9-dihydro-erythromycin A Intermediate 30 (0.224 g) was dissolved in dry DMF (4 mL) under nitrogen. To this solution a solution of Intermediate 26 (0.140 g) and DBU (0.15 mL) in dry DMF (4 mL) was added dropwise at room temperature. The resulting mixture was stirred at room temperature for 72 h. Solvent was removed under reduced pressure and the residue was dissolved in MeOH and purified using a cartridge (10 g C18 silica gel, eluent 150 mL water/acetonitrile 95/5 with 0.5% formic acid; then 100 mL water/acetonitrile 5/95 with 0.5% formic acid); the acetonitrile fraction was evaporated under reduced pressure and the resulting residue was purified by flash chromatography (silica gel, eluent 0-5% of 9/1 methanol/20M ammonia in DCM) to give the title compound as white foam (0.170 g); ESMS m/z 1163.6 [M+H]$^+$.

b) 4"-O-{2-[3-(3-carboxy-1-dimethylamino-4-oxo-1,4-dihydro-quinolin-6-yl)-propyloxy]-ethylcarbamoyl}-(9S)-9-O,11-O-ethylidene-9-dihydro-erythromycin A A solution of Example 38a (0.170 g) in MeOH (5 mL) was stirred at 50° C. overnight. The solvent was removed under reduced pressure to give the title compound as a white powder (0.114 g); ESMS m/z 1121.4 [M+H]$^+$.

Example 39

4"-O-{2-[2-(3-Carboxy-1-dimethylamino-4-oxo-1,4-dihydro-quinolin-6-sulfanyl)-ethoxy]-ethylcarbamoyl}-(9E)-oxime-erythromycin A trifluoroacetate salt

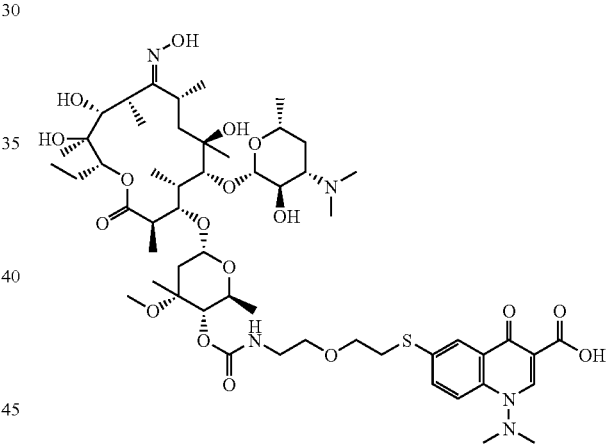

a) 2'-O-Acetyl-4"-O-{2-[2-(3-carboxy-1-dimethylamino-4-oxo-1,4-dihydro-quinolin-6-sulfanyl)-ethoxy]-ethylcarbamoyl}-(9E)-oxime-erythromycin A To a solution of Intermediate 31 (0.300 g) in dry DMF (3 mL) a solution of Intermediate 27 (0.110 g) and DBU (0.141 mL) in dry DMF (2.5 mL) was added dropwise at room temperature. The resulting mixture was stirred at room temperature for 72 h. Solvent was removed under reduced pressure and the residue was dissolved in MeOH and purified using a cartridge (10 g C18 silica gel, eluent 150 mL water/acetonitrile 95/5 with 0.5% formic acid; then 100 mL water/acetonitrile 5/95 with 0.5% formic acid); the acetonitrile fraction was evaporated under reduced pressure and the resulting residue was purified by flash chromatography (silica gel, eluent 0-10% of 9/1 methanol/20M ammonia in DCM) to give the title compound as white foam (0.130 g); ESMS m/z 1168.2 [M+H]$^+$.

b) 4''-O-{2-[2-(3-carboxy-1-dimethylamino-4-oxo-1,4-dihydro-quinolin-6-sulfanyl)-ethoxy]-ethylcarbamoyl}-(9E)-oxime-erythromycin A trifluoroacetate salt A solution of Example 39a (0.130 g) in MeOH (5 mL) was stirred at 50° C. overnight. The solvent was removed under reduced pressure and the residue was purified by reverse phase HPLC (TFA-containing eluent) to give the title compound as a white solid (0.077 g); ESMS m/z 1126.4 [M+H]$^+$.

Example 40

4''-O-{2-[3-(3-Carboxy-1-dimethylamino-4-oxo-14-dihydro-quinolin-6-yl)-propyloxy]-ethylcarbamoyl}-(9E)-oxime-erythromycin A

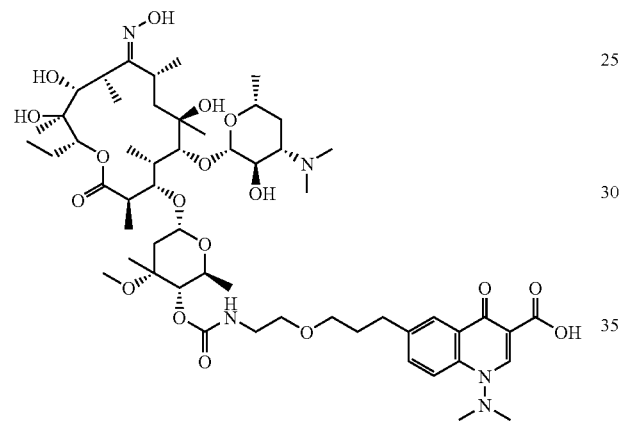

a) 2'-O-Acetyl-4''-O-{2-[3-(3-carboxy-1-dimethylamino-4-oxo-1,4-dihydro-quinolin-6-yl)-propyloxy]-ethylcarbamoyl}-(9E)-oxime-erythromycin A To a solution of Intermediate 31 (0.235 g) in dry DMF (5 mL) a solution of Intermediate 26 (0.132 g) and DBU (0.148 mL) in dry DMF (4 mL) was added dropwise at room temperature. The resulting mixture was stirred at room temperature for 72 h. Solvent was removed under reduced pressure and the residue was dissolved in MeOH and purified using a cartridge (10 g C18 silica gel, eluent 150 mL water/acetonitrile 95/5 with 0.5% formic acid; then 100 mL water/acetonitrile 5/95 with 0.5% formic acid); the acetonitrile fraction was evaporated under reduced pressure and the resulting residue was purified by flash chromatography (silica gel, eluent 0-15% of 9/1 methanol/20M ammonia in DCM) to give the title compound as a white foam (0.177 g); ESMS m/z 1150.2 [M+H]$^+$.

b) 4''-O-{2-[3-(3-Carboxy-1-dimethylamino-4-oxo-1,4-dihydro-quinolin-6-yl)-propyloxy]-ethylcarbamoyl}-(9E)-oxime-erythromycin A A solution of Example 40a (0.175 g) in MeOH (5 mL) was stirred at 50° C. overnight. The solvent was removed under reduced pressure to give the title compound as a pale yellow solid (0.170 g); ESMS m/z 1108.6 [M+H]$^+$.

Example 41

4''-O-{2-[2-(3-Carboxy-1-dimethylamino-4-oxo-14-dihydro-quinolin-6-ylsulfanyl)-ethoxy]-ethylcarbamoyl}-(9E)-O-methyloxime-erythromycin A

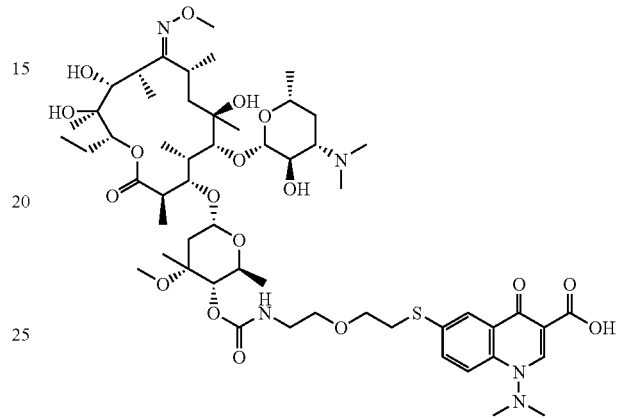

a) 2'-O-Acetyl-4''-O-{2-[2-(3-carboxy-1-dimethylamino-4-oxo-1,4-dihydro-quinolin-6-ylsulfanyl)-ethoxy]-ethylcarbamoyl}-(9E)-O-methyloxime-erythromycin A To a solution of Intermediate 28 (0.245 g) in dry DMF (4 mL) a solution of Intermediate 27 (0.095 g) and DBU (0.120 mL) in dry DMF (4 mL) was added dropwise at room temperature. The resulting mixture was stirred at room temperature for 72 h. Solvent was removed under reduced pressure and the residue was dissolved in MeOH and purified using a cartridge (10 g C18 silica gel, eluent 150 mL water/acetonitrile 95/5 with 0.5% formic acid; then 100 mL water/acetonitrile 5/95 with 0.5% formic acid); the acetonitrile fraction was evaporated under reduced pressure and the resulting residue was purified by flash chromatography (silica gel, eluent 0-10% of 9/1 methanol/20M ammonia in DCM) to give the title compound as white foam (0.118 g); ESMS m/z 1182.3 [M+H]$^+$.

b) 4''-O-{2-[2-(3-Carboxy-1-dimethylamino-4-oxo-1,4-dihydro-quinolin-6-ylsulfanyl)-ethoxy]-ethylcarbamoyl}-(9E)-O-methyloxime-erythromycin A A solution of Example 41a (0.118 g) in MeOH (5 mL) was stirred at 50° C. overnight. The solvent was removed under reduced pressure to give the title compound as an off-white solid (0.097 g); ESMS m/z 1140.6 [M+H]$^+$.

Example 42

4"-O-{2-[2-(3-Carboxy-1-dimethylamino-4-oxo-1,4-dihydro-quinolin-6-ylsulfanyl)-ethoxy]-ethylcarbamoyl}-(9E)-O-methoxymethyloxime-erythromycin A trifluoroacetate salt

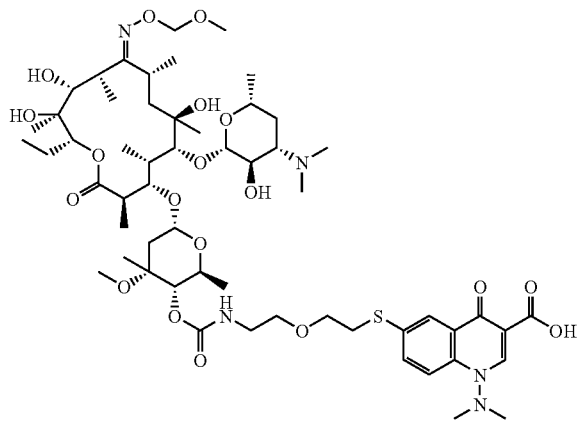

a) 2'-O-Acetyl-4"-O-{2-[2-(3-carboxy-1-dimethylamino-4-oxo-1,4-dihydro-quinolin-6-ylsulfanyl)-ethoxy]-ethylcarbamoyl}-(9E)-O-methoxymethyloxime-erythromycin A Intermediate 29 (0.250 g) was dissolved in dry DMF (4 mL) under nitrogen. To this solution a solution of Intermediate 27 (0.095 g) and DBU (0.12 mL) in dry DMF (4 mL) was added dropwise at room temperature. The resulting mixture was stirred at room temperature for 72 h. Solvent was removed under reduced pressure and the residue was dissolved in MeOH and purified using a cartridge (10 g C18 silica gel, eluent 150 mL water/acetonitrile 95/5 with 0.5% formic acid; then 100 mL water/acetonitrile 5/95 with 0.5% formic acid); the acetonitrile fraction was evaporated under reduced pressure and the resulting residue was purified by flash chromatography (silica gel, eluent 0-10% of 9/1 methanol/20M ammonia in DCM) to give the title compound as white foam (0.120 g); ESMS m/z 1212.2 [M+H]$^+$.

b) 4"-O-{2-[2-(3-Carboxy-1-dimethylamino-4-oxo-1,4-dihydro-quinolin-6-ylsulfanyl)-ethoxy]-ethylcarbamoyl}-(9E)-O-methoxymethyloxime-erythromycin A trifluoroacetate A solution of Example 42a (0.120 g) in MeOH (5 mL) was stirred at 50° C. overnight. The solvent was removed under reduced pressure and the residue was purified by reverse phase HPLC (TFA-containing eluent) to give the title compound as a white solid (0.077 g); ESMS m/z 1170.5 [M+H]$^+$.

Example 43

4"-O-{2-[2-(3-Carboxy-1-dimethylamino-4-oxo-1,4-dihydro-quinolin-6-sulfanyl)-ethoxy]-ethylcarbamoyl}-(9E)-O-(2-diethylaminoethyl)-oxime-erythromycin A

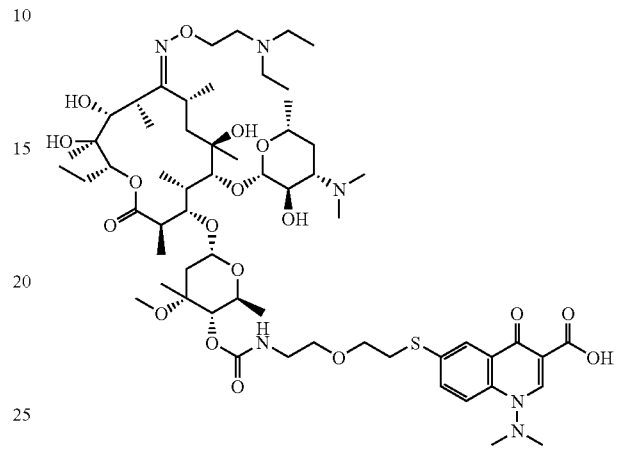

a) 2'-O-Acetyl-4"-O-{2-[2-(3-carboxy-1-dimethylamino-4-oxo-1,4-dihydro-quinolin-6-sulfanyl)-ethoxy]-ethylcarbamoyl}-(9E)-O-(2-diethylaminoethyl)-oxime-erythromycin A To a solution of Intermediate 32 (0.280 g) in dry DMF (4 mL) a solution of Intermediate 27 (0.100 g) and DBU (0.128 mL) in dry DMF (4 mL) was added dropwise at room temperature. The resulting mixture was stirred at 50° C. for 72 h. Solvent was removed under reduced pressure and the residue was dissolved in MeOH and purified using a cartridge (10 g C18 silica gel, eluent 150 mL water/acetonitrile 95/5 with 0.5% formic acid; then 100 mL water/acetonitrile 5/95 with 0.5% formic acid); the acetonitrile fraction was evaporated under reduced pressure and the resulting residue was purified by flash chromatography (silica gel, eluent 0-10% of 9/1 methanol/20M ammonia in DCM) to give the title compound as white foam (0.088 g); ESMS m/z 1267.2 [M+H]$^+$.

b) 4"-O-{2-[2-(3-Carboxy-1-dimethylamino-4-oxo-1,4-dihydro-quinolin-6-sulfanyl)-ethoxy]-ethylcarbamoyl}-(9E)-O-(2-diethylaminoethyl)-oxime-erythromycin A A solution of Example 43a (0.088 g) in MeOH (5 mL) was stirred at 50° C. overnight. The solvent was removed under reduced pressure and the residue was purified by reverse phase HPLC (TFA-containing eluent) to obtain the title compound as trifluoroacetate salt. The residue was liberated from salts on silica gel cartridge (eluent 10% of 9/1 methanol/20M ammonia in DCM) to give the title compound as a pale yellow powder (0.031 g); ESMS m/z 1224.7 [M+H]$^+$.

Example 44

4"-O-{2-[3-(3-Carboxy-1-dimethylamino-4-oxo-1,4-dihydro-quinolin-6-yl)-propyloxy]-ethylcarbamoyl}-(9E)-O-(cyanomethyl)oxime-erythromycin A

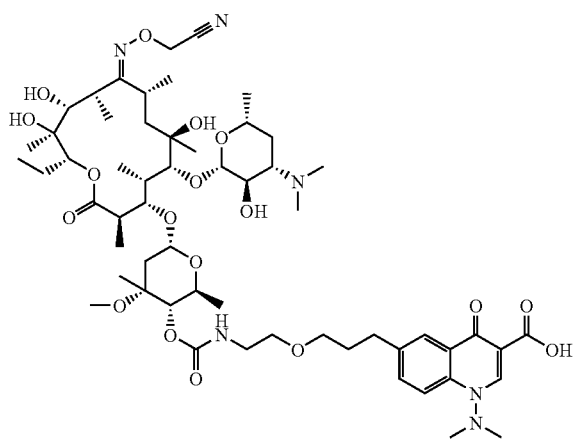

a) 2'-O-Acetyl-4"-O-{2-[3-(3-carboxy-1-dimethylamino-4-oxo-1,4-dihydro-quinolin-6-yl)-propyloxy]-ethylcarbamoyl}-(9E)-O-(cyanomethyl)oxime-erythromycin A To a solution of Intermediate 33 (0.300 g) in dry DMF (4 mL) a solution of Intermediate 26 (0.182 g) and DBU (0.198 mL) in dry DMF (4 mL) was added dropwise at room temperature. The resulting mixture was stirred at 40° C. for 20 h. Solvent was removed under reduced pressure and the residue was dissolved in MeOH and purified using a cartridge (10 g C18 silica gel, eluent 150 mL water/acetonitrile 95/5 with 0.5% formic acid; then 100 mL water/acetonitrile 5/95 with 0.5% formic acid); the acetonitrile fraction was evaporated under reduced pressure and the resulting residue was purified by flash chromatography (silica gel, eluent 0-10% of 9/1 methanol/20M ammonia in DCM) to give the title compound as white foam (0.210 g); ESMS m/z 1189.1 [M+H]$^+$.

b) 4"-O-{2-[3-(3-Carboxy-1-dimethylamino-4-oxo-1,4-dihydro-quinolin-6-yl)-propyloxy]-ethylcarbamoyl}-(9E)-O-(cyanomethyl)oxime-erythromycin A A solution of Example 44a (0.200 g) in MeOH (5 mL) was stirred at 50° C. overnight. The solvent was removed under reduced pressure and the residue was purified by reverse phase HPLC (TFA-containing eluent) to obtain the title compound as trifluoroacetate salt; the residue was liberated from salts on silica gel cartridge (eluent 10% of 9/1 methanol/20M ammonia in DCM) to give the title compound as a colourless oil (0.075 g); ESMS m/z 1147.9 [M+H]$^+$.

Example 45

4"-O-{2-[3-(3-Carboxy-1-dimethylamino-4-oxo-1,4-dihydro-quinolin-6-yl)-propyloxy]-ethylcarbamoyl}-(9E)-O-(methoxycarbonylmethyl)oxime-erythromycin A

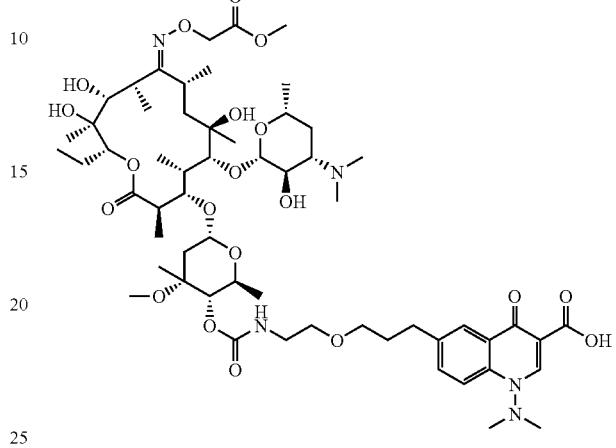

The title compound was obtained by preparative HPLC (TFA-containing eluent) from the purification of the crude of the reaction of Example 44a with methanol. The corresponding trifluoroacetate residue was liberated from salts on silica gel cartridge (eluent 10% of 9/1 methanol/20M ammonia in DCM) to give the title compound as a pale yellow oil (0.077 g); ESMS m/z 1180.9 [M+H]$^+$.

Example 46

4"-O-{2-[3-(3-carboxy-1-dimethylamino-4-oxo-1,4-dihydro-quinolin-6-yl)-propyloxy]-ethylcarbamoyl}-9-O-(2-diethylaminoethyl)-oxime-erythromycin A

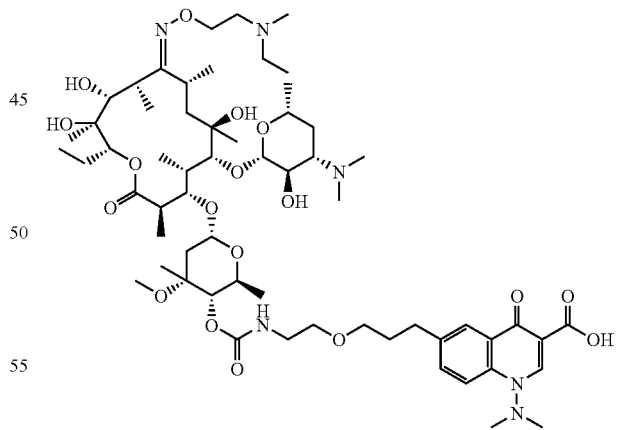

a) 2'-O-Acetyl-4"-O-{2-[3-(3-carboxy-1-dimethylamino-4-oxo-1,4-dihydro-quinolin-6-yl)-propyloxy]-ethylcarbamoyl}-(9E)-O-(2-diethylaminoethyl)-oxime-erythromycin A To a solution of Intermediate 32 (0.440 g) in dry DMF (7 mL) a solution of Intermediate 26 (0.200 g) and DBU (0.203 mL) in dry DMF (7 mL) was added dropwise at room temperature. The resulting mixture was stirred at 40° C. for 30 h. Solvent was removed under reduced pressure and the residue was dissolved in MeOH and purified using a cartridge (10 g C18 silica gel, eluent 150 mL water/acetonitrile 95/5 with 0.5% formic acid; then 100 mL water/acetonitrile 5/95 with 0.5% formic acid); the acetonitrile fraction was evaporated under reduced pressure and the resulting residue was purified by flash chromatography (silica gel, eluent 0-10% of 9/1 methanol/20M ammonia in DCM) to give the title compound as white foam (0.390 g); ESMS m/z 1249.4 [M+H]$^+$.

b) 4"-O-{2-[3-(3-Carboxy-1-dimethylamino-4-oxo-1,4-dihydro-quinolin-6-yl)-propyloxy]-ethylcarbamoyl}-(9E)-O-(2-diethylaminoethyl)-oxime-erythromycin A A solution of Example 46a (0.290 g) in MeOH (5 mL) was stirred at 50° C. overnight. The solvent was removed under reduced pressure and the residue was purified by reverse phase HPLC (TFA-containing eluent) to give the title compound as trifluoroacetate salt. The residue was liberated from salts on silica gel cartridge (eluent 10% of 9/1 methanol/20M ammonia in DCM) to give the title compound as a white powder (0.120 g); ESMS m/z 1208.0 [M+H]$^+$.

Example 47

4"-O-{3-[[3-(3-Carboxy-1,4-dihydro-1-dimethylamino-4-oxo-6-quinolinyl)propyl]-methylamino]propionyl}-6-O-methyl-erythromycin A

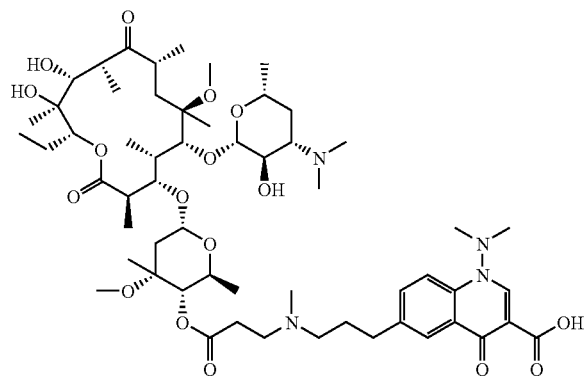

A mixture of Example 1 (0.218 g) in chloroform (3 mL), formaldehyde (37% in water, 0.030 mL) and formic acid (0.028 mL) was heated at 60° C. for 2 h. The mixture was concentrated and the residue chromatographed on silica gel eluting with 0-15% (9:1 methanol/0.880 ammonia) in DCM to give the title compound as a white solid (0.18 g); ESMS m/z 553.8 [M+2H]$^{2+}$.

Example 48

4"-O-{2-[3-(3-Carboxy-1,4-dihydro-1-dimethylamino-4-oxo-6-quinolinyl)propyl-cyclopropylamino]ethyl}-azithromycin

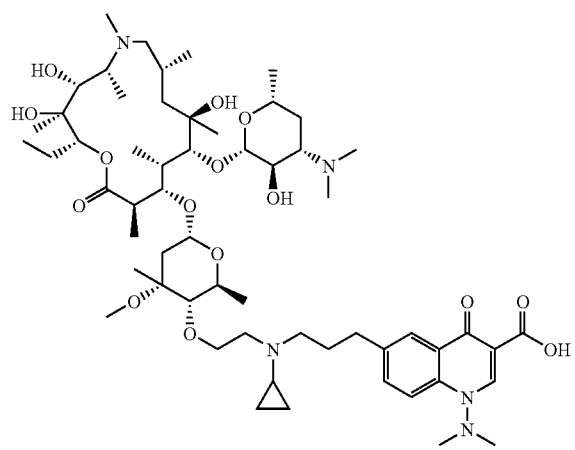

a) 2'-O-Acetyl-4"-O-(2-oxoethyl)-azithromycin-11,12-carbonate

Intermediate 35 (9.0 g) in DCM (200 mL) and methanol (20 mL) was cooled to −78° C. and TFA (3.2 mL) added. Ozone was bubbled through until a blue colour developed (1 h). Argon was bubbled through the mixture to flush out the ozone, then dimethyl sulfide (3.1 mL) and triethylamine (6.6 mL) were added. The reaction was stirred at −78° C. for 15 min then removed from the cooling bath and warmed to room temperature. The reaction mixture was washed successively with a saturated aqueous solution of sodium bicarbonate, water and brine then dried and evaporated under reduced pressure to dryness to give crude title compound (9.5 g) which was used without purification ESMS m/z 891.8 [M+MeOH+H]$^+$.

b) 2'-O-Acetyl-4"-O-{2-[[3-(3-carboxy-1,4-dihydro-1-dimethylamino-4-oxo-6-quinolinyl)propyl]-cyclopropylamino]ethyl}-azithromycin 11,12-carbonate ethyl ester Intermediate 48a (0.3 g) in DCM (10 mL) was stirred under argon with Intermediate 37 (0.125 g) and 3 A molecular sieves (0.3 g) for 30 min. Sodium triacetoxy borohydride (0.148 g) was added followed one minute later by acetic acid (2 drops). After stirring at room temperature for 16 h the mixture was filtered, evaporated under reduced pressure and the residue chromatographed eluting with 0-10% (10:1 methanol/0.880 ammonia) in DCM to give the title compound (0.237 g); ESMS m/z 1244.9 [M+HCO$_2$]$^−$.

c) 4"-O-{2-[[3-(3-Carboxy-1,4-dihydro-1-dimethylamino-4-oxo-6-quinolinyl)propyl]-cyclopropylamino]ethyl}-azithromycin Example 48b (0.24 g) in acetonitrile (5 mL) was treated with a 10% aqueous solution of potassium carbonate (4 mL) at 85° C. for 16 h. The acetonitrile was removed under vacuum and the residue partitioned between water and DCM.

The organic layer was dried, evaporated under reduced pressure and the residue chromatographed eluting with 0-10% (10:1 methanol/0.880 ammonia) in DCM to give the title compound as an off-white solid (0.068 g); ESMS m/z 1103.1 [M−H]⁻.

Example 49

4''-O-{2-[3-(3-Carboxy-1,4-dihydro-1-dimethylamino-4-oxo-6-quinolinyl)propyl]-oxyethyl}-azithromycin

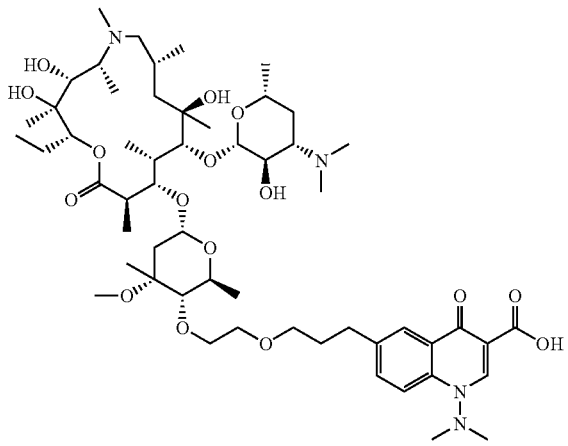

a) 2'-O-Acetyl-4''-O-(2-hydroxyethyl)-azithromycin 11,12-carbonate

Example 48a (5.0 g) was dissolved in methanol (75 mL) and cooled in an ice-bath before the addition of sodium borohydride (1.25 g). After 1 h water (5 mL) was added and the mixture evaporated under reduced pressure to dryness. The residue was partitioned between brine and DCM. The organic layer was dried, evaporated under reduced pressure and the residue chromatographed eluting with 0-7.5% methanol in DCM to give the title compound (2.8 g); ESMS m/z 861.5 [M+H]⁺.

b) 2'-O-Acetyl-4''-O-(2-allyloxyethyl)-azithromycin 11,12-carbonate

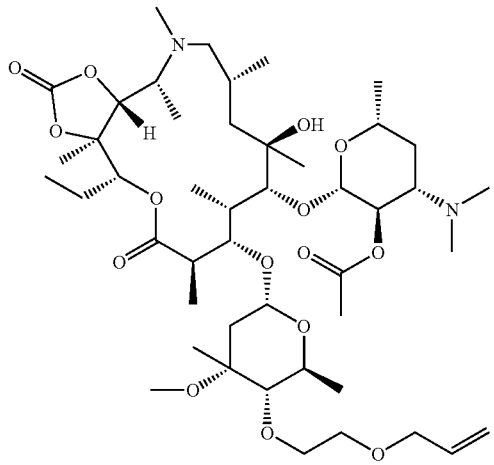

Example 49a (0.67 g) in dry THF (1 mL) under argon was treated with allyl t-butyl carbonate (1.2 mL) and tetrakis(triphenylphosphine)palladium (0.15 g). The resultant mixture was heated at reflux for 0.75 h. After cooling the reaction mixture was evaporated under reduced pressure and the residue chromatographed eluting with 0-7% methanol in DCM to give 2'-O-acetyl-4''-O-(2-allyloxycarbonyloxyethyl)-azithromycin 11,12-carbonate which was dissolved in dry THF (1 mL) under argon, treated with allyl t-butyl carbonate (1.5 mL) and tetrakis(triphenylphosphine)palladium (0.15 g). The resultant mixture was heated at reflux for 2 h. After cooling the reaction mixture was evaporated under reduced pressure and the residue chromatographed eluting with 0-5% methanol in DCM to give the title compound (0.44 g); ESMS m/z 901.9 [M+H]⁺.

c) 2'-O-Acetyl-4''-O-{2-[3-(3-carboxy-1,4-dihydro-1-dimethylamino-4-oxo-6-quinolinyl)prop-1-enyl]-oxyethyl}-azithromycin 11,12-carbonate ethyl ester A solution of triethylamine (0.63 mL) in dry acetonitrile (4 mL) was degassed by bubbling argon while ultrasonicating for 5 min. To this solution was added Intermediate 1c (0.35 g), triphenyl phosphine (0.008 g) and sodium bicarbonate (0.077 g). A degassed solution of Example 49b (0.41 g) in dry acetonitrile (10 mL) was added to the above solution followed by palladium diacetate (0.024 g). The reaction was refluxed for 2 h after which further palladium acetate (0.024 g) was added. After a further 2 h, further palladium acetate (0.024 g) was added. The reaction was refluxed for a further 1 h, cooled, filtered through celite and evaporated under reduced pressure to dryness to give the crude title compound which was used without purification (0.8 g); ESMS m/z 1159.7 [M+H]⁺.

d) 2'-O-Acetyl-4''-O-{2-[3-(3-carboxy-1,4-dihydro-1-dimethylamino-4-oxo-6-quinolinyl)propyl]-oxyethyl}-azithromycin 11,12-carbonate ethyl ester Crude Example 49c (0.8 g) in a 1:1 mixture of DCM and methanol (80 mL) was treated with 10% Pd/C (0.5 g). After 5 min the catalyst was filtered through celite and replaced with fresh 10% Pd/C (0.5 g) then hydrogenated at 20° C. and 1 atm for 5 h. The reaction was filtered through Celite and concentrated to give the crude title compound which was used without purification (0.62 g); ESMS m/z 1161.7 [M+H]⁺.

e) 4''-O-{2-[3-(3-Carboxy-1,4-dihydro-1-dimethylamino-4-oxo-6-quinolinyl)propyl]-oxyethyl}-azithromycin Crude Example 49d (0.62 g) in acetonitrile (20 mL) was treated with 10% aqueous solution of potassium carbonate (10 mL) and heated at 85° C. for 40 h. The mixture was cooled down then the pH adjusted to 6 by adding a 10% aqueous solution of citric acid. Acetonitrile was evaporated under reduced pressure and the residue was partitioned between DCM and water. The organic phase was dried concentrated and the residue chromatographed eluting with 0-10% (10:1 methanol/0.880 ammonia) in DCM to give the impure product. Further purification by mass directed automatic preparative HPLC followed by normal phase chromatography as above gave the pure title compound as a white solid (0.095 g); ESMS m/z 1065.5 [M+H]⁺.

Example 50

4"-O-{3-[3-(3-Carboxy-1-dimethylamino-1,4-dihydro-4-oxo-6-quinolinyl) propylamino]propionyl}-erythromycin A (9E)-2-(diethylamino)ethyloxime

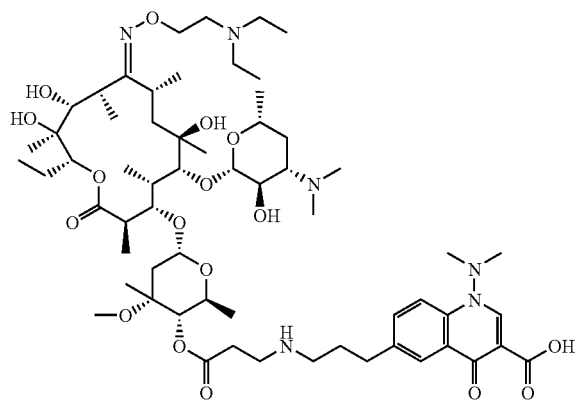

A mixture of Intermediate 36 (0.25 g), Intermediate 1 (0.127 g) and triethylamine (0.4 mL) in DMSO (3 mL) were stirred together at 85° C. for 28 h. The mixture was evaporated under reduced pressure to dryness and the residue was purified by mass directed automatic preparative HPLC followed by chromatography on silica gel eluting with 0-12% (9:1 methanol/0.880 ammonia) in DCM to give the title compound as a white solid (0.117 g); ESMS m/z 596.7 $[M+2H]^{2+}$.

Example 51

4"-O-{3-[2-(3-Carboxy-1-dimethylamino-1,4-dihydro-4-oxo-7-quinolinyl)oxyethylamino]propionyl}-erythromycin A (9E)-2-(diethylamino)ethyloxime

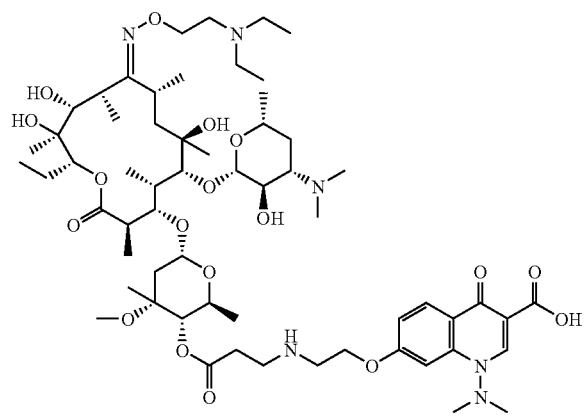

Using a similar procedure to that described in Example 50, Intermediate 36 (0.25 g) and Intermediate 12 (0.133 g) gave the title compound as a white solid (0.105 g); ESMS m/z 597.8 $[M+2H]^{2+}$.

Example 52

4"-O-{3-[2-{[6-Carboxy-8-dimethylamino-5-oxo-5,8-dihydro-1,8-naphthyridin-3-yl]thio}ethylamino]propionyl}-erythromycin A (9E)-2-(diethylamino)ethyloxime

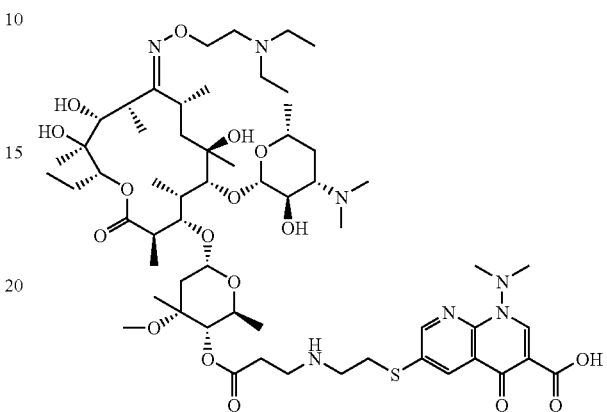

Using a similar procedure to that described in Example 50, Intermediate 36 (0.25 g) and Intermediate 19 (0.164 g) gave the title compound as a white solid (0.013 g); ESMS m/z 606.3 $[M+2H]^{2+}$.

Example 53

4"-O-{3-[3-[6-Carboxy-8-(dimethylamino)-5-oxo-5,8-dihydro-1,8-naphthyridin-3-yl])propylamino]propionyl}-erythromycin A (9E)-2-(diethylamino)ethyloxime

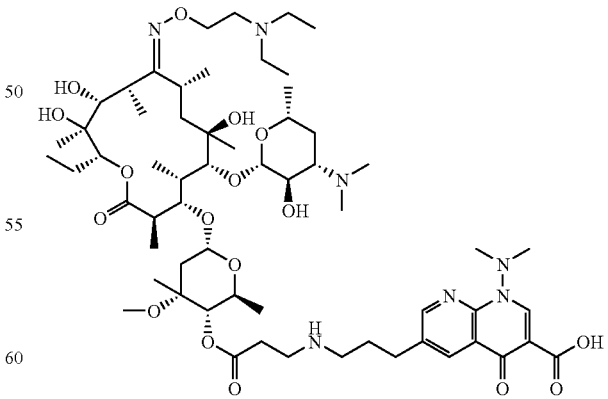

Using a similar procedure to that described in Example 50, Intermediate 36 (0.25 g) and Intermediate 20 (0.157 g) gave the title compound as a white solid (0.086 g); ESMS m/z 597.2 $[M+2H]^{2+}$.

Example 54

4"-O-{3-[3-(3-Carboxy-1-dimethylamino-14-dihydro-4-oxo-6-quinolinyl) propylamino]propionyl}-erythromycin A (9E)-2-(N-morpholinyl)ethyloxime

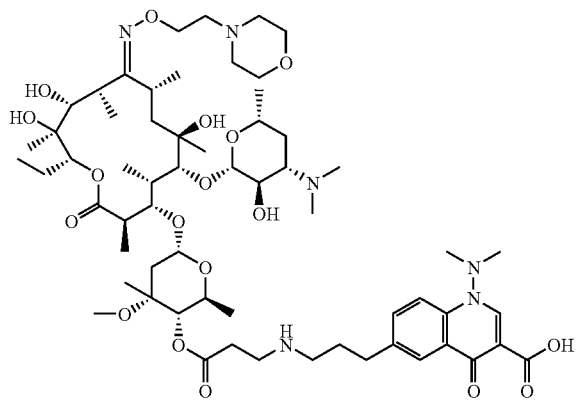

Using a similar procedure to that described in Example 50, Intermediate 34 (0.30 g) and Intermediate 1 (0.15 g) gave the title compound as a white solid (0.239 g); ESMS m/z 603.7 [M+2H]$^{2+}$.

Example 55

4"-O-{2-[[3-(3-Carboxy-1-dimethylamino-1,4-dihydro-4-oxo-6-quinolinyl) propyl]methylamino]ethyl}-azithromycin

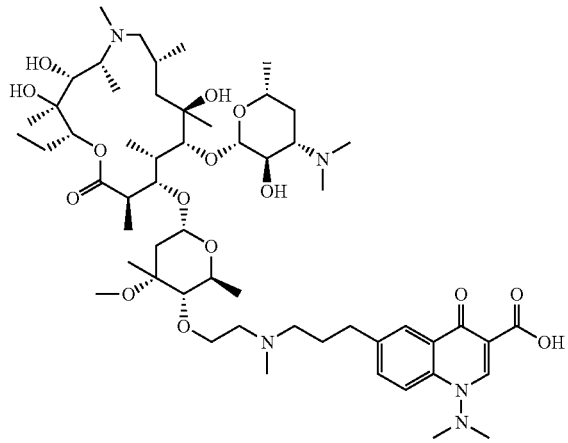

a) 4"-O-{2-[3-(3-Carboxy-1-dimethylamino-1,4-dihydro-4-oxo-6-quinolinyl) propylamino]ethyl}-azithromycin-11,12-carbonate A mixture of Example 48a (0.64 g), Intermediate 1 (0.326 g) and sodium acetate (0.18 g) in methanol (15 mL) was stirred for 5 min. Sodium cyanoborohyride (0.094 g, 1.5 mmol) was added and then after 5 min acetic acid (0.13 mL) was added, and the reaction was stirred for 16 h. The mixture was evaporated under reduced pressure onto silica gel and the residue purified by chromatography on silica gel eluting with 0-17% (9:1 methanol/0.880 ammonia) in DCM to give the title compound (0.244 g); ESMS m/z 546.3 [M+2H]$^{2+}$.

b) 4"-O-{2-[[3-(3-Carboxy-1-dimethylamino-1,4-dihydro-4-oxo-6-quinolinyl) propyl]methylamino]ethyl}-azithromycin-11,12-carbonate Aqueous formaldehyde (37%) (0.035 mL) and then formic acid (0.035 mL) were added to a mixture of Example 55a (0.233 g, 0.214 mmol) in chloroform (3 mL) and the resultant mixture stirred at 60° C. for 16 hours. The mixture was concentrated and the residue purified by chromatography on silica gel eluting with 0-16% (9:1 methanol/20M aq. ammonia) in DCM to give the title compound (0.061 g); ESMS m/z 553.2 [M+2H]2$^{+}$.

c) 4"-O-{2-[[3-(3-Carboxy-1-dimethylamino-1,4-dihydro-4-oxo-6-quinolinyl) propyl]methylamino]ethyl}-azithromycin Example 55b (0.059 g, 0.0534 mmol) in a mixture of 10% aqueous potassium carbonate (4 mL) and acetonitrile (6 mL) was stirred at 85° C. for 16 hours. The mixture was concentrated and the residue partitioned between dichlomethane and brine. The organic phase was dried over magnesium sulphate and concentrated. The residue was purified by chromatography on silica gel eluting with 0-16% (9:1 methanol/20M aq. ammonia) in DCM to give the title compound as a white solid (0.020 g); ESMS m/z 540.1 [M+2H]$^{2+}$.

It will be understood that in the context of the examples used to illustrate the invention that information about how the compounds were prepared cannot be drawn from the format used to present the information, for example, the intermediates and final products may have been prepared by different individuals, or at different timepoints, employing appropriate techniques.

Biological Data

Using a standard broth dilution method in microtitre, compounds were tested for antibacterial activity (i.e. MICs were determined by the Clinical and Laboratory Standards Institute standards). The compounds in the above examples gave minimum inhibitory concentrations (MICs) less than 1 microgram per milliliter against erythromycin-sensitive and erythromycin-resistant strains of *Streptococcus pneumoniae* and/or *Streptococcus pyogenes*.

However, it will appreciated by person skilled in the art that compounds of the invention may have different levels of activity against different strains of the same bacteria.

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims:

The invention claimed is:
1. A compound of formula (I)

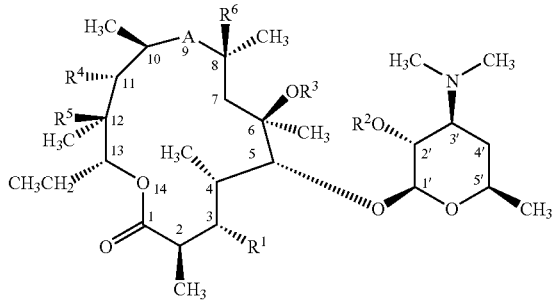

wherein
A is a bivalent radical —C(O)—, —N(R⁷)—CH₂—, —CH(NR⁸R⁹)— or —C(=NR¹⁰)—, or A and R⁴ taken together with the intervening atoms form a cyclic group having the following formula:

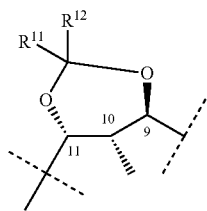

and R¹ is a group having the following formula:

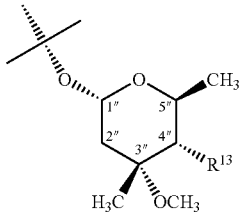

wherein R¹³ is —OC(O)(CH₂)$_d$U¹R¹⁴, —OC(O)N(R¹⁵)(CH₂)$_d$U¹R¹⁴, —O(CH₂)$_d$U¹R¹⁴,

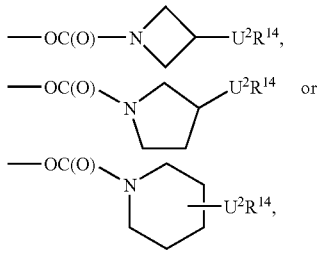

or
A is the bivalent radical —N(R⁷)—CH₂— and R¹ is a group having the following formula:

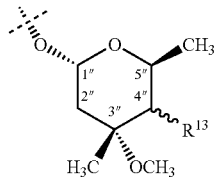

wherein R¹³ is —NHC(O)(CH₂)$_d$U¹R¹⁴;
R² is hydrogen or a hydroxyl protecting group;
R³ is hydrogen, C$_{1-4}$alkyl, or C$_{3-6}$alkenyl optionally substituted by 9- or 10-membered fused bicyclic heteroaryl;
R⁴ is hydroxy, C$_{3-6}$alkenyloxy optionally substituted by 9- or 10-membered fused bicyclic heteroaryl, or C$_{1-6}$alkoxy optionally substituted by C$_{1-6}$alkoxy or —O(CH₂)$_e$NR⁷R¹⁶, or R⁴ and A taken together with the intervening atoms form a cyclic group of formula (IA),
R⁵ is hydroxy, or
R⁴ and R⁵ taken together with the intervening atoms form a cyclic group having the following formula:

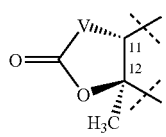

wherein V is a bivalent radical —CH₂—, —CH(CN)—, —O—, —N(R¹⁷)— or —CH(SR¹⁷)—, with the proviso that when R¹ is a group of formula (IC), V is —O—;
R⁶ is hydrogen or fluorine;
R⁷ is hydrogen or C$_{1-6}$alkyl;
R⁸ and R⁹ are each independently hydrogen, C$_{1-6}$alkyl or —C(O)R¹⁸, or
R⁸ and R⁹ together form =CH(CR¹⁸R¹⁹)$_f$aryl, =CH(CR¹⁸R¹⁹)$_f$heterocyclyl, =CR¹⁸R¹⁹ or =C(R¹⁸)C(O)OR⁸, wherein the alkyl, aryl and heterocyclyl groups are optionally substituted by up to three groups independently selected from R²⁰;
R¹⁰ is —OR²¹;
R¹¹ and R¹² are each independently hydrogen, C$_{1-6}$alkyl, heteroaryl, or aryl optionally substituted by one or two groups independently selected from hydroxyl and C$_{1-6}$alkoxy;
R¹⁴ is a heterocyclic group having the following formula:

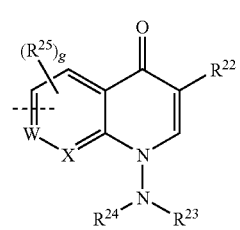

wherein W is —C(R⁴¹)— and X is —C(R⁴¹)— or N, with the proviso that when X is —C(R⁴¹)R¹⁴ is linked at the 5-, 6-, 7-, or 8-position and when X is N, R¹⁴ is linked at the 2-, 3-, or 4-position;

$R^{15}$, $R^{16}$, $R^{18}$ and $R^{19}$ are each independently hydrogen or $C_{1-6}$alkyl;

$R^{17}$ is hydrogen or $C_{1-4}$alkyl optionally substituted by a group selected from optionally substituted phenyl, optionally substituted 5- or 6-membered heteroaryl and optionally substituted 9- or 10-membered fused bicyclic heteroaryl;

$R^{20}$ is halogen, cyano, nitro, trifluoromethyl, azido, —C(O)R$^{26}$, —C(O)OR$^{26}$, —OC(O)R$^{26}$, —C(O)OR$^{26}$, —NR$^{27}$C(O)R$^{28}$, —C(O)NR$^{27}$R$^{28}$, —NR$^{27}$R$^{28}$, hydroxy, $C_{1-6}$alkyl, —S(O)$_h$$C_{1-6}$alkyl, $C_{1-6}$alkoxy, —(CH$_2$)$_i$aryl or —(CH$_2$)$_i$heteroaryl, wherein the alkoxy group is optionally substituted by up to three groups independently selected from —NR$^{18}$R$^{19}$, halogen and —OR$^{18}$, and the aryl and heteroaryl groups are optionally substituted by up to five groups independently selected from halogen, cyano, nitro, trifluoromethyl, azido, —C(O)R$^{29}$, —C(O)OR$^{29}$, —OC(O)OR$^{29}$, —NR$^{30}$C(O)R$^{31}$, —C(O)NR$^{30}$R$^{31}$, —NR$^{30}$R$^{31}$, hydroxy, $C_{1-6}$alkyl and $C_{1-6}$alkoxy;

$R^{21}$ is hydrogen, $C_{1-6}$alkyl, $C_{3-7}$cycloalkyl, $C_{3-6}$alkenyl or a 5- or 6-membered heterocyclic group, wherein the alkyl, cycloalkyl, alkenyl and heterocyclic groups are optionally substituted by up to three groups independently selected from optionally substituted 5- or 6-membered heterocyclic group, optionally substituted 5- or 6-membered heteroaryl, —OR$^{32}$, —S(O)$_j$R$^{32}$, —NR$^{32}$R$^{33}$, —CONR$^{32}$R$^{33}$, halogen and cyano;

$R^{22}$ is hydrogen, —C(O)OR$^{34}$, —C(O)NHR$^{34}$, —C(O)CH$_2$NO$_2$ or —C(O)CH$_2$SO$_2$R$^7$;

$R^{23}$ and $R^{24}$ are each independently hydrogen, $C_{1-4}$alkyl or $C_{3-7}$cycloalkyl, wherein the alkyl and cycloalkyl groups are optionally substituted by up to three groups independently selected from hydroxy, cyano, $C_{1-4}$alkoxy, —CONR$^{35}$R$^{36}$ and —NR$^{35}$R$^{36}$, $R^{23}$ and $R^{24}$, together with the nitrogen atom to which they are bound, form a 5- or 6-membered heterocyclic ring optionally containing one additional heteroatom selected from oxygen, sulfur and N—R$^{37}$, or $R^{23}$ is $C_{1-4}$alkyl, X is —C(R$^{41}$)—, and $R^{24}$ and $R^{41}$ are linked to form an R$^{14}$ tricyclic group having the following formula:

(IF)

(IF-a)

$R^{25}$ is halogen, $C_{1-4}$alkyl, $C_{1-4}$thioalkyl, $C_{1-4}$alkoxy, —NH$_2$, —NH($C_{1-4}$alkyl) or —N($C_{1-4}$alkyl)$_2$;

$R^{26}$ is hydrogen, $C_{1-10}$alkyl, —(CH$_2$)$_k$aryl or —(CH$_2$)$_k$heteroaryl;

$R^{27}$ and $R^{28}$ are each independently hydrogen, —OR$^{18}$, $C_{1-6}$alkyl, —(CH$_2$)$_m$aryl or —(CH$_2$)$_m$heterocyclyl;

$R^{29}$ is hydrogen, $C_{1-10}$alkyl, —(CH$_2$)$_n$aryl or —(CH$_2$)$_n$heteroaryl;

$R^{30}$ and $R^{31}$ are each independently hydrogen, —OR$^{18}$, $C_{1-6}$alkyl, —(CH$_2$)$_p$aryl or —(CH$_2$)$_p$heterocyclyl;

$R^{32}$ and $R^{33}$ are each independently hydrogen, $C_{1-4}$alkyl or $C_{1-4}$alkoxy$C_{1-4}$alkyl;

$R^{34}$ is hydrogen, $C_{1-6}$alkyl optionally substituted by up to three groups independently selected from halogen, cyano, $C_{1-4}$alkoxy optionally substituted by phenyl or $C_{1-4}$alkoxy, —C(O)$C_{1-6}$alkyl, —C(O)O$C_{1-6}$alkyl, —OC(O)$C_{1-6}$alkyl, —OC(O)O$C_{1-6}$alkyl, —C(O)NR$^{38}$R$^{39}$, —NR$^{38}$R$^{39}$ and phenyl optionally substituted by nitro or —C(O)O$C_{1-6}$alkyl, —(CH$_2$)$_q$$C_{3-7}$cycloalkyl, —(CH$_2$)$_q$heterocyclyl, —(CH$_2$)$_q$heteroaryl, —(CH$_2$)$_q$aryl, $C_{3-6}$alkenyl, or $C_{3-6}$alkynyl;

$R^{35}$ and $R^{36}$ are each independently hydrogen or $C_{1-4}$alkyl;

$R^{37}$ is hydrogen or methyl;

$R^{38}$ and $R^{39}$ are each independently hydrogen or $C_{1-6}$alkyl optionally substituted by phenyl or —C(O)O$C_{1-6}$alkyl, or $R^{38}$ and $R^{39}$, together with the nitrogen atom to which they are bound, form a 5- or 6-membered heterocyclic group optionally containing one additional heteroatom selected from oxygen, sulfur and N—R$^{37}$;

$R^{40}$ is hydrogen, $C_{1-4}$alkyl, $C_{3-7}$cycloalkyl, optionally substituted phenyl or benzyl, acetyl or benzoyl;

$R^{41}$ is hydrogen or $R^{25}$, or, when X is —C(R$^{41}$)—, $R^{41}$ and $R^{24}$ may be linked to form a cyclic group of formula (IF);

$U^1$ is a bivalent radical —Y(CH$_2$)$_r$Z— or —Y(CH$_2$)$_r$—;

$U^2$ is $U^1$ or a bivalent radical —O—, —N(R$^{40}$)—, —S(O)$_s$— or —CH$_2$—;

Y and Z are each independently a bivalent radical —N(R$^{40}$)—, —O—, —S(O)$_s$—, —N(R$^{40}$)C(O)—, —C(O)N(R$^{40}$)— or —N[C(O)R$^{40}$]—;

d is an integer from 2 to 5;

e is an integer from 2 to 4;

f, i, k, m, n, p and q are each independently integers from 0 to 4;

g, h, j and s are each independently integers from 0 to 2;

r is an integer from 2 to 5;

or a pharmaceutically acceptable salt thereof.

2. A process for the preparation of a compound as claimed in claim 1 or a pharmaceutically acceptable salt thereof, which comprises:

(a) reacting a compound of formula (XII), wherein $R^2$ is H or a hydroxyl protecting group, (XII)

with a compound of formula $HU^{1z}R^{14z}$ (VIII) wherein $R^{14z}$ is $R^{14}$ or a protected $R^{14}$ group; $U^{1z}$ is $Y(CH_2)_rZ$ or —$Y(CH_2)_r$— or a protected $Y(CH_2)_rZ$ or —$Y(CH_2)_r$— group in which Y is —$N(R^{40})$— or —S—, to produce a compound of formula (I) wherein r is 2 and Y is —$N(R^{40})$— or —S—; or (b) reacting compound of formula (IIC)

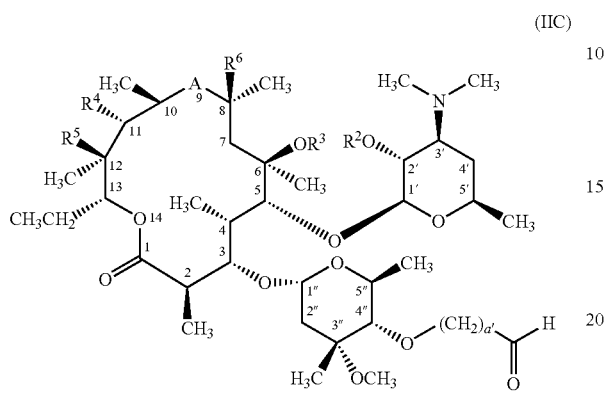
(IIC)

with a suitable amine (V) or (VA) in the presence of a reducing agent,

wherein $Z^z$ and $R^{14z}$ are Z and $R^{14}$ respectively or protected Z and $R^{14}$ groups respectively; or (c) reacting a compound of formula (X)

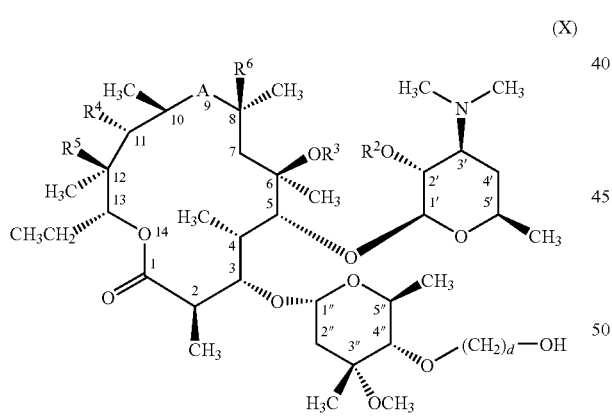
(X)

with a compound of formula (XI)

(XI)

in which L is a suitable leaving group in the presence of a catalyst,
and thereafter, if required, removing the $R^2$ protecting group; and/or deprotecting $U^{1z}R^{14z}$ to form $U^1R^{14}$; and/or converting the resultant compound of formula (I) to a pharmaceutically acceptable salt.

3. A process according to claim 2 wherein $R^{14z}$ is $R^{14}$; $U^{1z}$ is $Y(CH_2)_rZ$ or —$Y(CH_2)_r$—; and $Z^z$ is Z.

4. A method for the treatment of the human or non-human body to combat bacterial infections comprising administration to a body in need of such treatment of an effective amount of a compound as claimed in claim 1, or a pharmaceutically acceptable salt thereof.

5. A pharmaceutical composition comprising a compound as claimed in claim 1 or a pharmaceutically acceptable salt thereof, in association with a pharmaceutically acceptable excipient, diluent and/or carrier.

6. A compound of the formula (I) as claimed in claim 1:

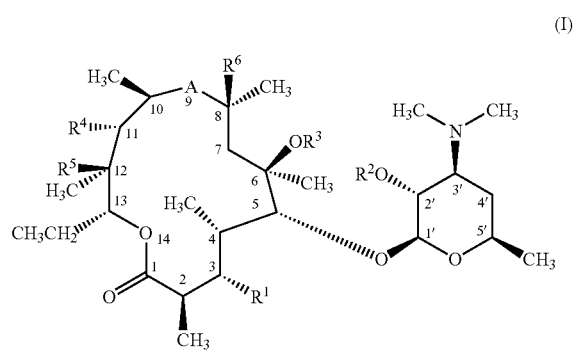
(I)

or a pharmaceutically acceptable salt thereof, wherein:

A is a bivalent radical —C(O)—, —$N(R^7)$—$CH_2$—, or —C(=$NR^{10}$)—, or A and $R^4$ taken together with the intervening atoms form a cyclic group having the following formula:

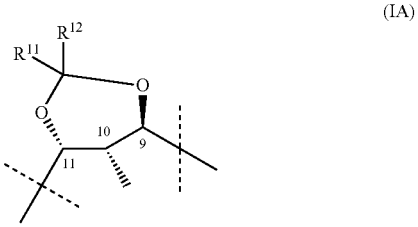
(IA)

and $R^1$ is a group having the following formula:

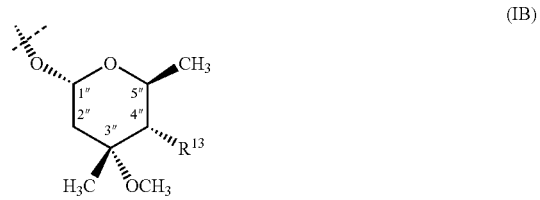
(IB)

wherein $R^{13}$ is —$OC(O)(CH_2)_dU^1R^{14}$, —$OC(O)N(R^{15})(CH_2)_dU^1R^{14}$, —$O(CH_2)_dU^1R^{14}$;

$R^2$ is hydrogen or a hydroxyl protecting group;

$R^3$ is hydrogen, $C_{1-4}$alkyl;

$R^4$ is hydroxy, $C_{1-6}$alkoxy, or $R^4$ and A taken together with the intervening atoms form a cyclic group of formula (IA), $R^5$ is hydroxy, or $R^4$ and $R^5$ taken together with the intervening atoms form a cyclic group having the following formula:

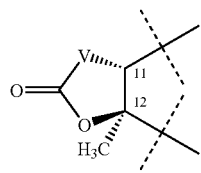
(ID)

wherein V is a bivalent radical —CH$_2$—, —O— or —N(R$^{17}$)—;

R$^6$ is hydrogen or fluorine;

R$^7$ is hydrogen or C$_{1-6}$alkyl;

R$^{10}$ is —OR$^{21}$;

R$^{11}$ and R$^{12}$ are each independently hydrogen, C$_{1-6}$alkyl;

R$^{14}$ is a heterocyclic group having the following formula:

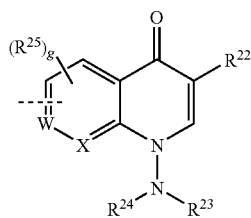
(IE)

wherein W is —C(R$^{41}$) and X is —C(R$^{41}$)— or N, with the proviso that when X is —C(R$^{41}$), R$^{14}$ is linked at the 5-, 6-, or 7-position and when X is N, R$^{14}$ is linked at the 2-, 3-, or 4-position;

R$^{17}$ is hydrogen or C$_{1-4}$alkyl;

R$^{21}$ is hydrogen, —CH$_2$CN, C$_{1-6}$alkyl, or C$_{1-6}$alkyl optionally substituted with OR$^{32}$ or NR$^{32}$R$^{33}$;

R$^{22}$ is hydrogen, —C(O)OR$^{34}$, —C(O)NHR$^{34}$;

R$^{23}$ and R$^{24}$ are each independently hydrogen, C$_{1-4}$alkyl or R$^{23}$ and R$^{24}$, together with the nitrogen atom to which they are bound, form a 5- or 6-membered heterocyclic ring optionally containing one additional heteroatom selected from oxygen, sulfur and N—R$^{37}$, or R$^{24}$ and X are linked to form a cyclic group having the following formula:

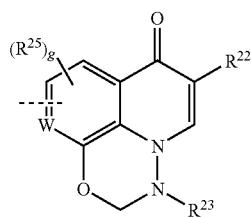
(IF)

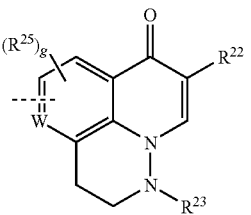
(IF-a)

R$^{25}$ is halogen, C$_{1-4}$alkyl, C$_{1-4}$thioalkyl, C$_{1-4}$alkoxy, —NH$_2$, —NH(C$_{1-4}$alkyl) or —N(C$_{1-4}$alkyl)$_2$;

R$^{32}$ and R$^{33}$ are each independently hydrogen, C$_{1-4}$alkyl, or C$_{1-4}$alkoxyC$_{1-4}$alkyl;

R$^{34}$ hydrogen or C$_{1-6}$alkyl;

R$^{37}$ hydrogen or methyl;

R$^{40}$ is hydrogen, C$_{1-4}$alkyl or C$_{3-7}$cycloalkyl;

X is a carbon, a nitrogen or X and R$^{24}$ may be linked to form a cyclic group of formula (IF) or (IF-a);

U$^1$ is a bivalent radical —Y(CH$_2$)$_r$Z— or —Y(CH$_2$)$_r$—;

Y and Z are each independently a bivalent radical —N(R$^{40}$)—, —O—, —S(O)$_s$—, —N(R$^{40}$)C(O)—, —C(O)N(R$^{40}$)— or —N[C(O)R$^{40}$]—;

W is CH, C—R$^{25}$, or N;

d is an integer from 2 to 5;

g and s are each independently 0, 1, or 2; and r is 2, 3, 4, or 5;

or a pharmaceutically acceptable salt thereof.

7. A compound according to claim 6 or a pharmaceutically acceptable salt thereof wherein A is —C(O)—, —N(R$^7$)—CH$_2$— or —C(=NR$^{10}$)—.

8. A compound according to claim 7 or a pharmaceutically acceptable salt thereof wherein U$^1$ is —Y(CH$_2$)$_r$—.

9. A compound according to claim 8 or a pharmaceutically acceptable salt thereof wherein r is 3.

10. A compound according to claim 9 or a pharmaceutically acceptable salt thereof wherein R$^{14}$ is a heterocyclic group of the following formula:

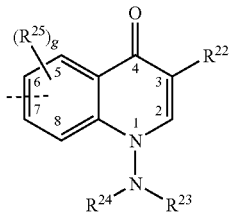

wherein the heterocyclic is linked in the 6 or 7 position.

11. A compound according to claim 10 or a pharmaceutically acceptable salt thereof wherein R$^{23}$ and R$^{24}$ are each independently hydrogen or C$_{1-4}$alkyl.

12. A compound which is:

4"-O-{3-[3-(3-Carboxy-1,4-dihydro-1-dimethylamino-4-oxo-6-quinolinyl)propylamino]propionyl}-6-O-methylerythromycin A, 4"-O-{3-[3-(3-Carboxy-1,4-dihydro-1-dimethylamino-4-oxo-7-quinolinyl)propylamino]propionyl}-azithromycin-11,12-carbonate, 4"-O-{3-[3-(3-Carboxy-1,4-dihydro-1-(morpholin-4-yl)-4-oxo-6-quinolinyl)propylamino]propionyl}-6-O-methylerythromycin A, 4"-O-{3-[3-(3-Carboxy-1,4-dihydro-1-methylamino-4-oxo-6-quinolinyl)propylamino]propionyl}-6-O-methylerythromycin A, 4"-O-{3-[3-(3-Carboxy-1,4-dihydro-1-dimethylamino-4-oxo-6-quinolinyl)propylamino]propionyl}-erythromycin A (9E)-oxime, 4"-O-{3-[3-(3-Carboxy-1,4-dihydro-1-dimethylamino-4-oxo-6-quinolinyl)propylamino]propionyl}-erythromycin A (9E)-methoxime, 4"-O-[3-[3-(3-Carboxy-1-(N,N-dimethylamino)-1,4-dihydro-4-oxo-6-quinolinyl)propylaminopropionyl]-6-O-methyl erythromycin A (9E)-oxime, 4"-O-{3-[2-(3-Carboxy-1,4-dihydro-1-dimethylamino-4-oxo-[1,7]naphthyridin-6-ylsulfanyl)-ethylamino]propionyl}-6-O-methyl-erythromycin A, 4"-O-{3-[2-(3-Carboxy-1,4-dihydro-1-dimethylamino-4-oxo-7-quinolinyl)oxyethylamino]propionyl}-6-O-methylerythromycin A, 4"-O-{3-[2-(3-Carboxy-1,4-dihydro-1-dimethylamino-4-oxo-7-quinolinyl)oxyethylamino]propionyl}-azithromycin, 4"-O-{3-[2-(3-Carboxy-1,4-dihydro-1-dimethylamino-4-oxo-7-quinolinyl)oxyethylamino]propionyl}-erythromycin A (9E)-oxime, 4"-O-{3-[3-(3-Carboxy-1,4-dihydro-1-dimethylamino-4-oxo-6-quinolinyl)propylamino]propionyl}-azithromycin, 4"-O-{3-[3-(6-Carboxy-2,3-dihydro-3-methyl-7-oxo-7H-[1,3,4]oxadiazino[6,5,4-ij]quinolin-9-yl)propylamino]propionyl}-6-O-methyl erythromycin A 4"-O-{3-[3-(6-Carboxy-2,3-dihydro-3-methyl-7-oxo-7H-[1,3,4]oxadiazino[6,5,4-ij]quinolin-9-yl)propylamino]propionyl}-erythromycin A-(9E)-O-methoxymethyloxime, 4"-O-{3-[[3-(3-Carboxy-1-dimethylamino-4-oxo-1,4-dihydro-quinolin-6-yl)-propyl]-methylamino]-propyl}-6-O-methyl-11-desoxy-11-(R)-amino-erythromycin A 11,12-carbamate, 4"-O-(2-{2-(3-Carboxy-1-dimethylamino-4-oxo-1,4-dihydro-[1,7]-naphthyridine-6-ylsulfanyl)-ethylamino}-ethyl)-6-O-methyl-erythromycin A 11,12-carbonate, 4"-O-{3-[2-(3-Carboxy-1,4-dihydro-1-(N,N-dimethylamino)-4-oxo-6-quinolinyl)sulfanylethylamino]propionyl}-6-O-methylerythromycin A, 4"-O-{3-[3-(3-Carboxy-1,4-dihydro-1-(N,N-dimethylamino)-4-oxo-6-quinolinyl)propylamino]propionyl}-erythromycin A-(9E)-oxime-11,12-carbonate, 4"-O-{3-[3-(3-Carboxy-1-dimethylamino-4-oxo-1,4-dihydro-quinolin-6-yl)-propoxy]-propyl}-6-O-methyl-erythromycin A monoformate, 4"-O-{2-[(2-{[3-Carboxy-1-(dimethylamino)-4-oxo-1,4-dihydro-1,7-naphthyridin-6-yl]thio}ethyl)amino]ethyl}-6-O-methyl-erythromycin A, 4"-O-{2-[(2-{[3-Carboxy-1-(dimethylamino)-4-oxo-1,4-dihydro-7-quinolinyl]oxy}ethyl)amino]ethyl}-6-O-methyl-erythromycin A, 4"-O {3-[2-{[6-Carboxy-8-(dimethylamino)-5-oxo-5,8-dihydro-1,8-naphthyridin-3-yl]thio}ethylamino]propionyl}-6-O-methylerythromycin A, 4"-O-{3-[3-[6-Carboxy-8-(dimethylamino)-5-oxo-5,8-dihydro-1,8-naphthyridin-3-yl])propylamino]propionyl}-6- O-methylerythromycin A, 4"-O-[3-[3-(3-Carboxy-1-dimethylamino-1,4-dihydro-4-oxo-6-quinolinyl) propylamino]propionylerythromycin A-(9E)-O-methoxymethyloxime, 4"-O-{2-[3-(3-Carboxy-1,4-dihydro-1-dimethylamino-4-oxo-6-quinolinyl)propylamino]ethyl}-6-O-methyl-erythromycin A, 4"-O-{3-[3-(3-Carboxy-1,4-dihydro-1-dimethylamino-4-oxo-7-quinolinyloxy)propylamino]propionyl}-6-O-methylerythromycin A, 4"-O-{2-[(2-{[3-Carboxy-1-(dimethylamino)-4-oxo-1,4-dihydro-7-quinolinyl]oxy}ethyl)methylamino]ethyl}-6-O-methyl-erythromycin A, 4"-O-{2-[(3-[3-Carboxy-1-(dimethylamino)-4-oxo-1,4-dihydro-6-quinolinyl]propyl)methylamino]ethyl}-6-O-methyl-erythromycin A, 4"-O-{2-[(3-[3-Carboxy-1-(morpholin-4-yl)-4-oxo-1,4-dihydro-6-quinolinyl]propyl)amino]ethyl}-6-O-methyl-erythromycin A, 4"-O-{2-[(3-[3-Carboxy-1-(methylamino)-4-oxo-1,4-dihydro-6-quinolinyl]propyl)amino]ethyl}-6-O-methyl-erythromycin A, 4"-O-{2-[(3-[3-Carboxy-1-(dimethylamino)-4-oxo-1,4-dihydro-6-quinolinyl]propyl)methylamino]ethyl}-erythromycin A-(9E)-(cyanomethyl)oxime, 4"-O-{3-[(3-[3-Carboxy-1-(dimethylamino)-4-oxo-1,4-dihydro-6-quinolinyl]propyl)methylamino]propyl}-6-O-methyl-erythromycin A, 4"-O-{2-[3-(3-carboxy-1-dimethylamino-4-oxo-1,4-dihydro-quinolin-6-yl)-propyloxy]-ethylcarbamoyl}-(9E)-O-methyloxime-erythromycin A, 4"-O-{2-[3-(3-carboxy-1-dimethylamino-4-oxo-1,4-dihydro-quinolin-6-yl)-propyloxy]-ethylcarbamoyl}-(9E)-O-methoxymethyloxime-erythromycin A, 4"-O-{2-[3-(3-carboxy-1-dimethylamino-4-oxo-1,4-dihydro-quinolin-6-yl)-propyloxy]-ethylcarbamoyl}-6-O-methyl-erythromycin A, 4"-O-{2-[3-(3-carboxy-1-dimethylamino-4-oxo-1,4-dihydro-quinolin-6-yl)-propyloxy]-ethylcarbamoyl}-9-dihydro-erythromycin-9,11-ethylidene acetal 4"-O-{2-[2-(3-carboxy-1-dimethylamino-4-oxo-1,4-dihydro-quinolyn-6-sulfanyl)-ethoxy]-ethylcarbamoyl}-(9E)-oxime-erythromycin A, 4"-O-{2-[3-(3-carboxy-1-dimethylamino-4-oxo-1,4-dihydro-quinolin-6-yl)-propyloxy]-ethylcarbamoyl}-(9E)-oxime- erythromycin A, 4"-O-{2-[2-(3-carboxy-1-dimethylamino-4-oxo-1,4-dihydro-quinolin-6-ylsulfanyl)-ethoxy]-ethylcarbamoyl}-(9E)-O-methyloxime-erythromycin A, 4"-O-{2-[2-(3-carboxy-1-dimethylamino-4-oxo-1,4-dihydro-quinolin-6-ylsulfanyl)-ethoxy]-ethylcarbamoyl}-(9E)-O-methoxymethyloxime-erythromycin A, 4"-O-{2-[2-(3-carboxy-1-dimethylamino-4-oxo-1,4-dihydro-quinolin-6-sulfanyl)-ethoxy]-ethylcarbamoyl}-(9E)-O-(2-diethylaminoethyl)-oxime-erythromycin A, 4"-O-{2-[3-(3-carboxy-1-dimethylamino-4-oxo-1,4-dihydro-quinolin-6-yl)-propyloxy]-ethylcarbamoyl}-(9E)-O-(cyanomethyl)oxime-erythromycin A, 4"-O-{2-[3-(3-carboxy-1-dimethylamino-4-oxo-1,4-dihydro-quinolin-6-yl)-propyloxy]-ethylcarbamoyl}-(9E)-O-(methoxycarbonylmethyl)oxime-erythromycin A, 4"-O-{2-[3-(3-carboxy-1-dimethylamino-4-oxo-1,4-dihydro-quinolin-6-yl)-propyloxy]-ethylcarbamoyl}-9-O-(2-diethylaminoethyl)-oxime-erythromycin A, 4"-O-{3-[[3-(3-Carboxy-1,4-dihydro-1-dimethylamino-4-oxo-6-quinolinyl)propyl]-methylamino]propionyl}-6-O-methylerythromycin A, 4"-O-{2-[[3-(3-Carboxy-1,4-dihydro-1-dimethylamino-4-oxo-6-quinolinyl)propyl]-cyclopropylamino]ethyl}-azithromycin, 4"-O-{3-[3-(3-Carboxy-1-(N,N-dimethylamino)-1,4-dihydro-4-oxo-6-quinolinyl) propylamino]propionyl}-erythromycin A (9E)-2-(diethylamino)ethyloxime, 4"-O-{3-[2-(3-Carboxy-1-(N,N-dimethylamino)-1,4-dihydro-4-oxo-7-quinolinyl)oxyethylamino]propionyl}-erythromycin A (9e)-2-(diethylamino)ethyloxime, 4"-O {3-[2-{[6-Carboxy-8-(dimethylamino)-5-oxo-5,8-dihydro-1,8-naphthyridin-3-yl]thio}ethylamino]propionyl}-erythromycin A (9E)-2-(diethylamino)ethyloxime, 4"-O-{3-[3-[6-Carboxy-8-(dimethylamino)-5-oxo-5,8-dihydro-1,8-naphthyridin-3-yl])propylamino]propionyl}-erythromycin A (9E)-2-(diethylamino)ethyloxime, 4"-O-{3-[3-(3-Carboxy-1-(N,N-dimethylamino)-1,4-dihydro-4-oxo-6-quinolinyl) propylamino]propionyl}-erythromycin A (9E)-2-(N-morpholinyl)ethyloxime or 4"-O-{2-[[3-(3-Carboxy-1-(N,N-dimethylamino)-1,4-dihydro-4-oxo-6-quinolinyl) propyl]methylamino]ethyl}-azithromycin, or a pharmaceutically acceptable salt thereof, 4"-O-{2- [2-(3-carboxy-1-dimethylamino-4-oxo-1,4-dihydro-quinolin-6-ylsulfanyl)-ethoxy]-ethylcarbamoyl}-(9E)-O-methoxymethyloxime-erythromycin A trifluoroacetate, 4"-O-{2-[2-(3-carboxy-1-dimethylamino-4-oxo-1,4-dihydro-quinolyn-6-sulfanyl)-ethoxy]-ethylcarbamoyl}-(9E)-oxime-erythromycin A trifluoroacetate salt, 4"-O-{3-[3-(3-Carboxy-1,4-dihydro-1-dimethylamino-4-oxo-6-quinolinyl)propylamino]propionyl}-6-O-methylerythromycin A lactobionate salt, 4"-O-{3-[3-(3-Carboxy-1,4-dihydro-1-dimethylamino-4-oxo-6-quinolinyl)propylamino]bropionyl}-6-O-methylerythromycin A citrate salt, 4"-O-{2-[(3-[3-carboxy-1-(dimethylamino)-4-oxo-1,4-dihydro-6-quinolinyl]propyl)methylamino]ethyl}-6-O-methyl-erythromycin A D-tartrate salt, 4"-O-{2-[(3-[3-carboxy-1-(dimethylamino)-4-oxo-1,4-dihydro-6-quinolinyl]propyl)methylamino]ethyl}-6-O-methyl-erythromycin A phosphate salt, or 4"-O-{2-[(3-[3-carboxy-1-(dimethylamino)-4-oxo-1,4-dihydro-6-quinolinyl]propyl)methylamino]ethyl}-6-O-methyl-erythromycin A fumarate salt.

13. A compound selected from the group consisting of:

4"-O-{3-[3-(3-carboxy-1,4-dihydro-1-dimethylamino-4-oxo-6-quinolinyl)propylamino]propionyl}-6-O-methylerythromycin A, 4"-O-{3-[2-(3-carboxy-1,4-dihydro-1-(N,N-dimethylamino)-4-oxo-6-quinolinyl)sulfanylethylamino]propionyl}-6-O-methylerythromycin A, and a pharmaceutically acceptable salt thereof.

14. A compound according to claim 7 wherein A is —C(O)—.

15. A compound according to claim 7 wherein A is —N($R^7$)—CH$_2$— and $R^7$ is methyl.

16. A compound according to claim 7 wherein A is —C(=N$R^{10}$)—.

17. A compound according to claim 7 wherein $U^1$ is —Y(CH$_2$)$_r$Z—.

18. A compound according to claim 17 wherein r is 2 and Z is O.

* * * * *